US006645479B1

(12) United States Patent
Shefer et al.

(10) Patent No.: US 6,645,479 B1
(45) Date of Patent: Nov. 11, 2003

(54) TARGETED DELIVERY OF ACTIVE/ BIOACTIVE AND PERFUMING COMPOSITIONS

(75) Inventors: Adi Shefer, East Brunswick, NJ (US); Shmuel David Shefer, East Brunswick, NJ (US)

(73) Assignee: International Flavors & Fragrances Inc., New York, NY (US)

(*) Notice: Subject to any disclaimer, the term of this patent is extended or adjusted under 35 U.S.C. 154(b) by 0 days.

(21) Appl. No.: 09/573,534

(22) Filed: May 19, 2000

Related U.S. Application Data

(63) Continuation of application No. 09/208,462, filed on Dec. 10, 1998, now abandoned, which is a continuation-in-part of application No. 08/933,599, filed on Sep. 18, 1997, now Pat. No. 6,042,792.

(51) Int. Cl.[7] .................................................. A61K 7/06
(52) U.S. Cl. ................ 424/70.17; 424/70.1; 424/70.12; 424/70.19; 424/70.21; 424/70.22; 424/70.27
(58) Field of Search ............................ 424/70.1, 70.11, 424/70.17, 70.19, 70.12, 70.21, 70.22, 70.27

(56) References Cited

U.S. PATENT DOCUMENTS 5,540,853 A * 7/1996 Trinh et al. .................. 510/101

* cited by examiner

*Primary Examiner*—Jyothsna Venkat
(74) *Attorney, Agent, or Firm*—Joseph F. Leightner

(57) ABSTRACT

Described are controlled, time-release microparticulate active and bioactive compositions (including perfuming compositions) for targeted delivery to surfaces such as skin, hair and fabric and the environment proximate thereto, where the active and bioactive materials have a calculated $\log_{10}P$ values of between 1 and 8 (P being the n-octanol-water partition coefficient). Such compositions include the active or bioactive material in single phase, solid solution in a wax or polymer matrix also having coated thereon and/or containing a compatible surfactant. Also described are processes and apparatus for preparing such compositions and processes for using same. Furthermore, certain component (s) of the aforementioned compositions in combination with one another are novel, and other components have novel uses in increasing fragrance substantivity, particularly in hair care preparations such as hair gels and shampoos.

11 Claims, 49 Drawing Sheets

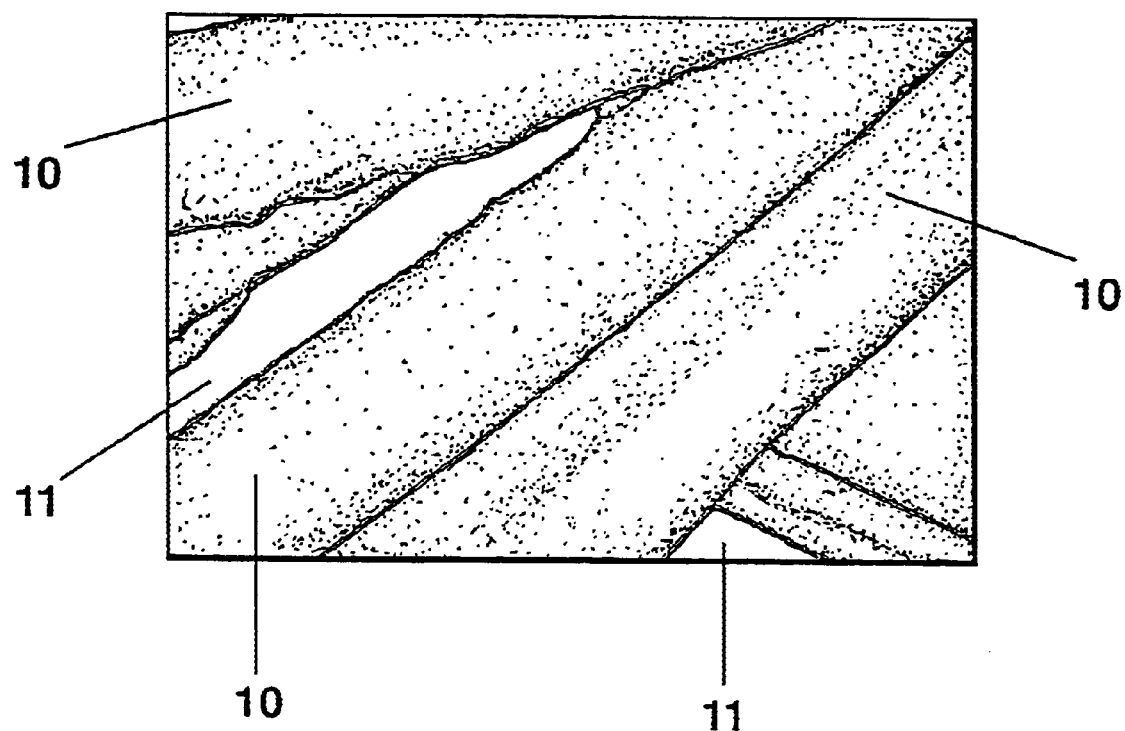
FIG.1-A

FIG.1-A (I)
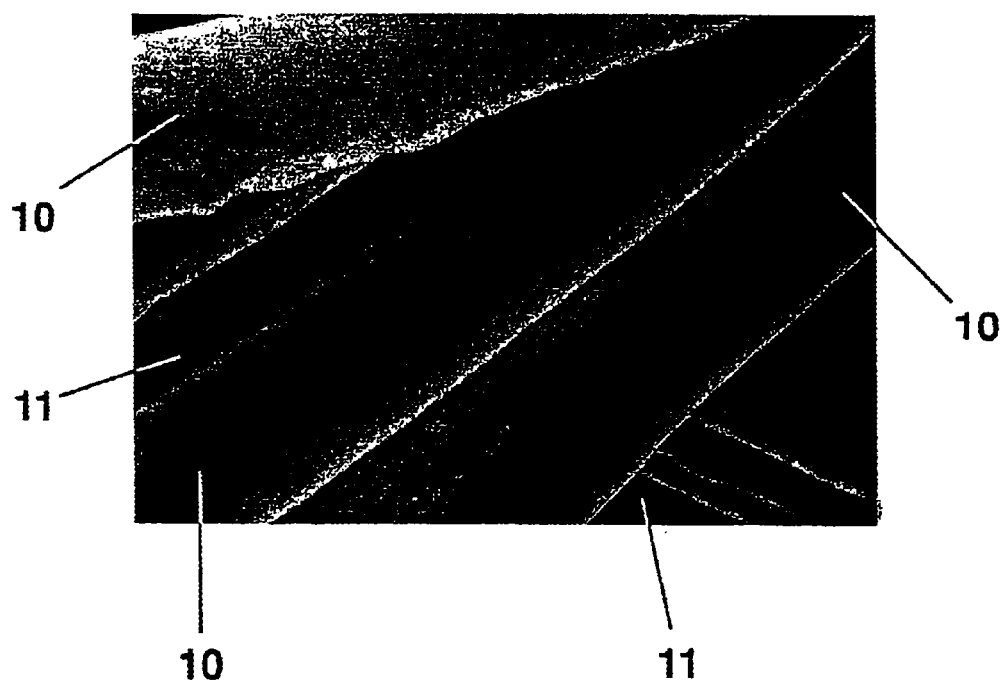

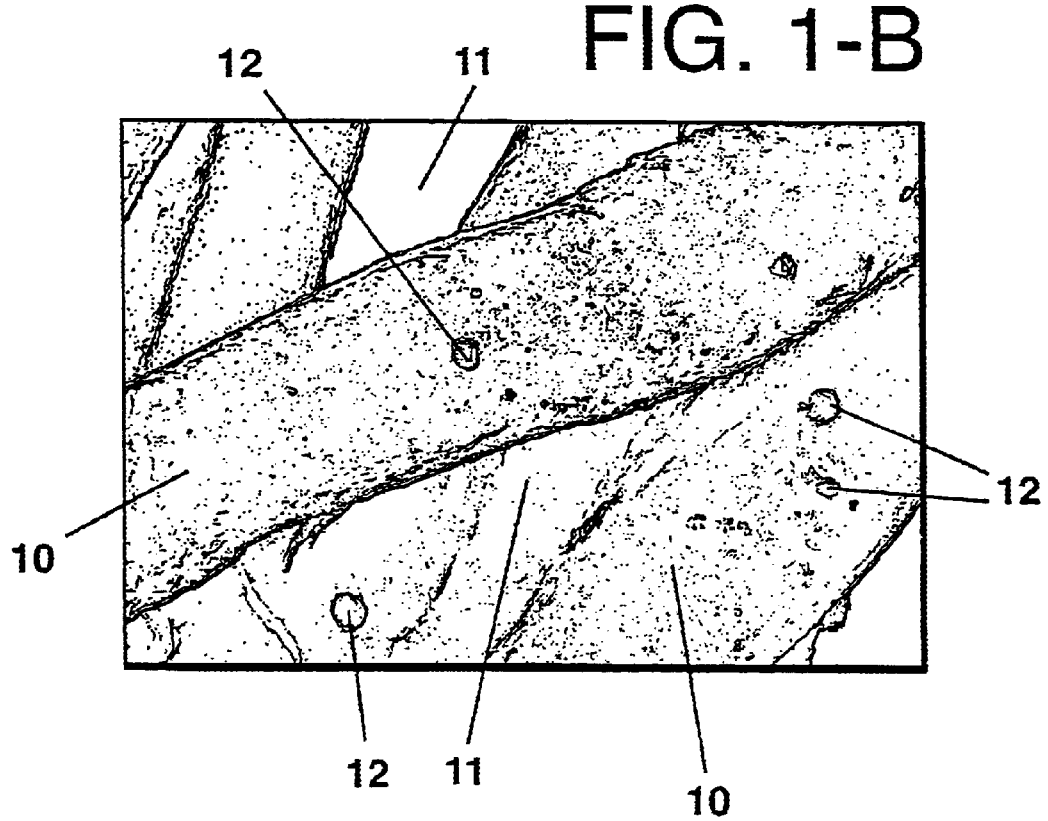
FIG. 1-B

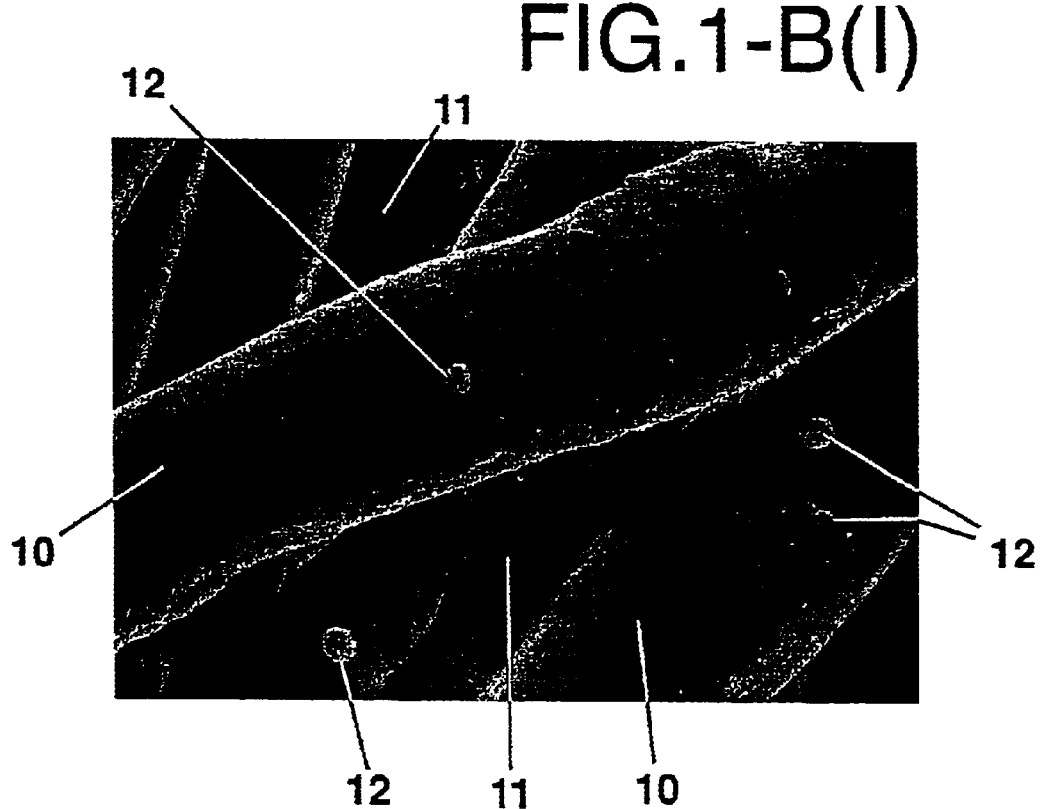
FIG.1-B(I)

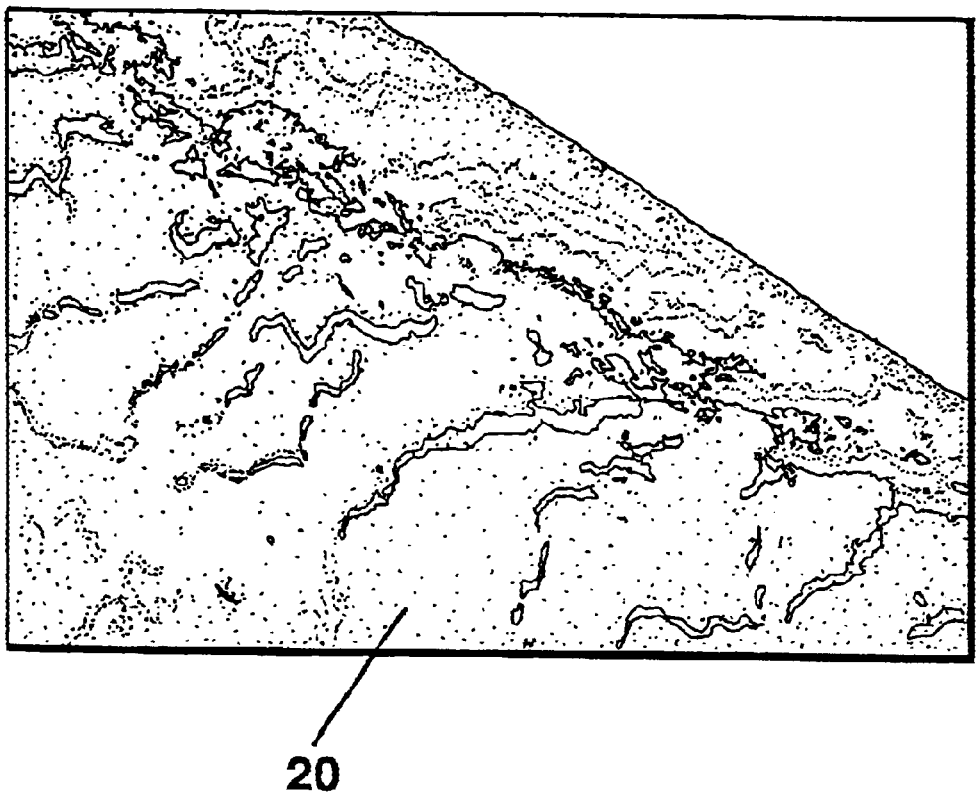
FIG.2-A

FIG. 2-A(I)
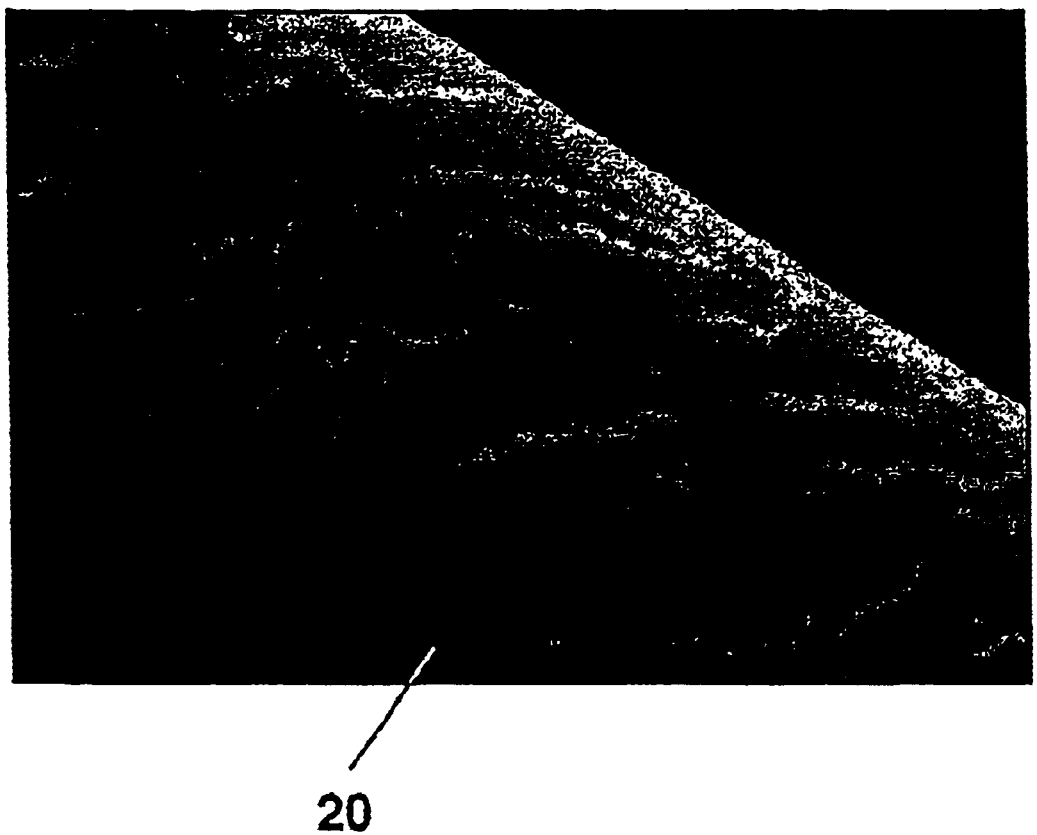
20

FIG.2-B
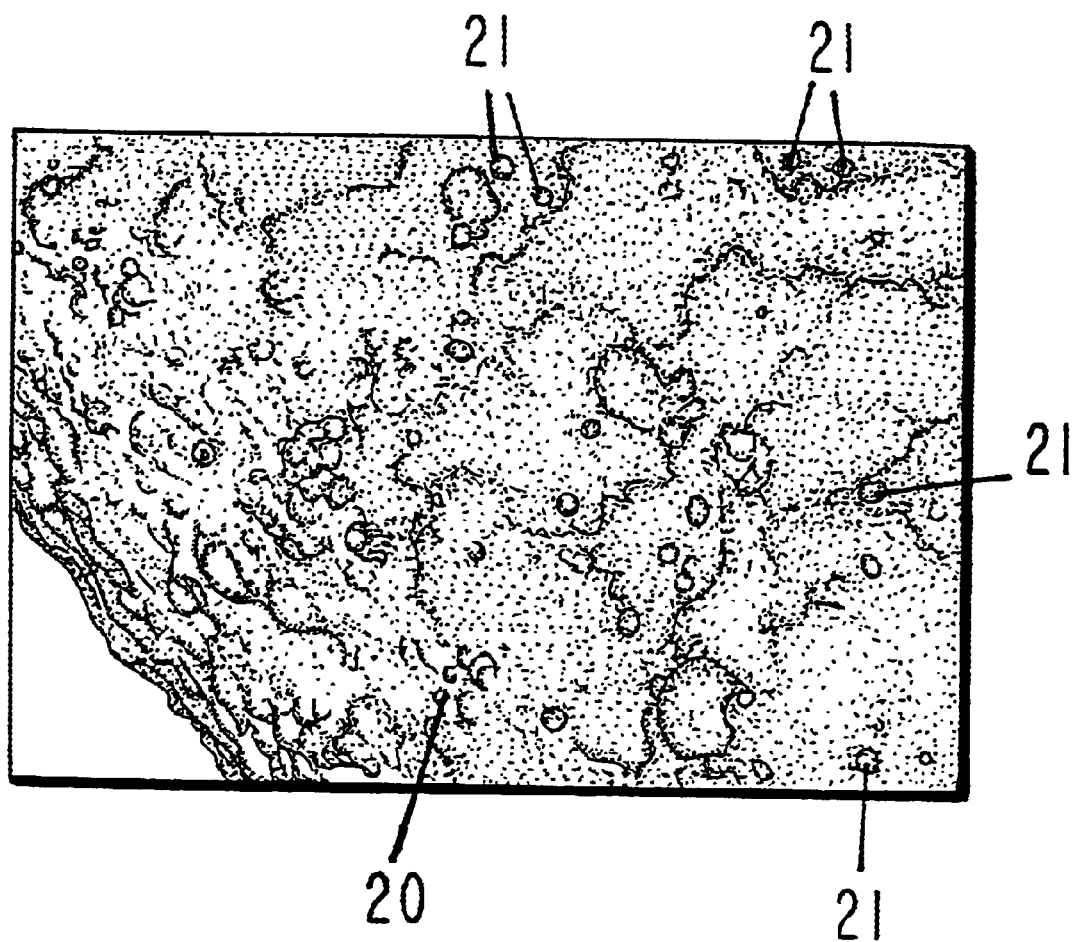

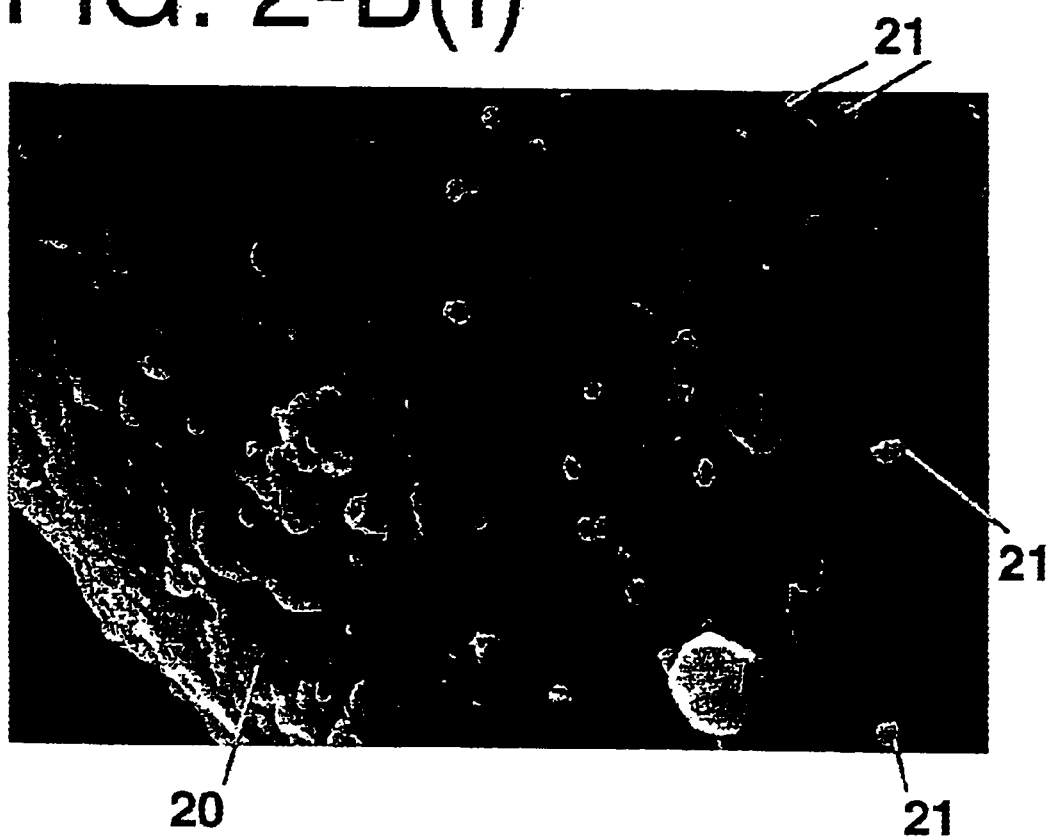
FIG. 2-B(I)

FIG.2-C
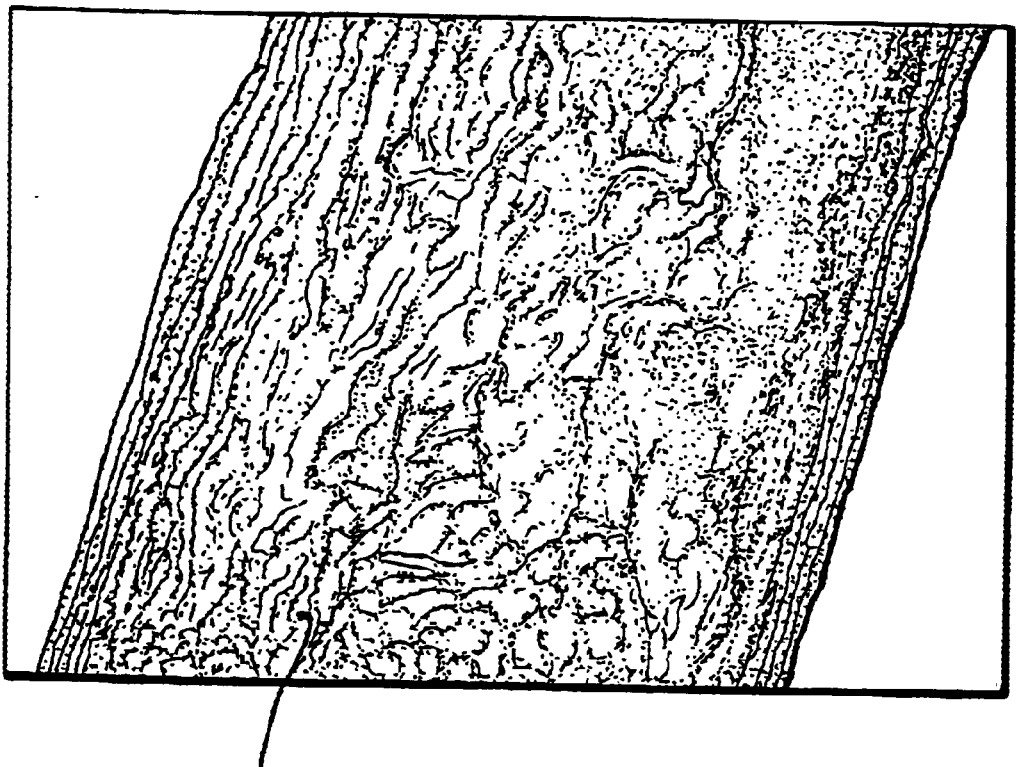
23

FIG.2-C(I)
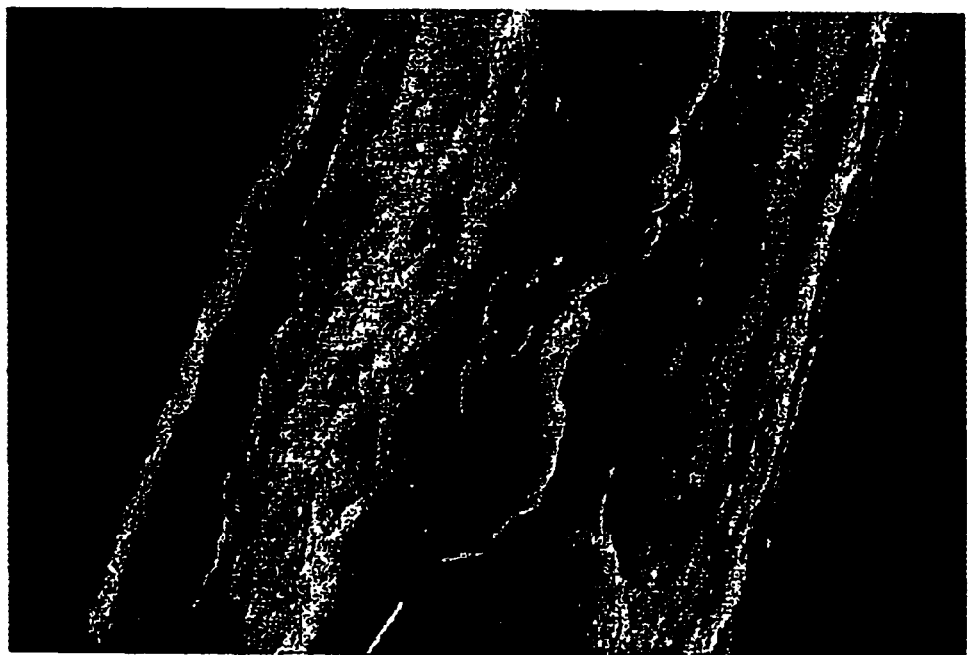
23

FIG.2-D
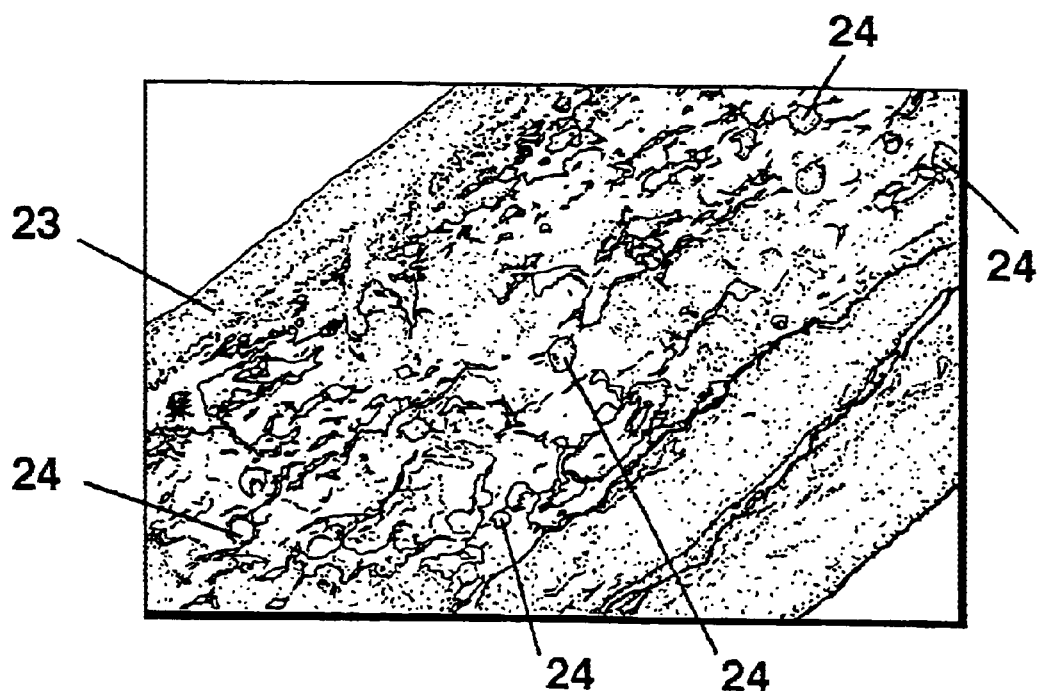

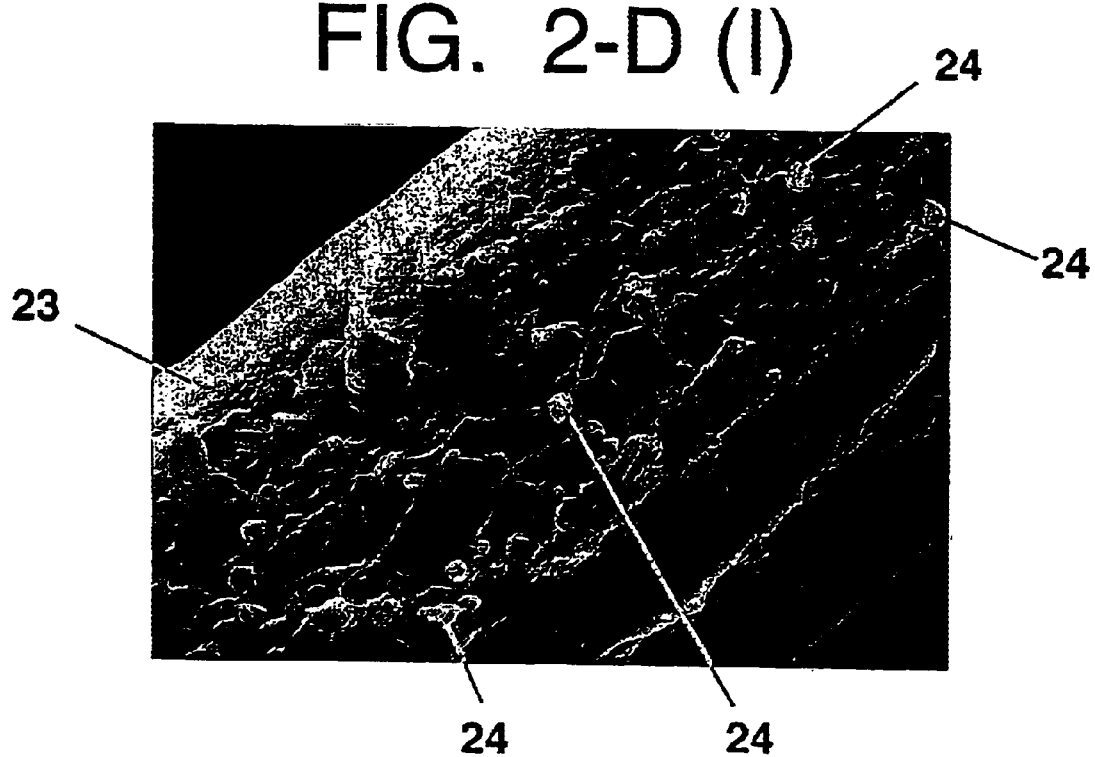
FIG. 2-D (I)

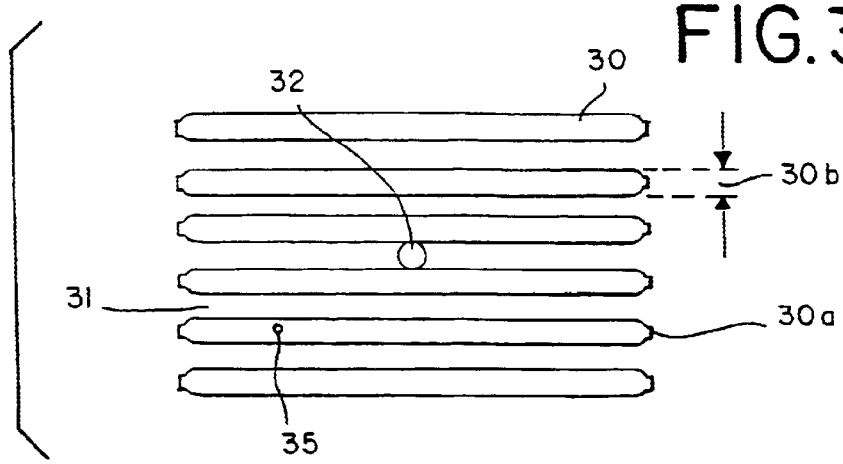
FIG.3-A
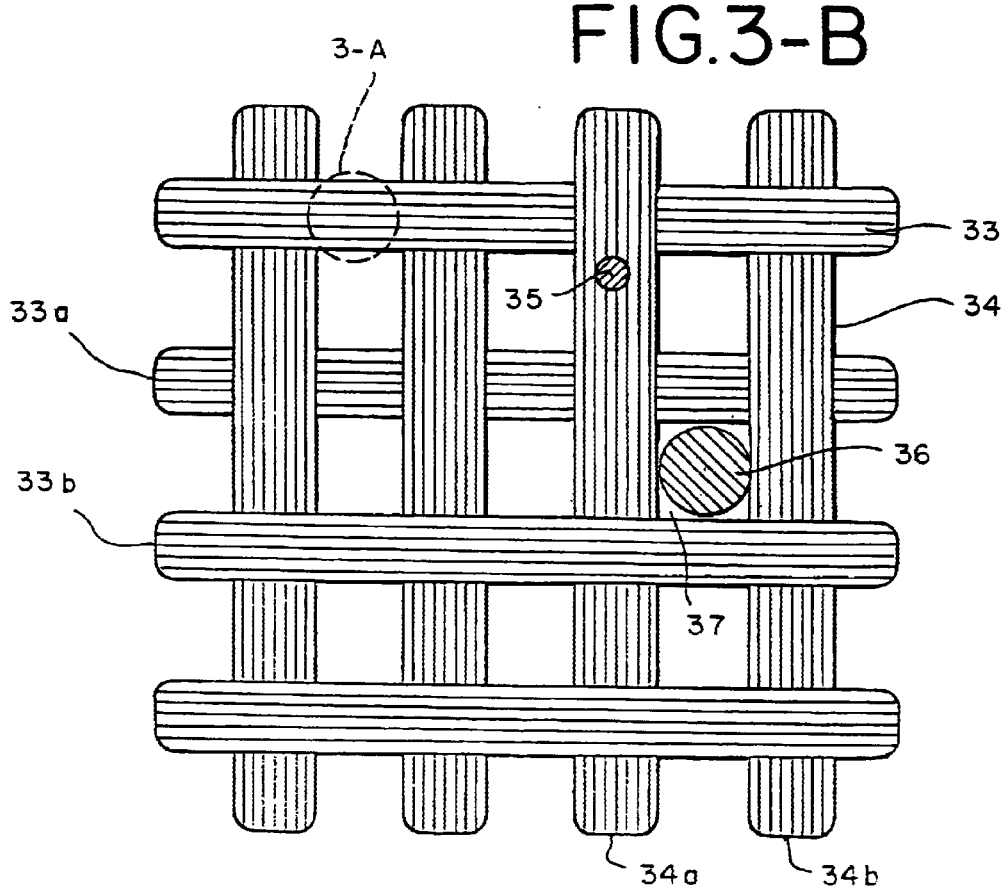
FIG.3-B

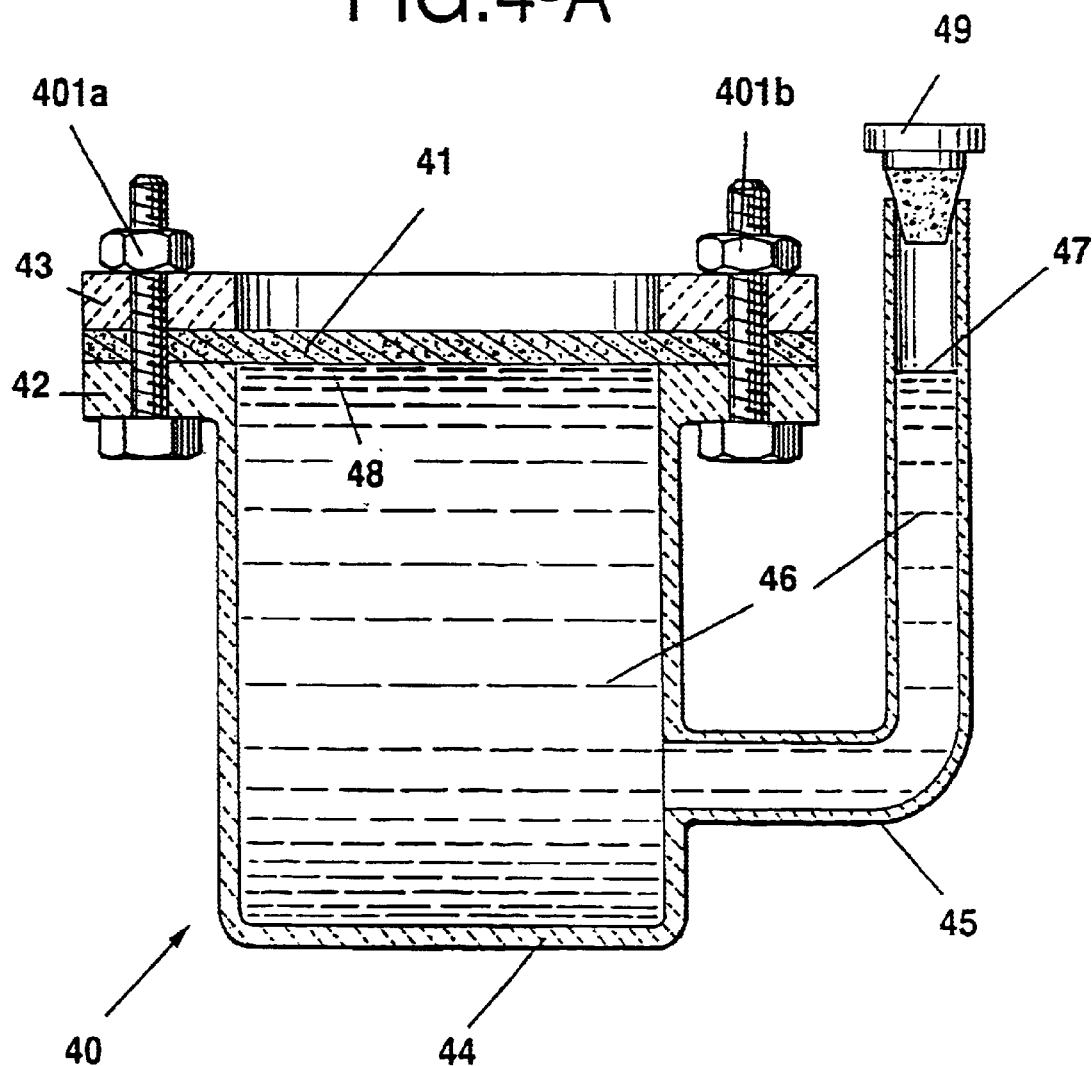
FIG.4-A

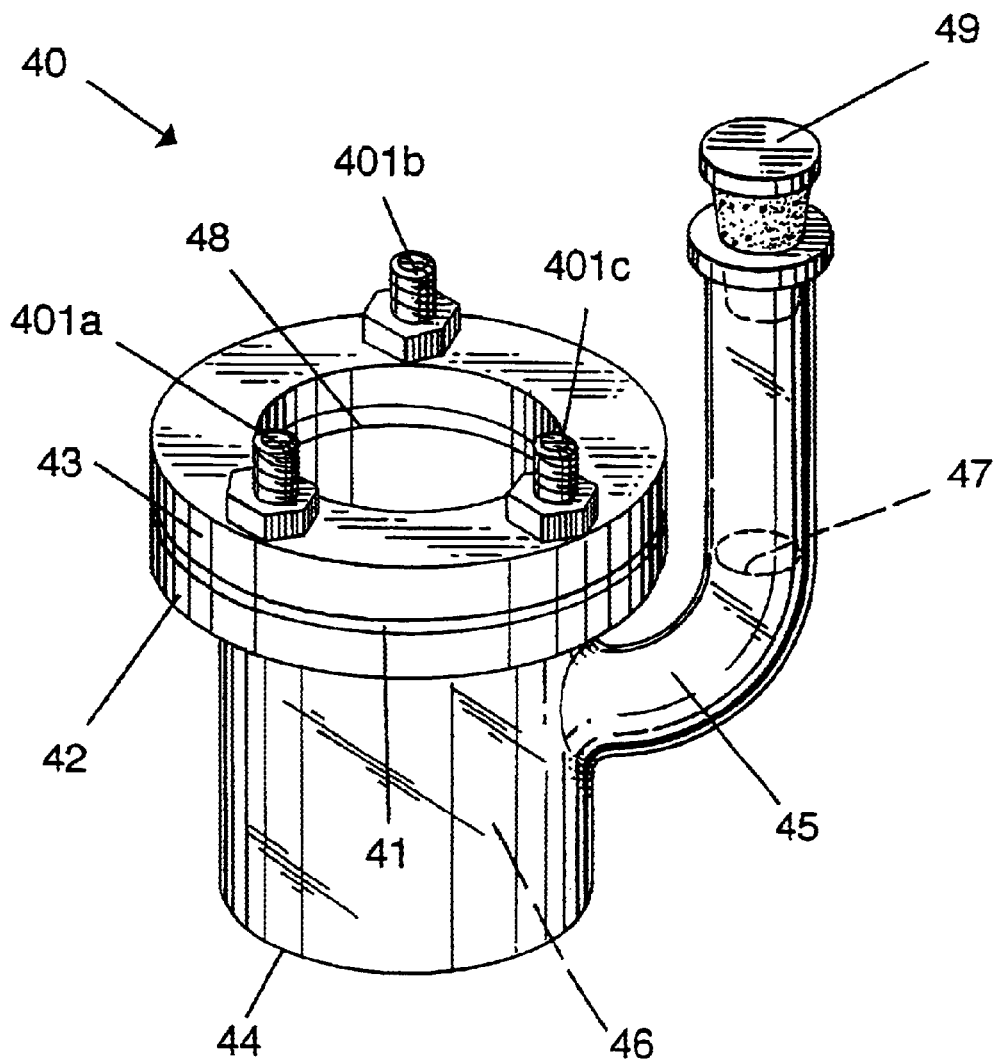
FIG.4-B

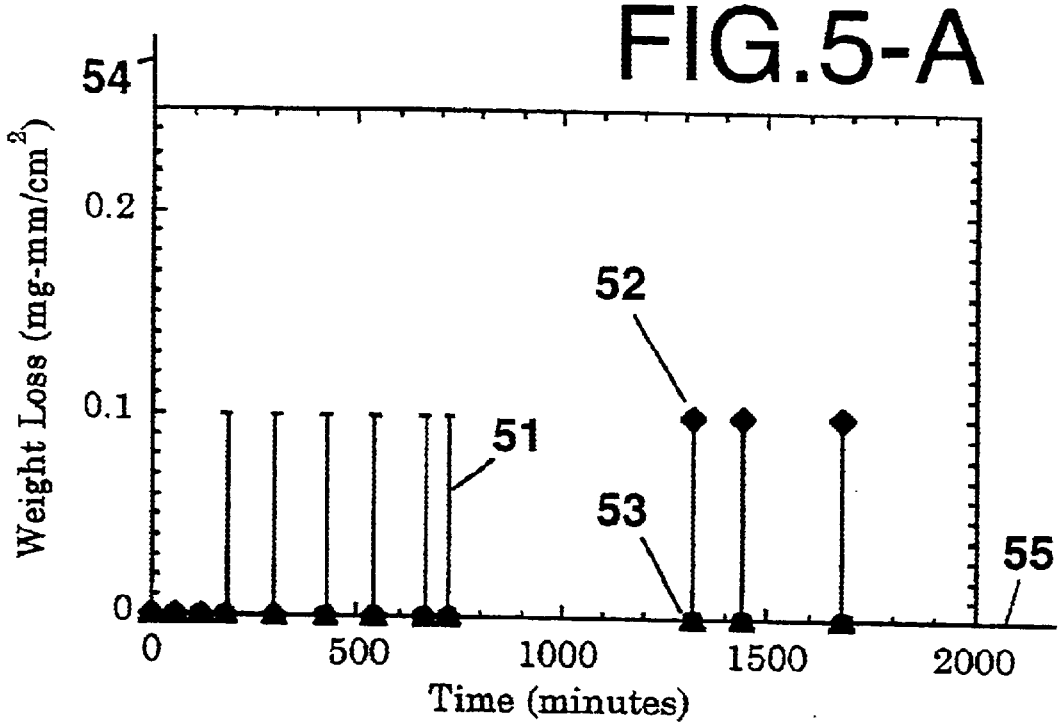
FIG.5-A
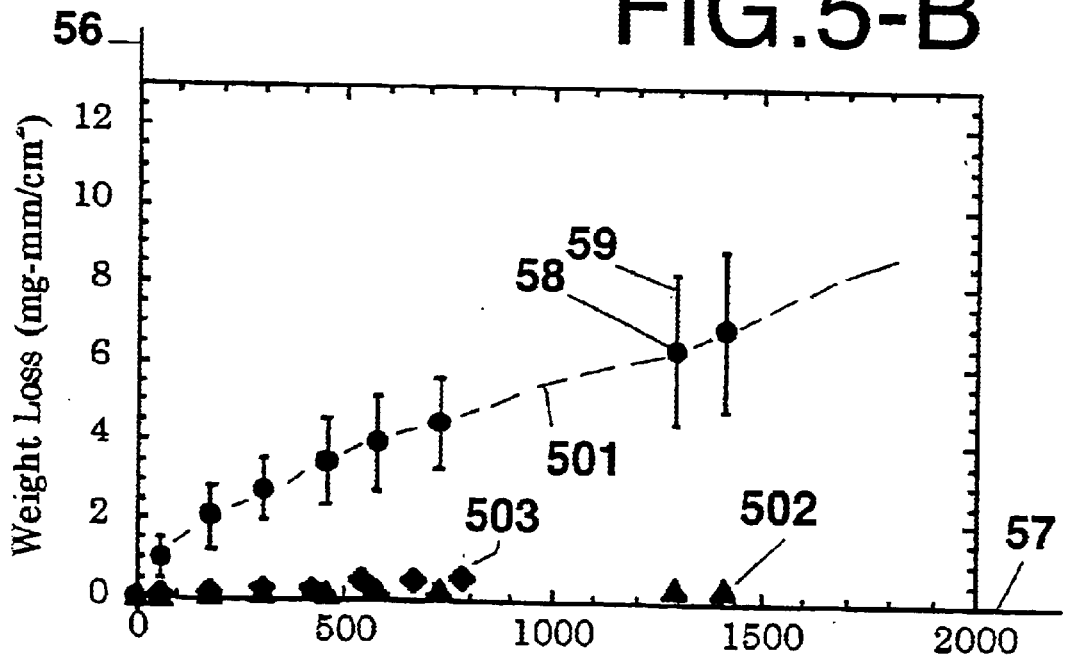
FIG.5-B

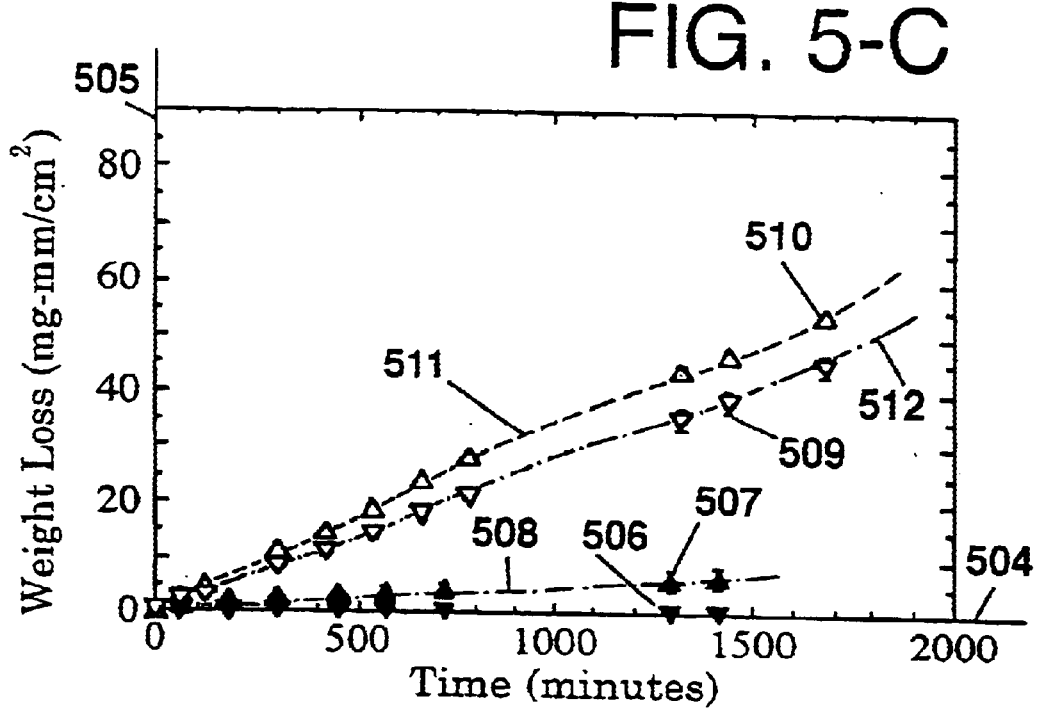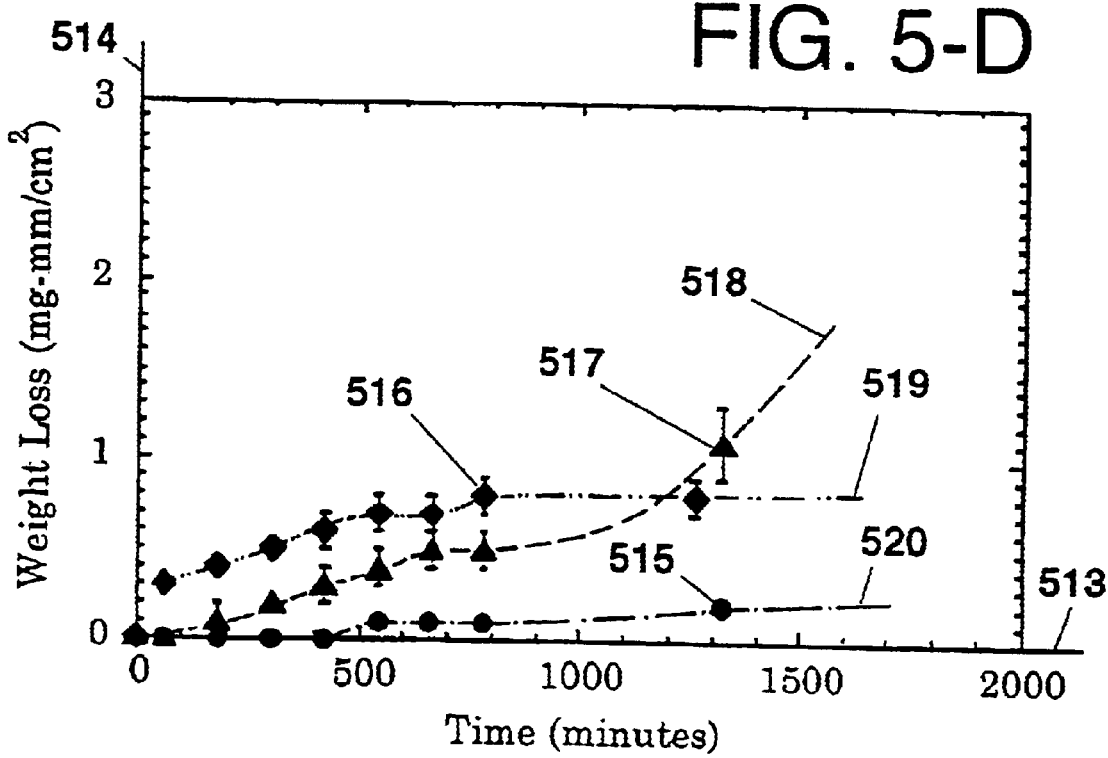

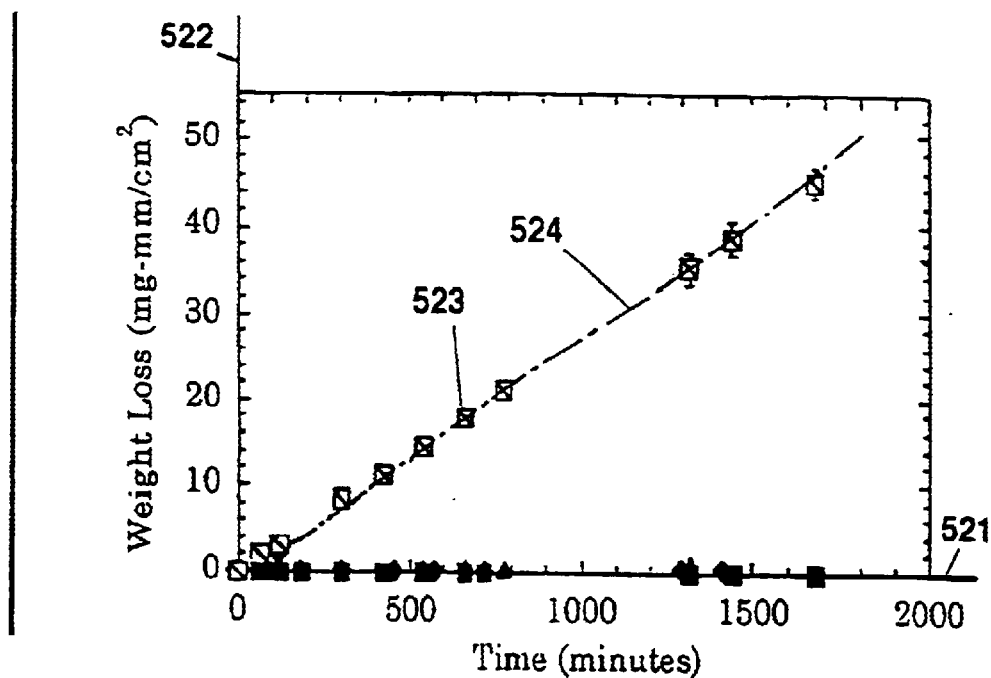
FIG.5-E
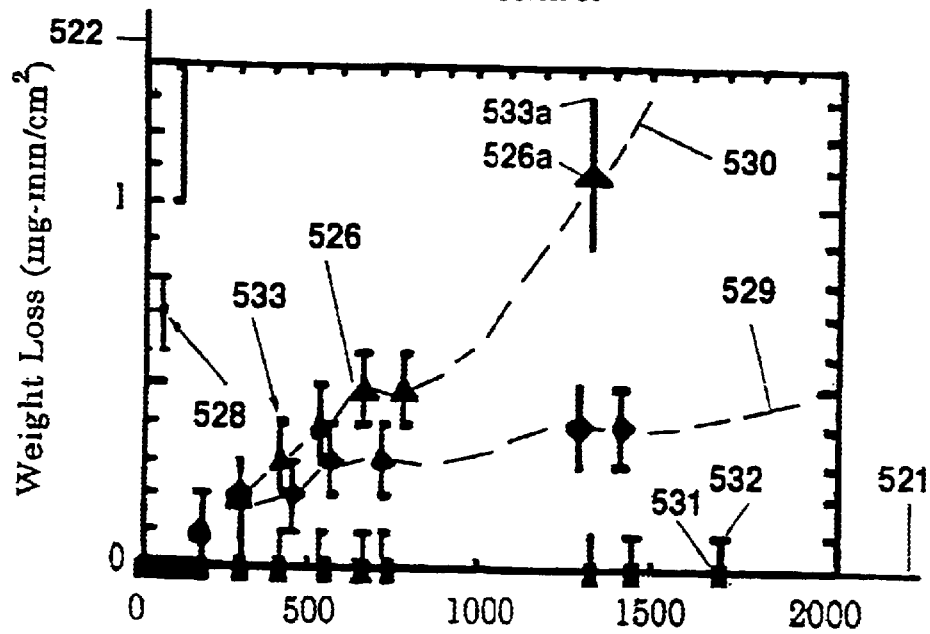
FIG.5-E(A)

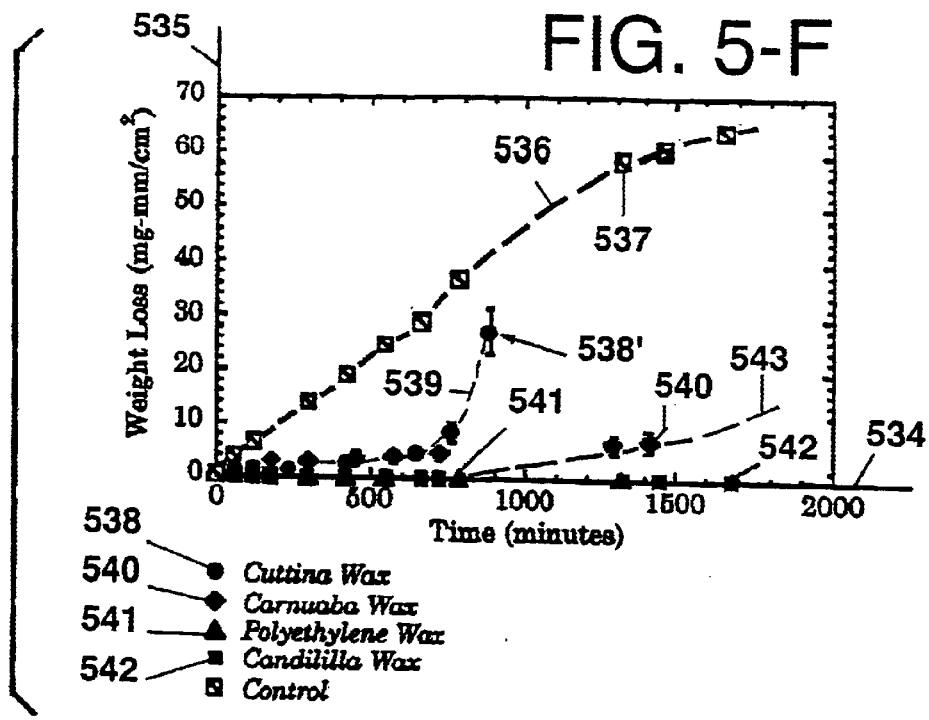
FIG. 5-F
- 538 ● Cuttina Wax
- 540 ◆ Carnuaba Wax
- 541 ▲ Polyethylene Wax
- 542 ■ Candililla Wax
- □ Control
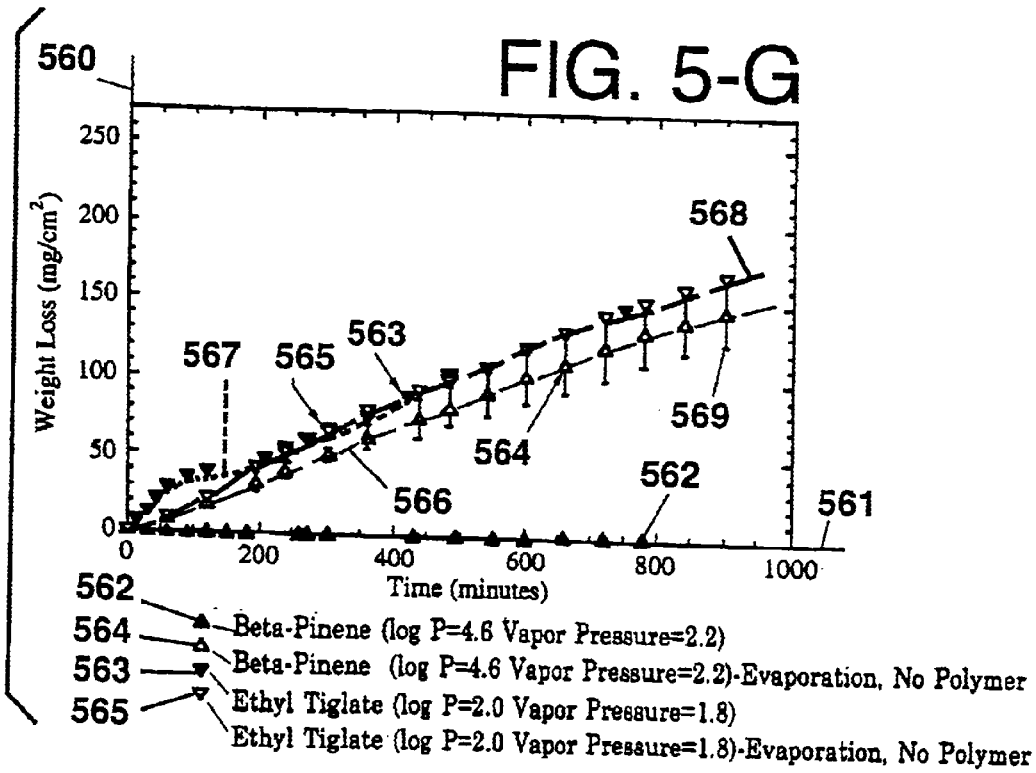
FIG. 5-G
- 562 ▲ Beta-Pinene (log P=4.6 Vapor Pressure=2.2)
- 564 △ Beta-Pinene (log P=4.6 Vapor Pressure=2.2)-Evaporation, No Polymer
- 563 ▼ Ethyl Tiglate (log P=2.0 Vapor Pressure=1.8)
- 565 ▽ Ethyl Tiglate (log P=2.0 Vapor Pressure=1.8)-Evaporation, No Polymer

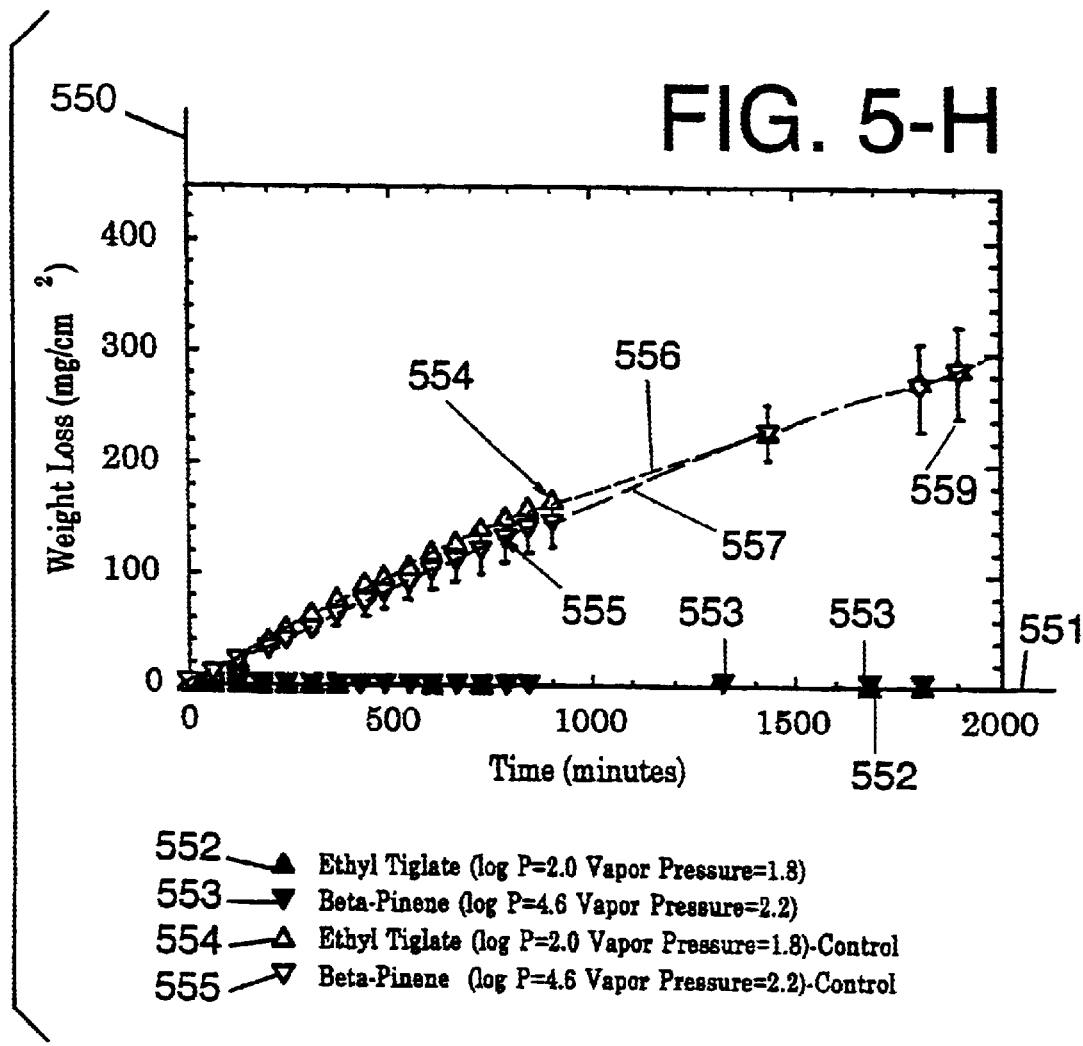

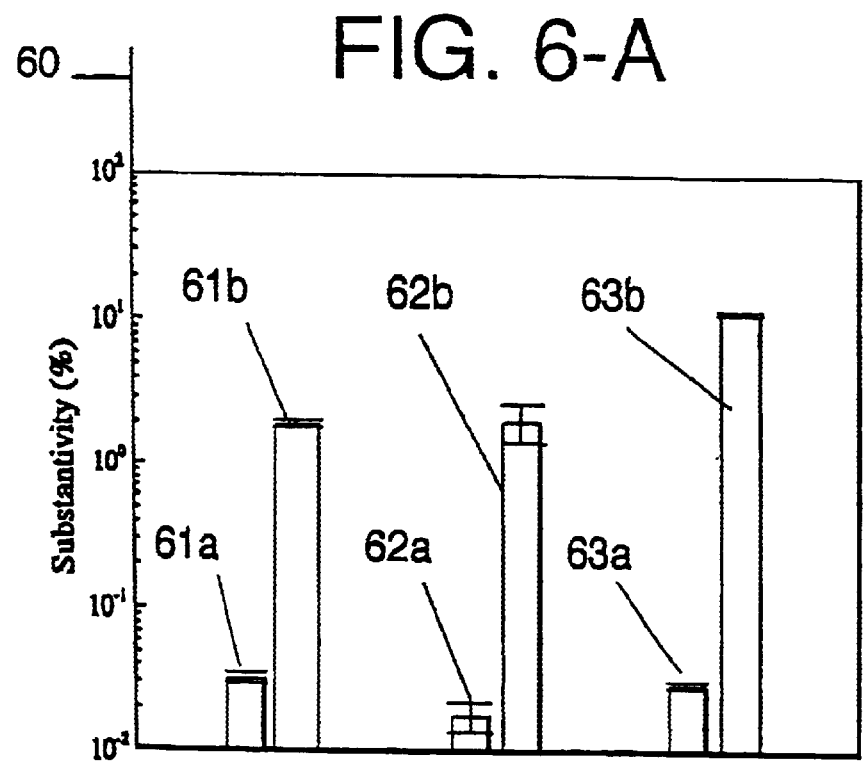
FIG. 6-A
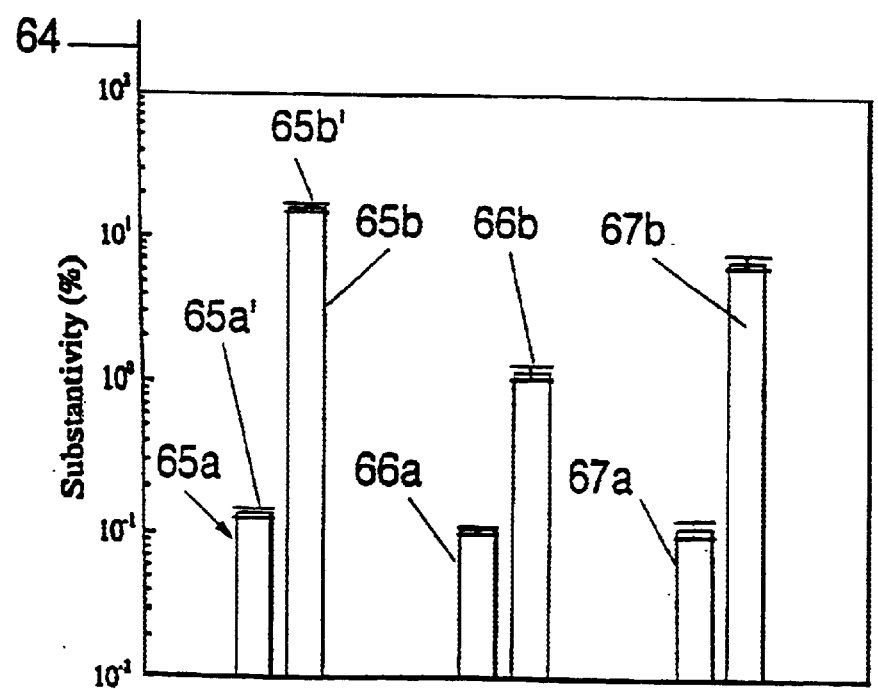
FIG. 6-B

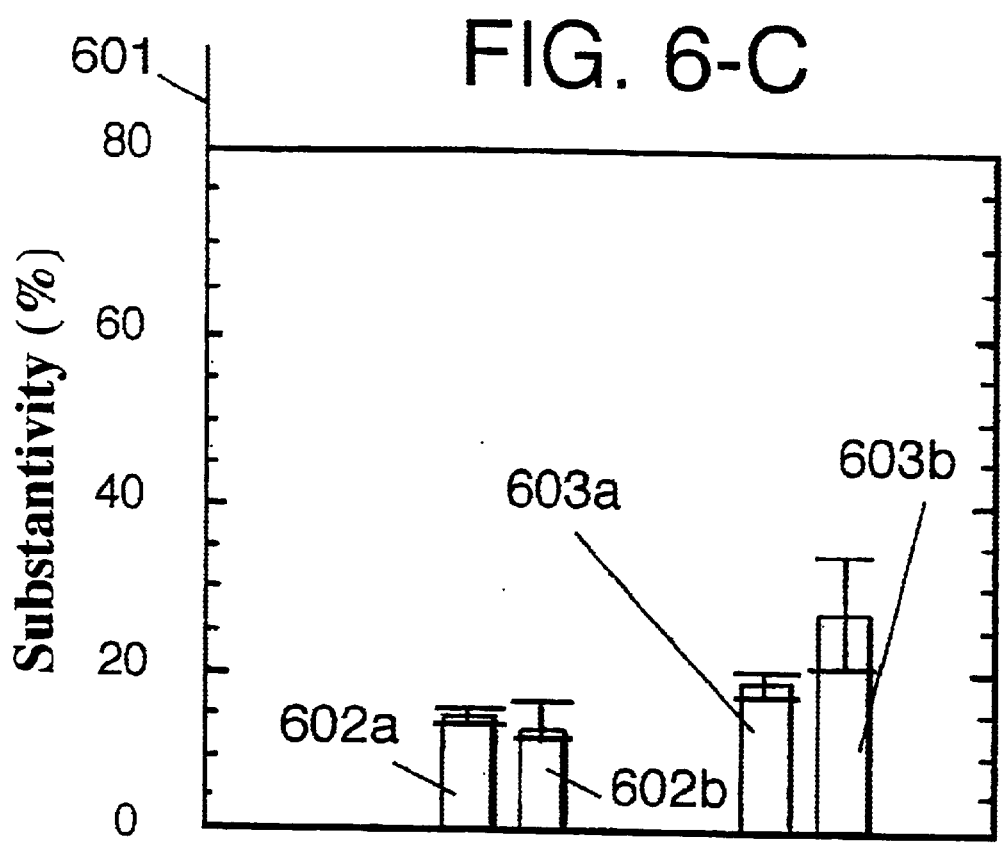
FIG. 6-C
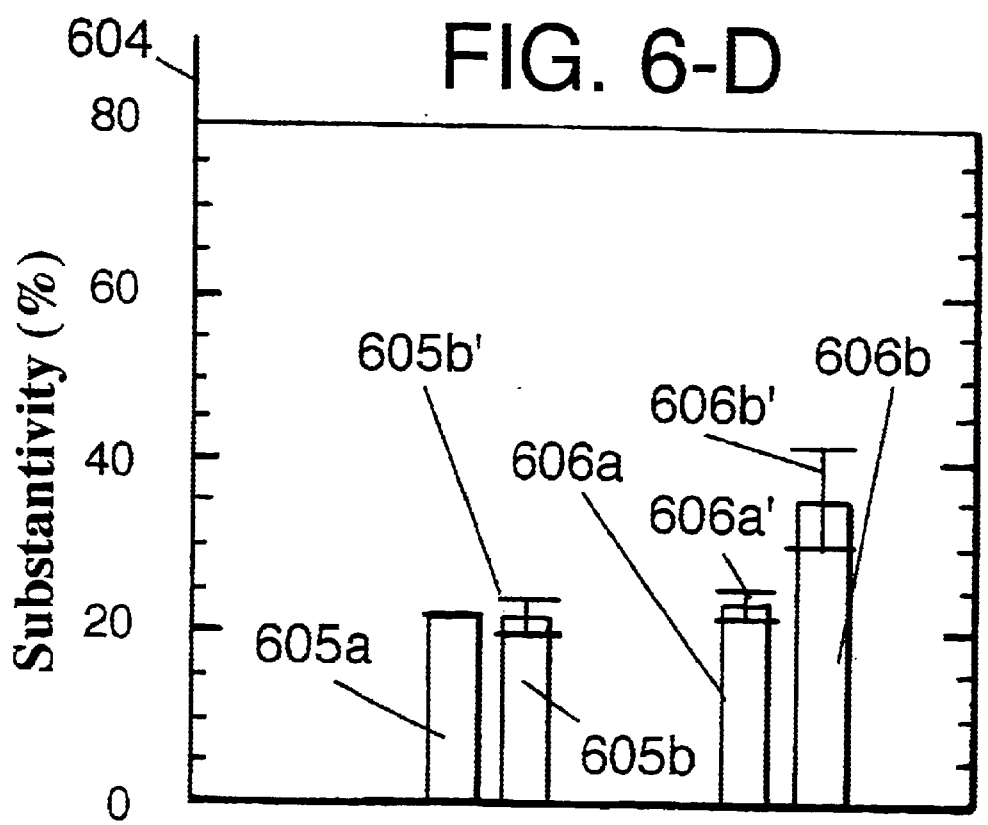
FIG. 6-D

FIG. 7-A
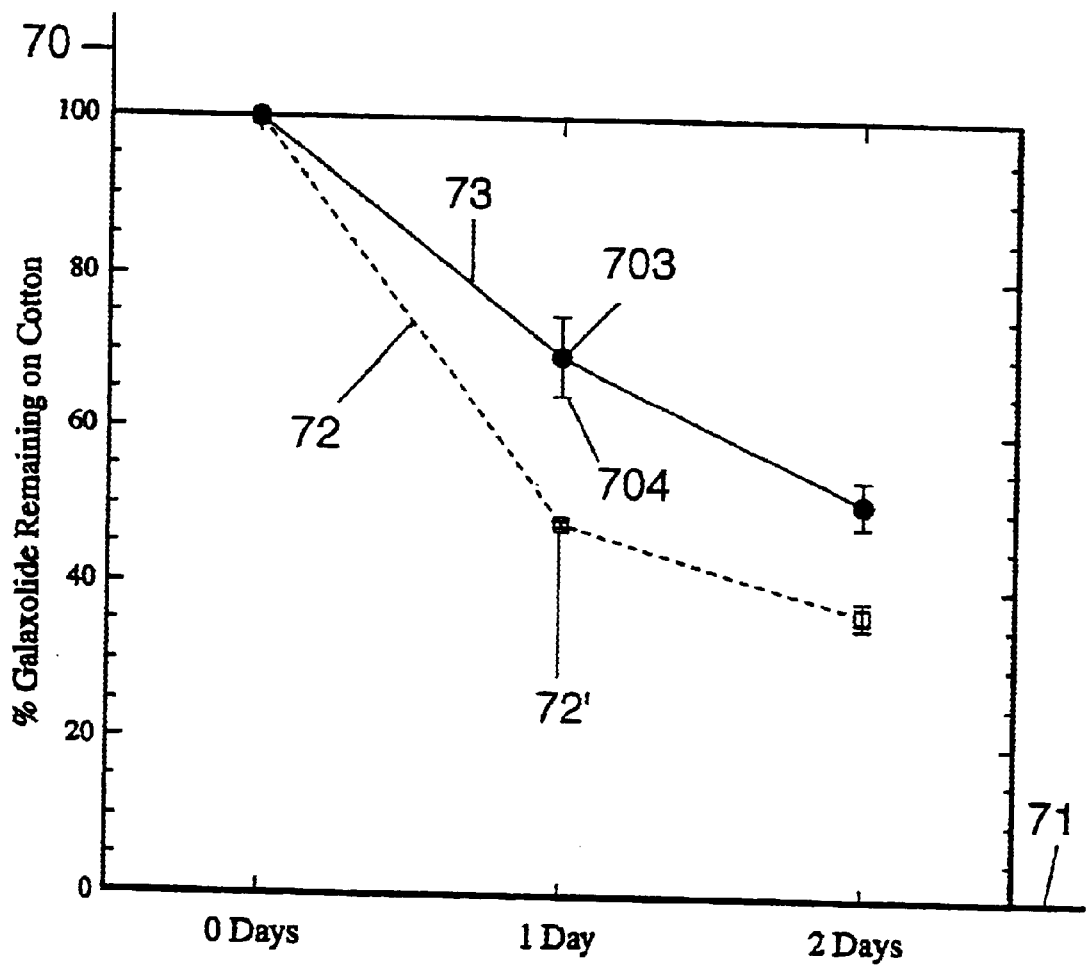

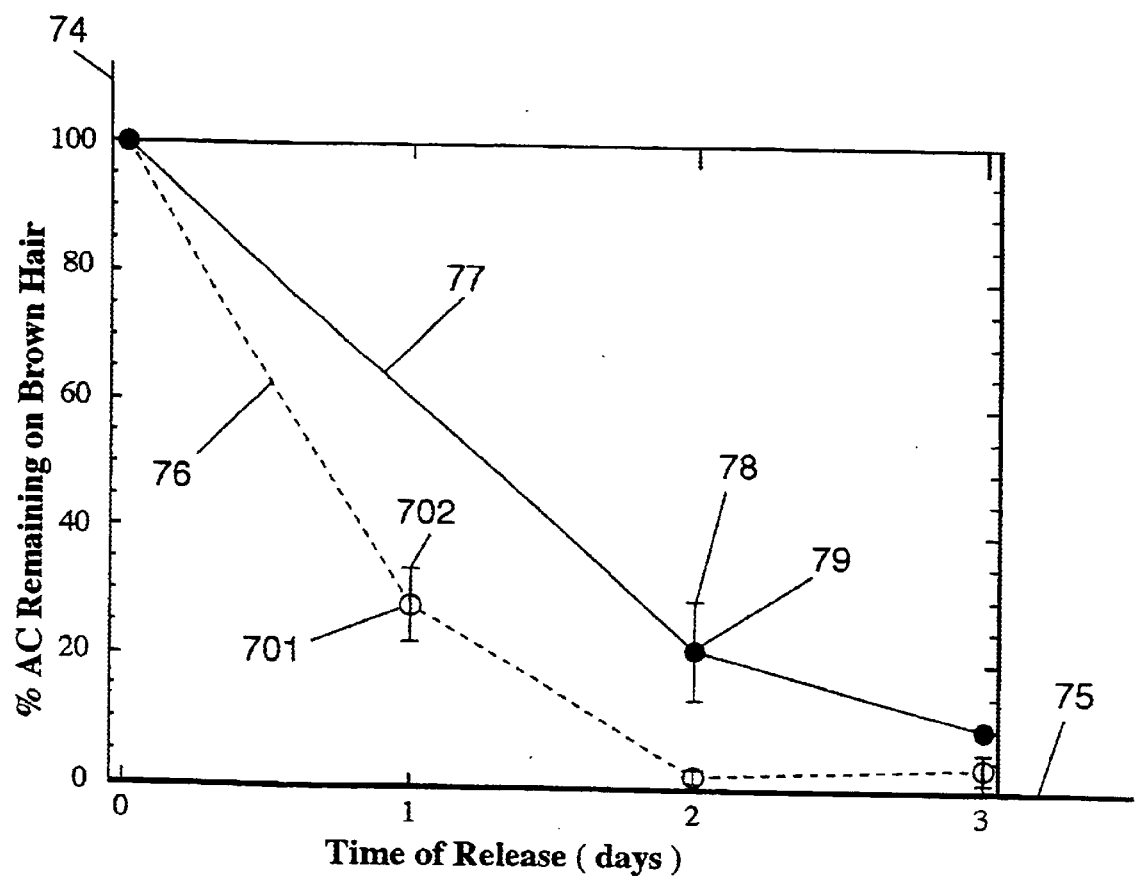
FIG. 7-B

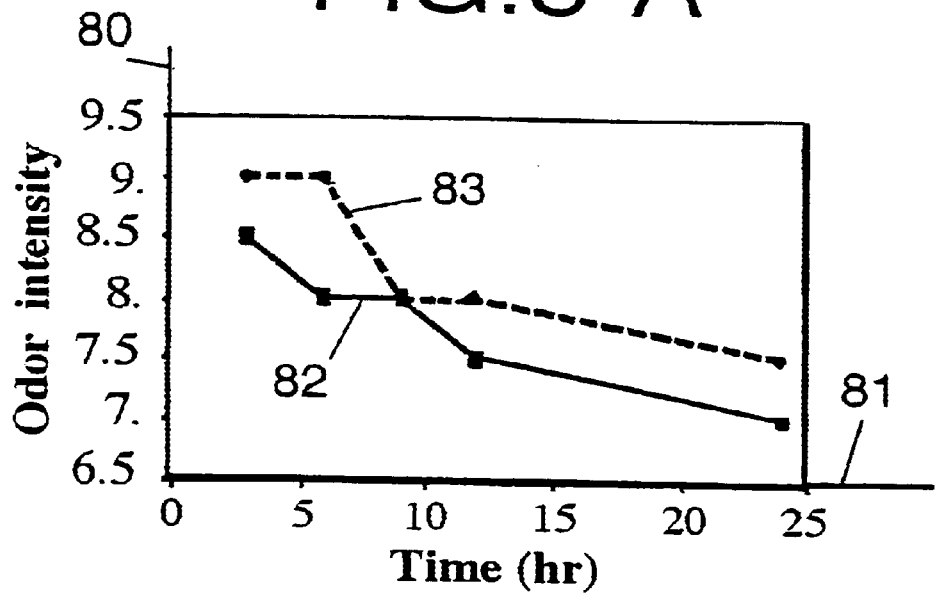
FIG.8-A
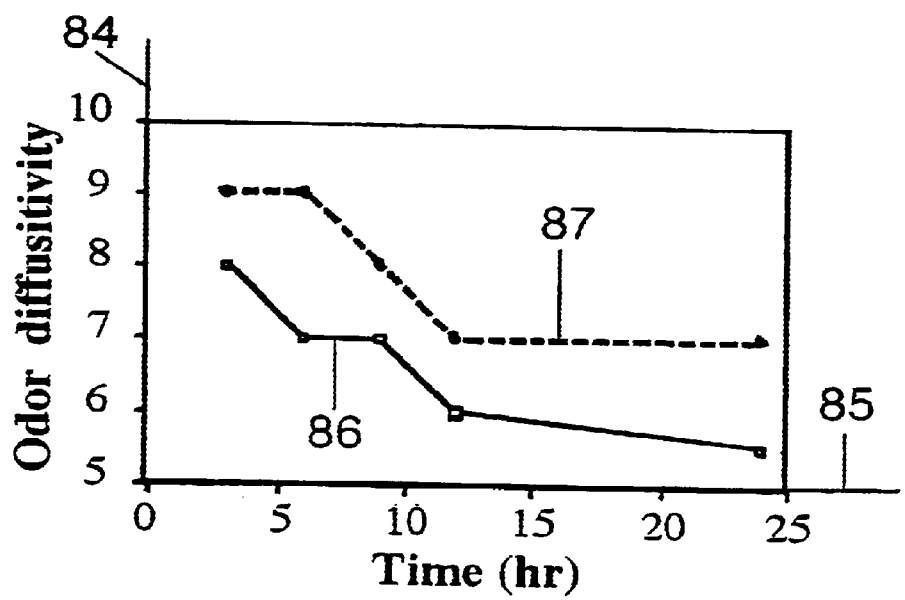
FIG.8-B

FIG. 8-C
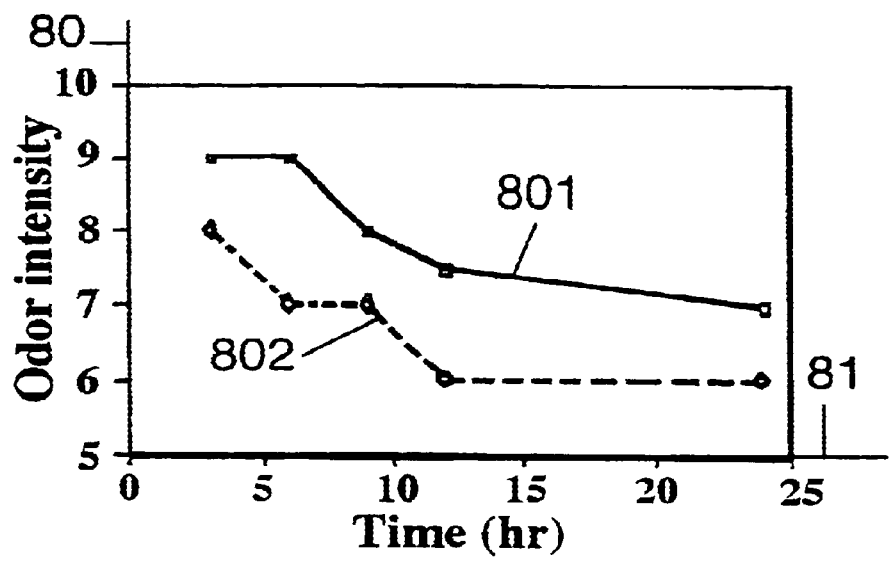
FIG. 8-D
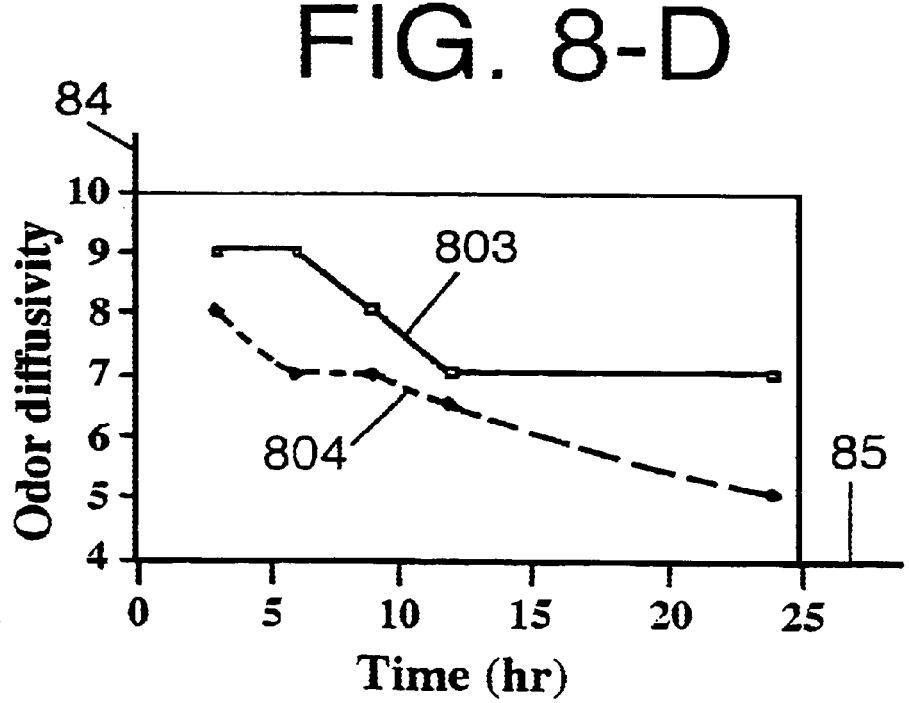

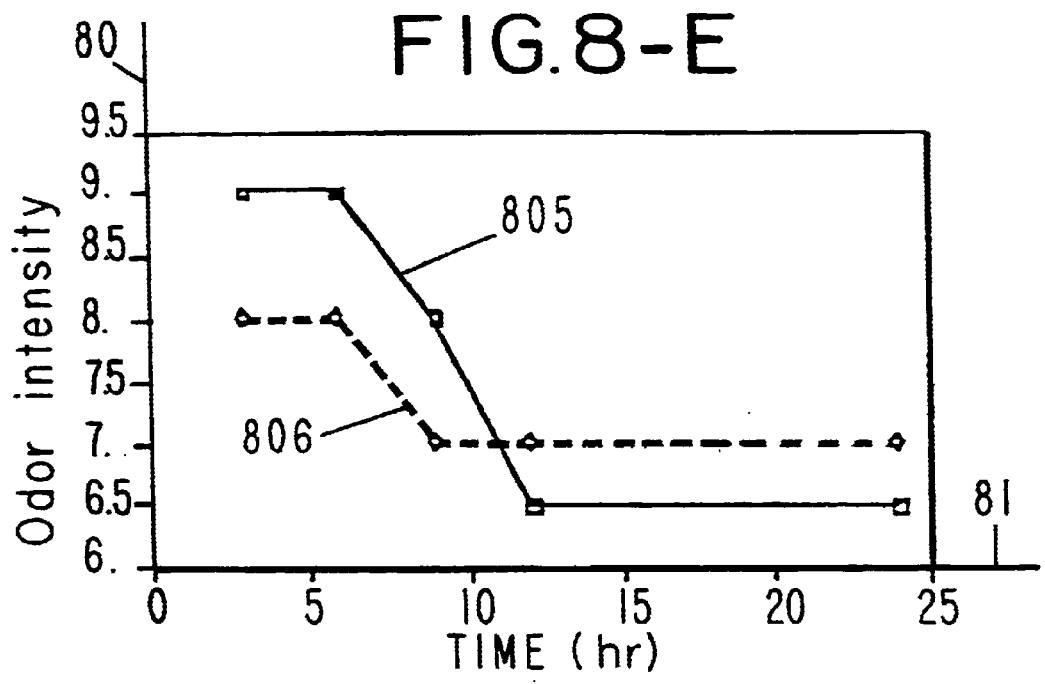
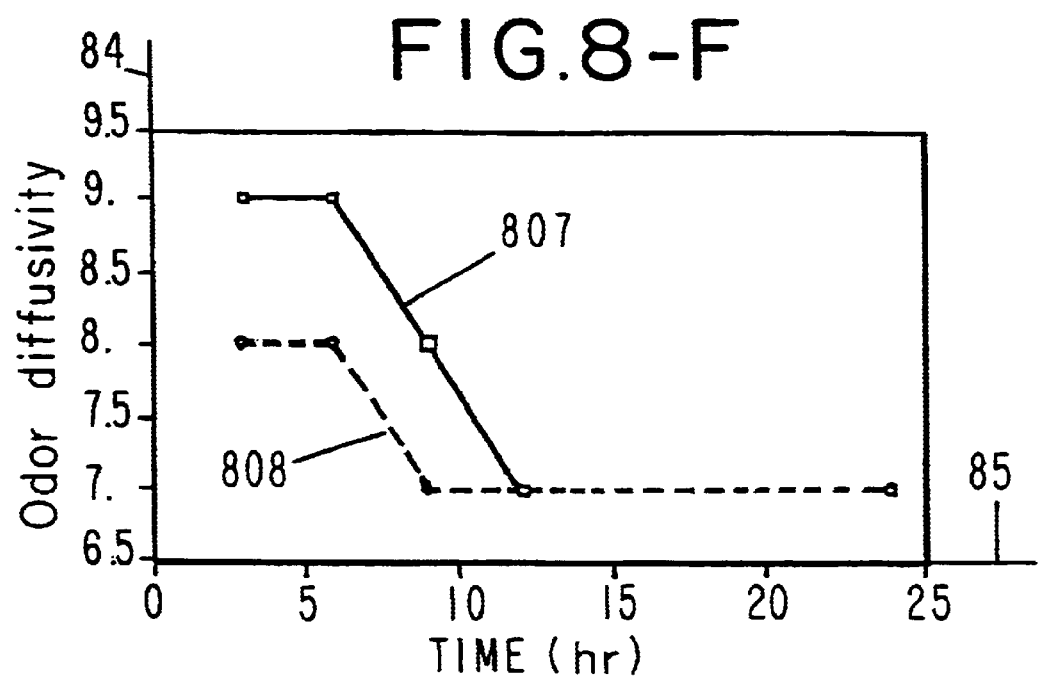

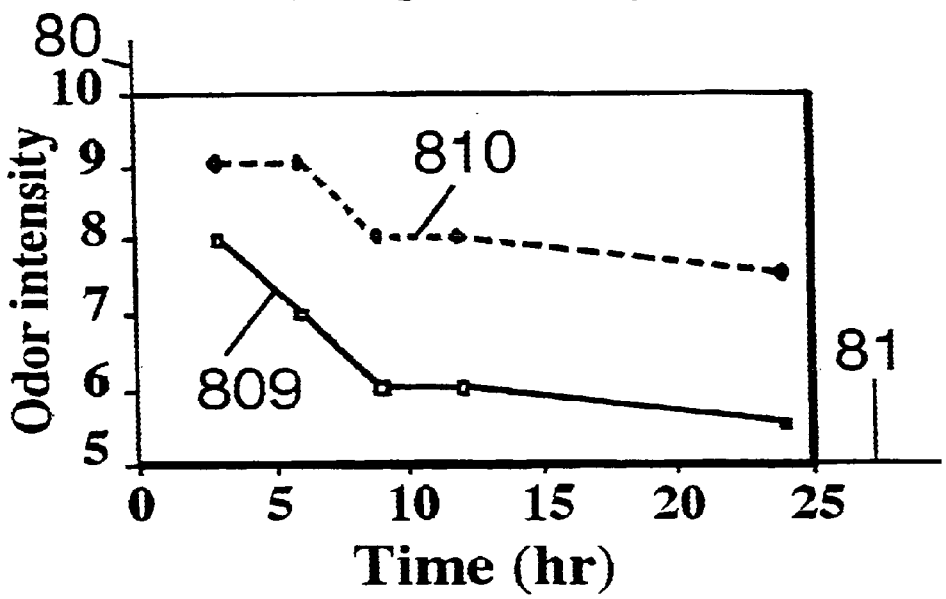
FIG. 8-G
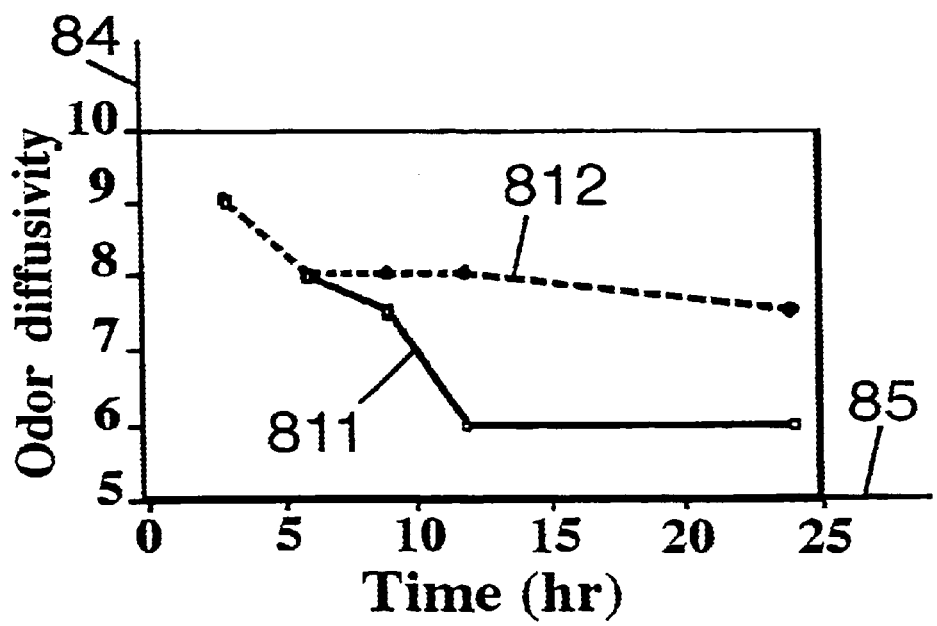
FIG. 8-H

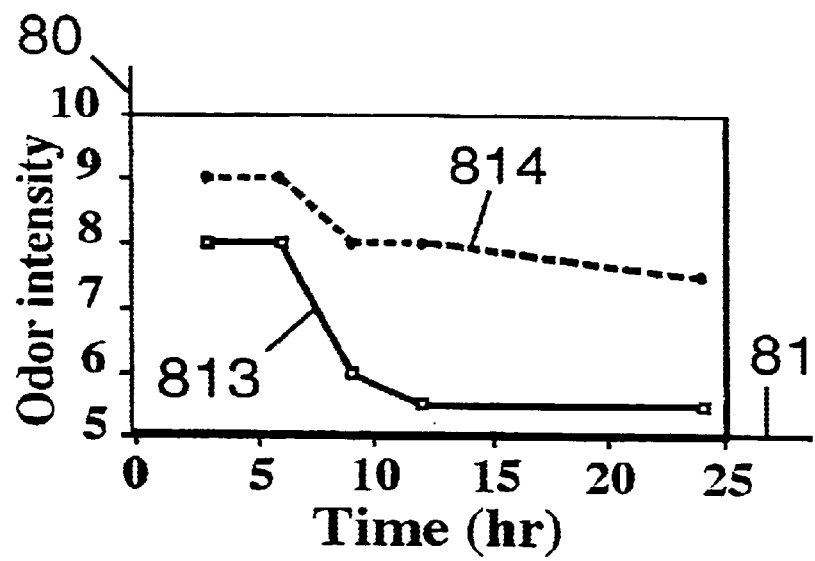
FIG.8-I
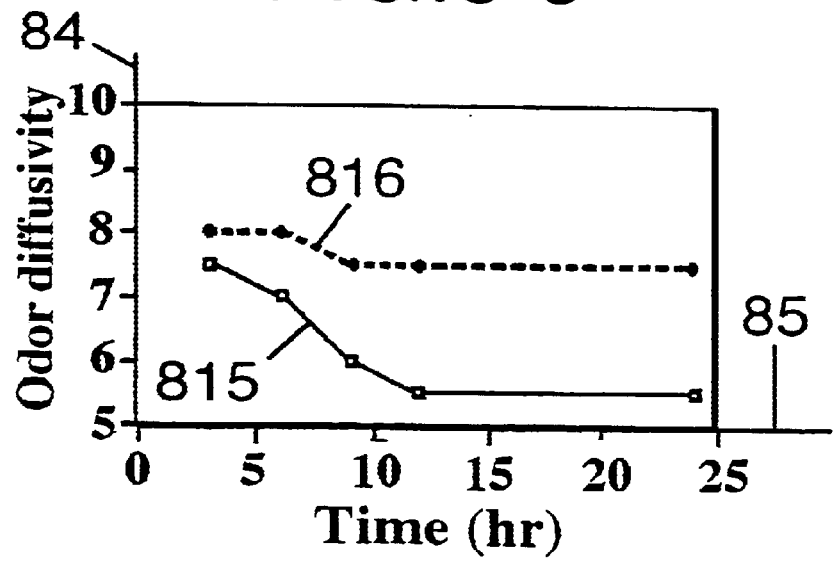
FIG.8-J

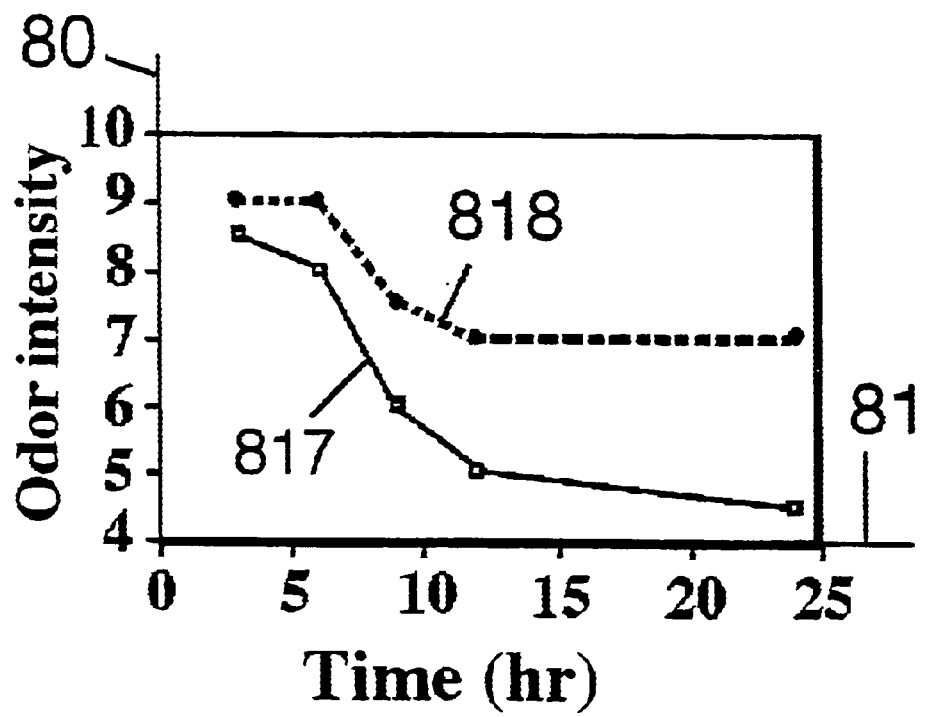
FIG. 8-K
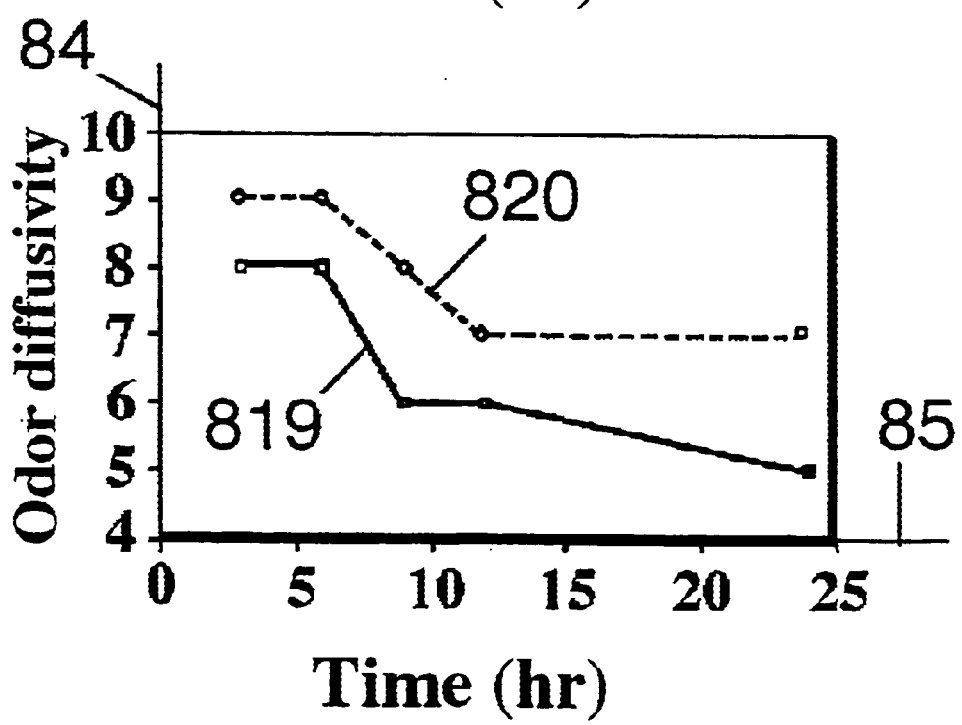
FIG. 8-L

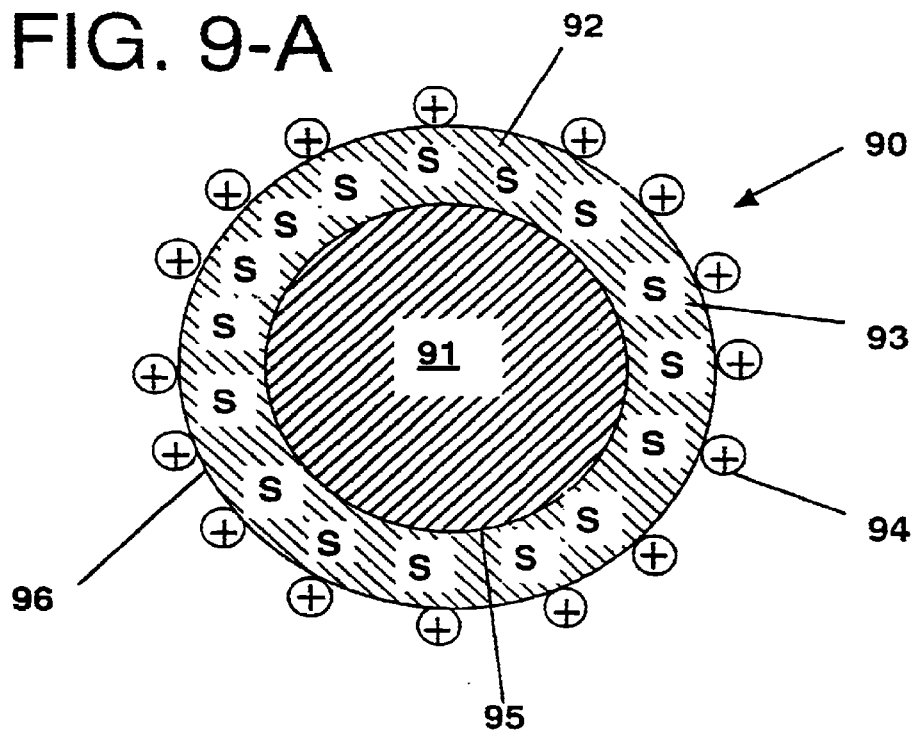
FIG. 9-A
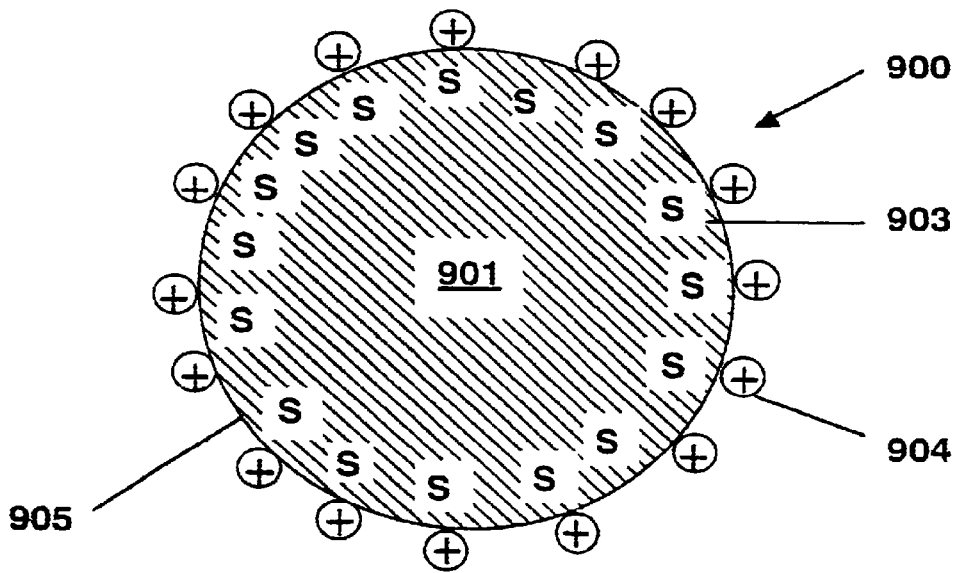
FIG. 9-B

FIG. 9-C
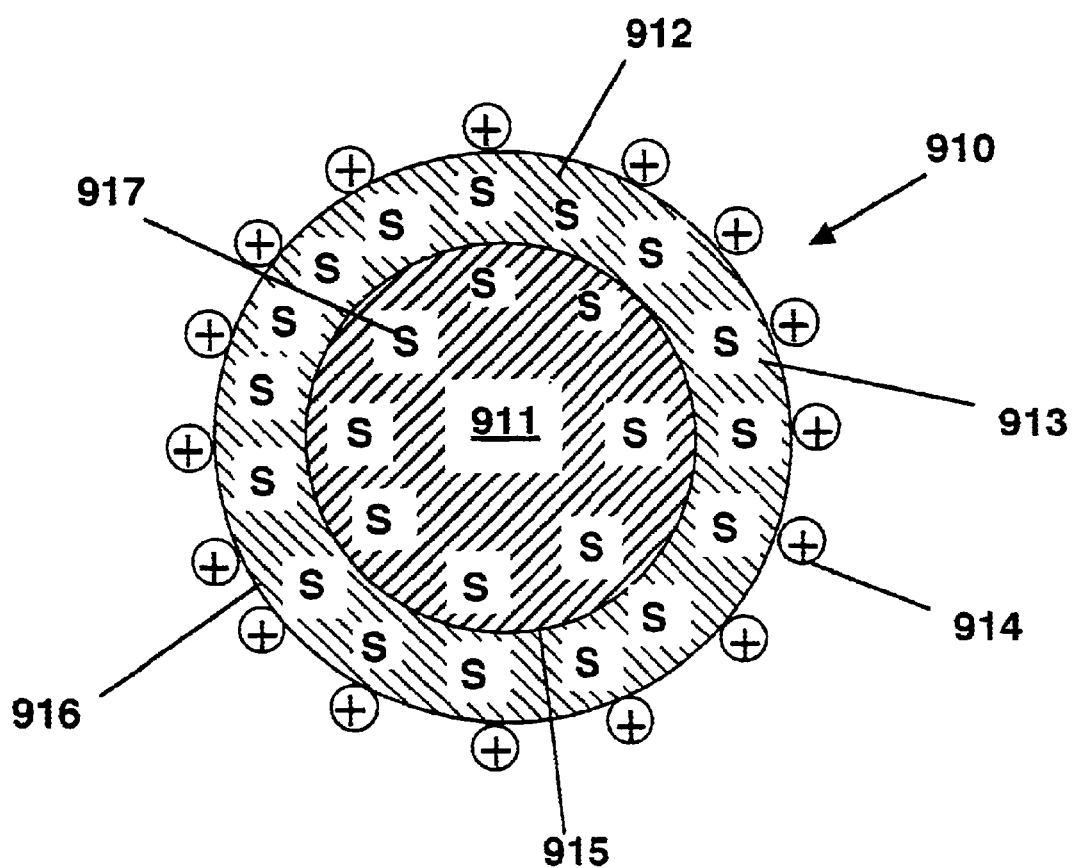

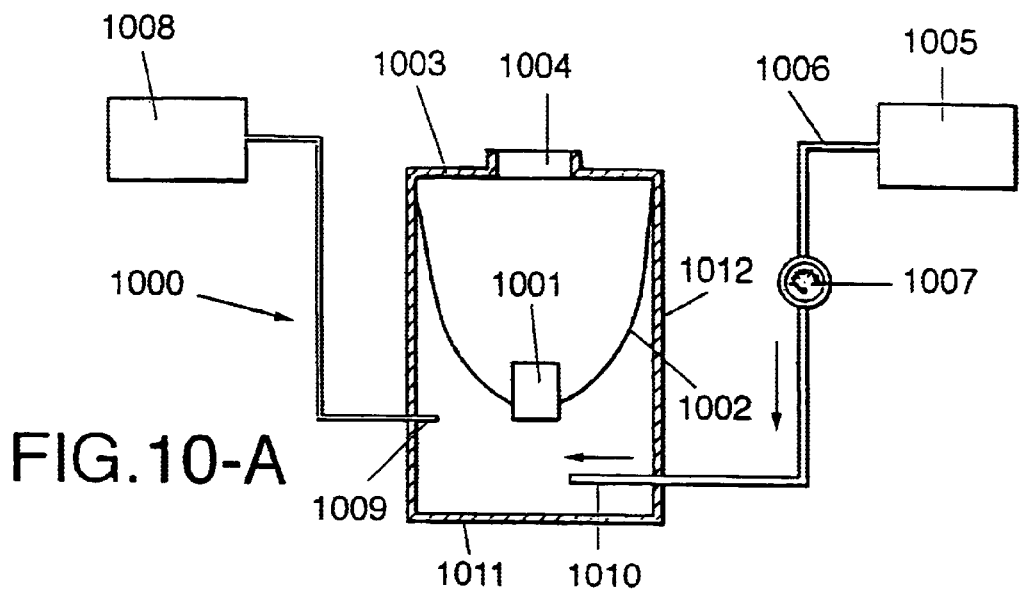
FIG. 10-A
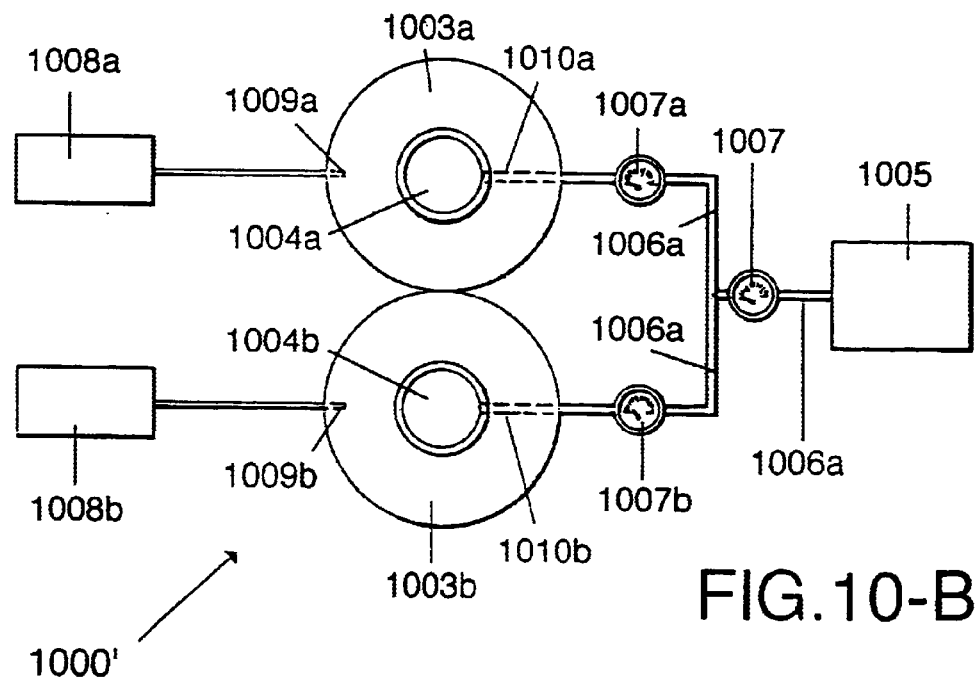
FIG. 10-B

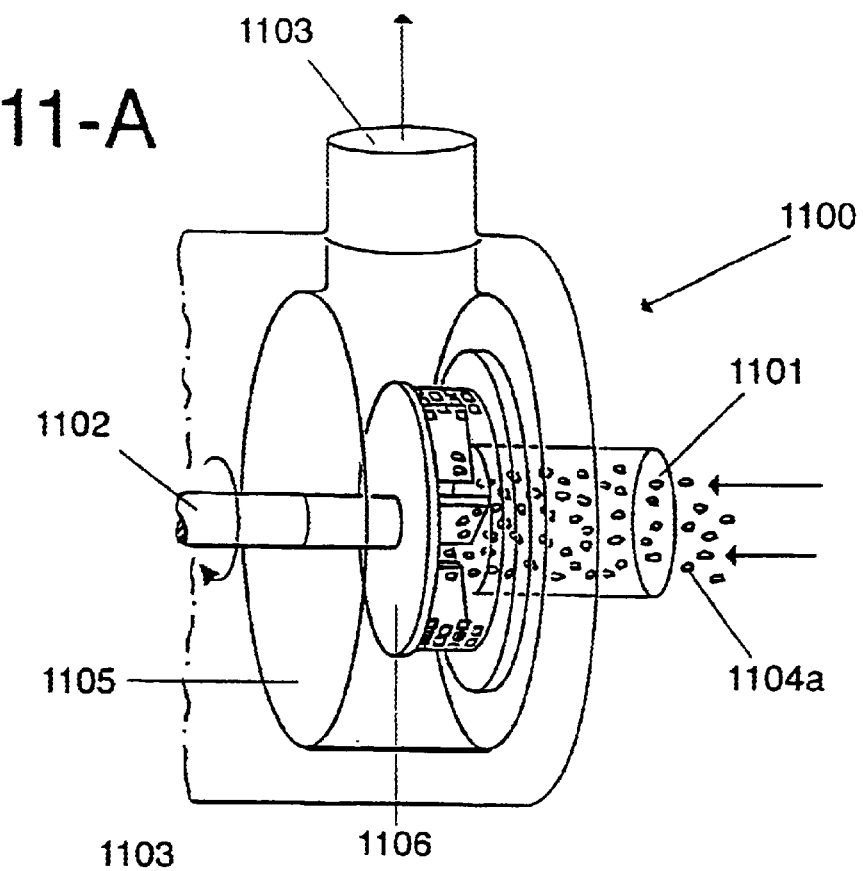
FIG.11-A
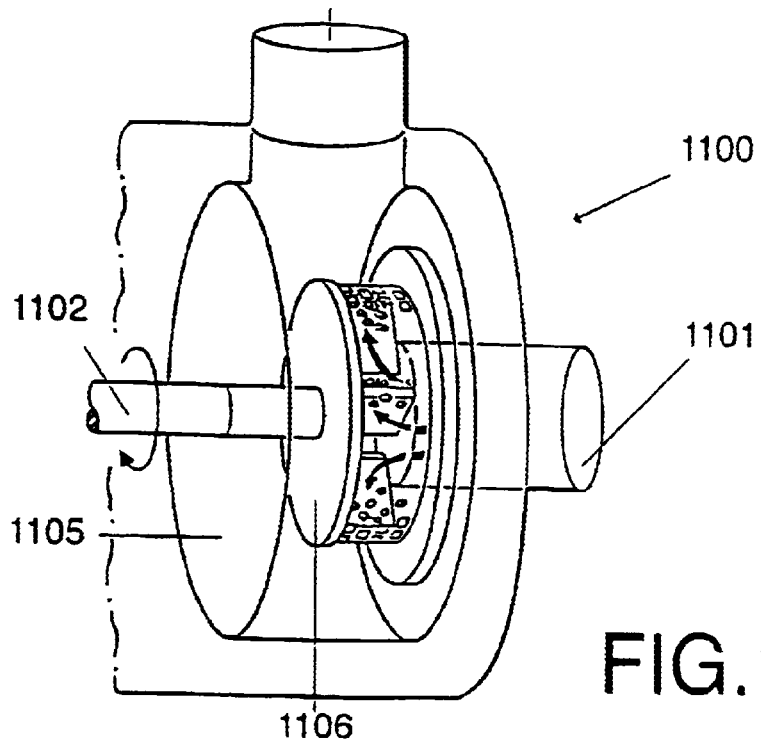
FIG.11-B

FIG. 11-C
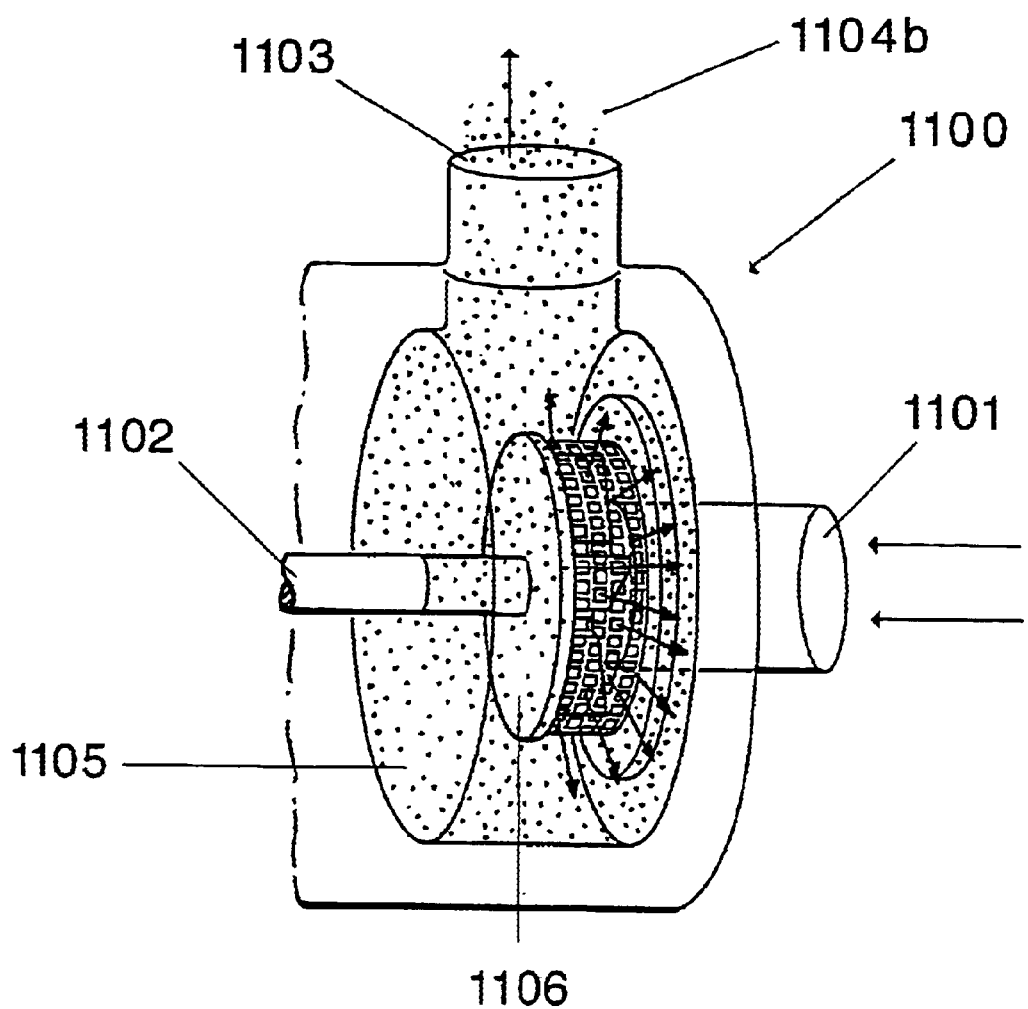

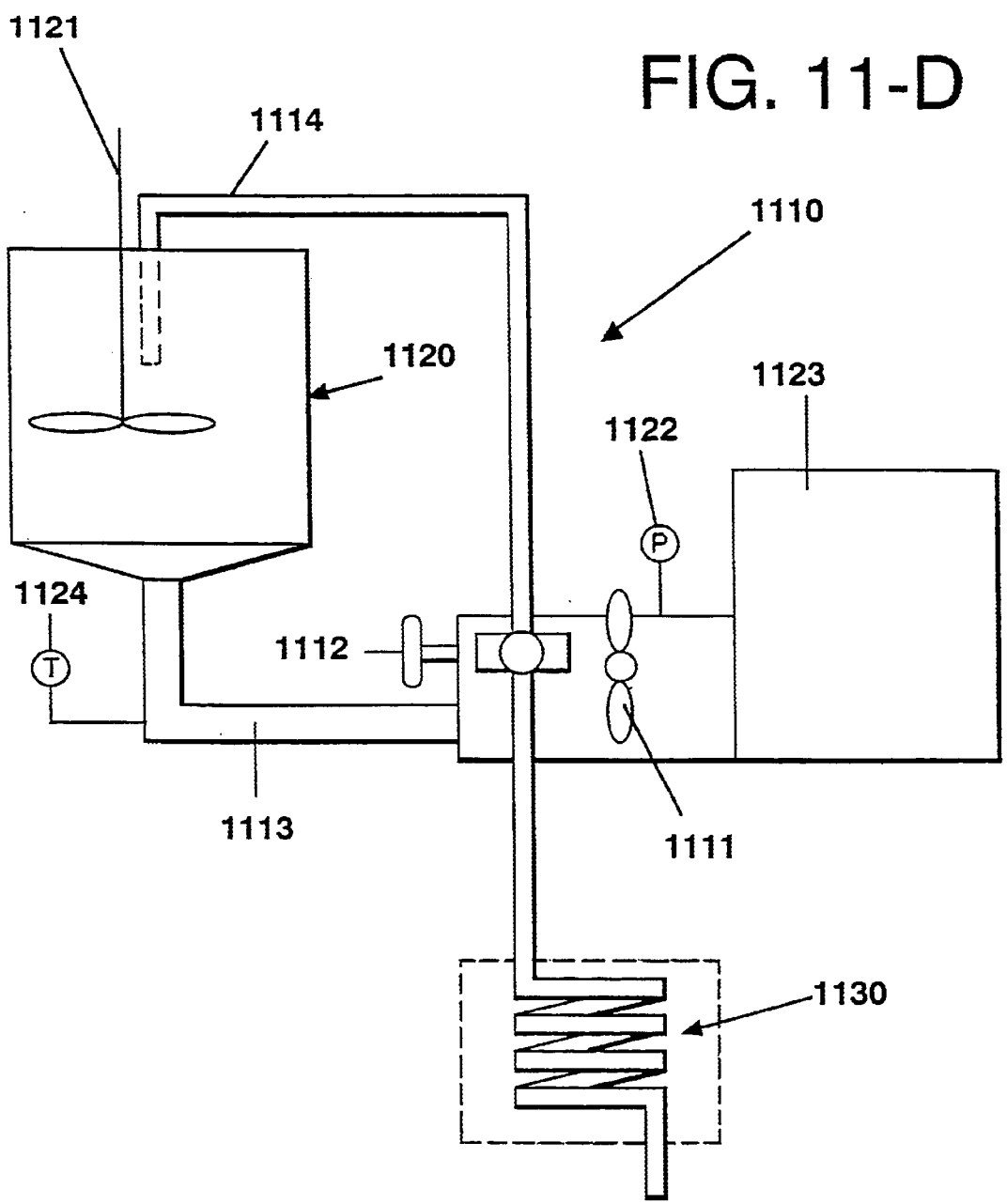
FIG. 11-D

FIG.11-E
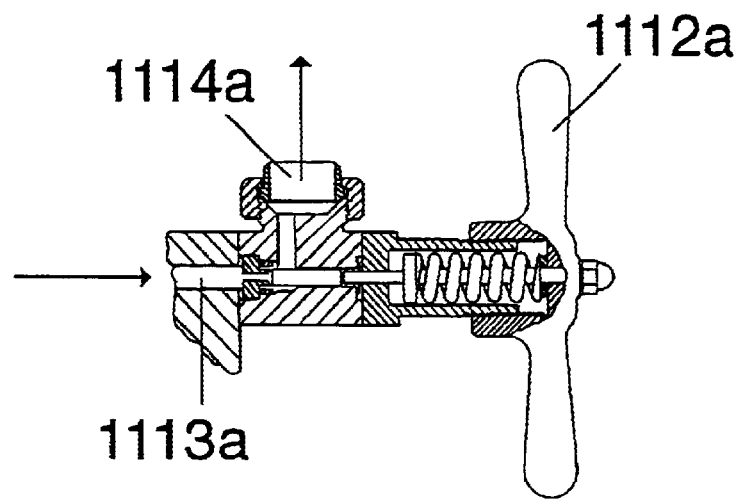
FIG.11-F
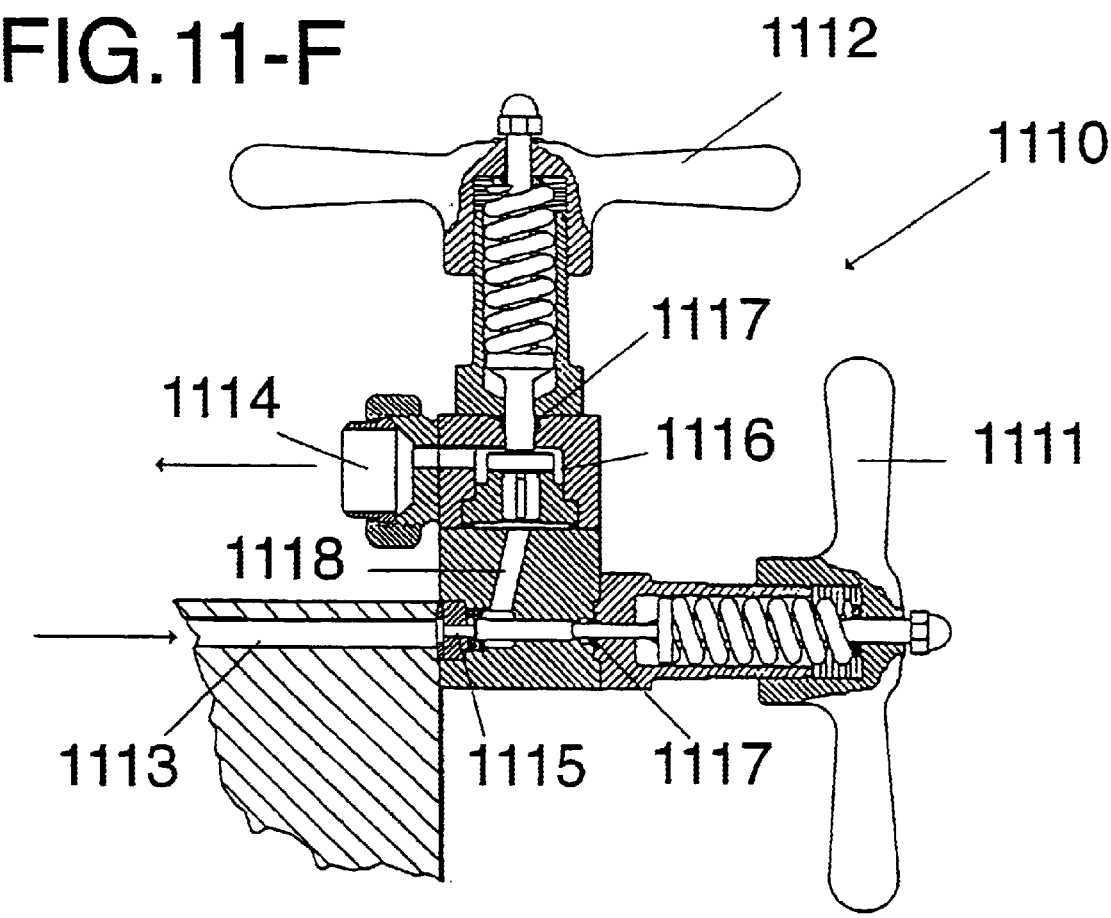

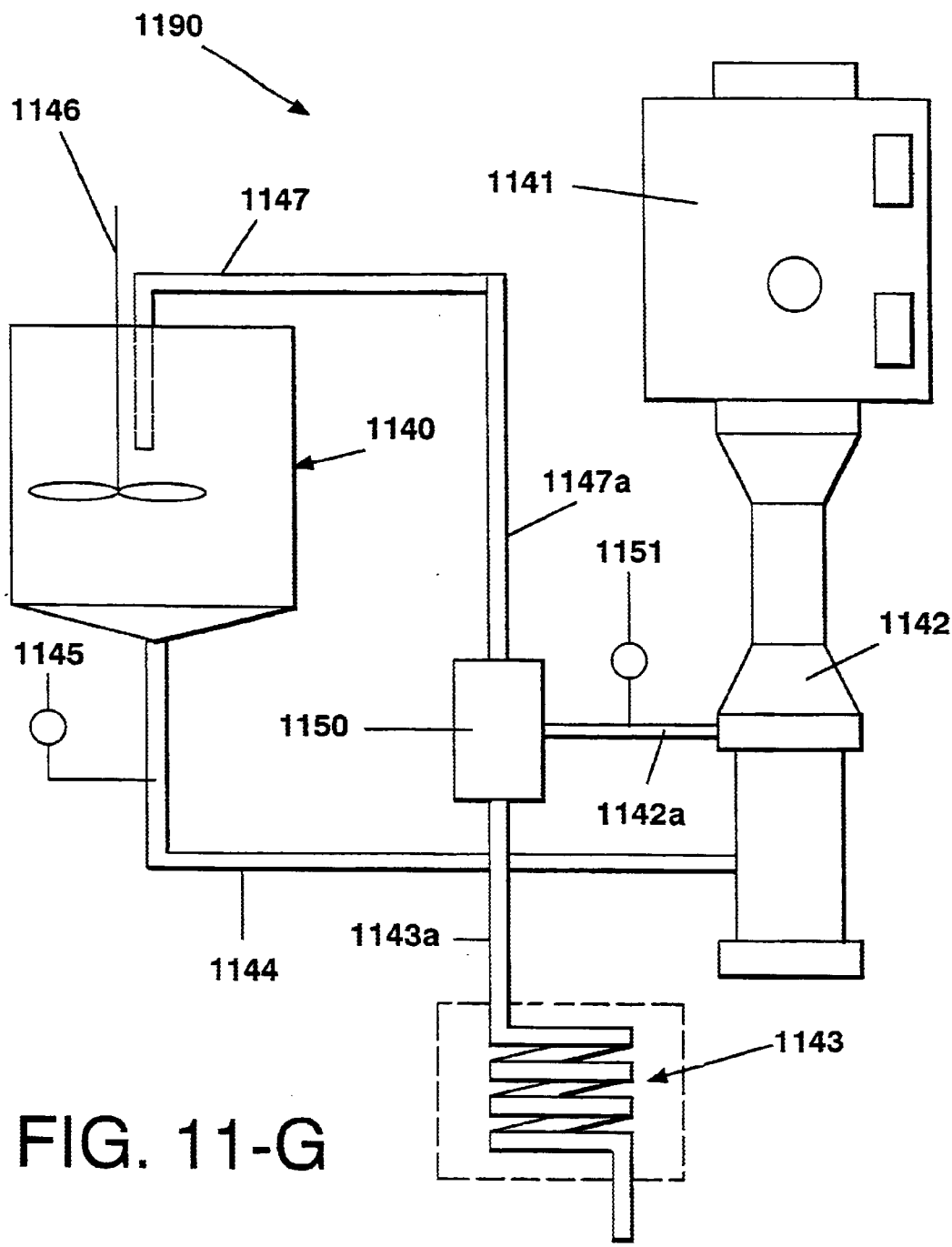
FIG. 11-G

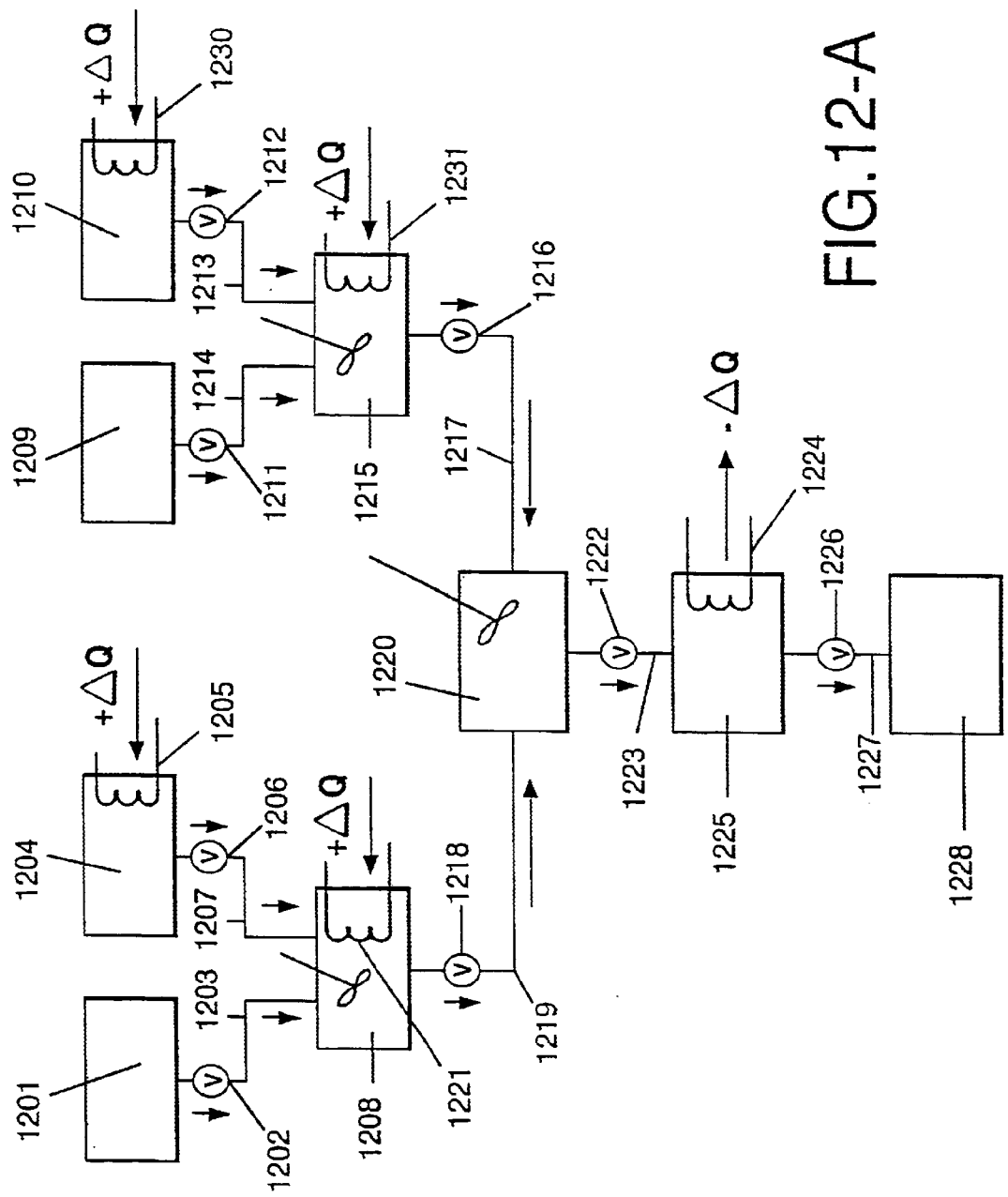
FIG.12-A

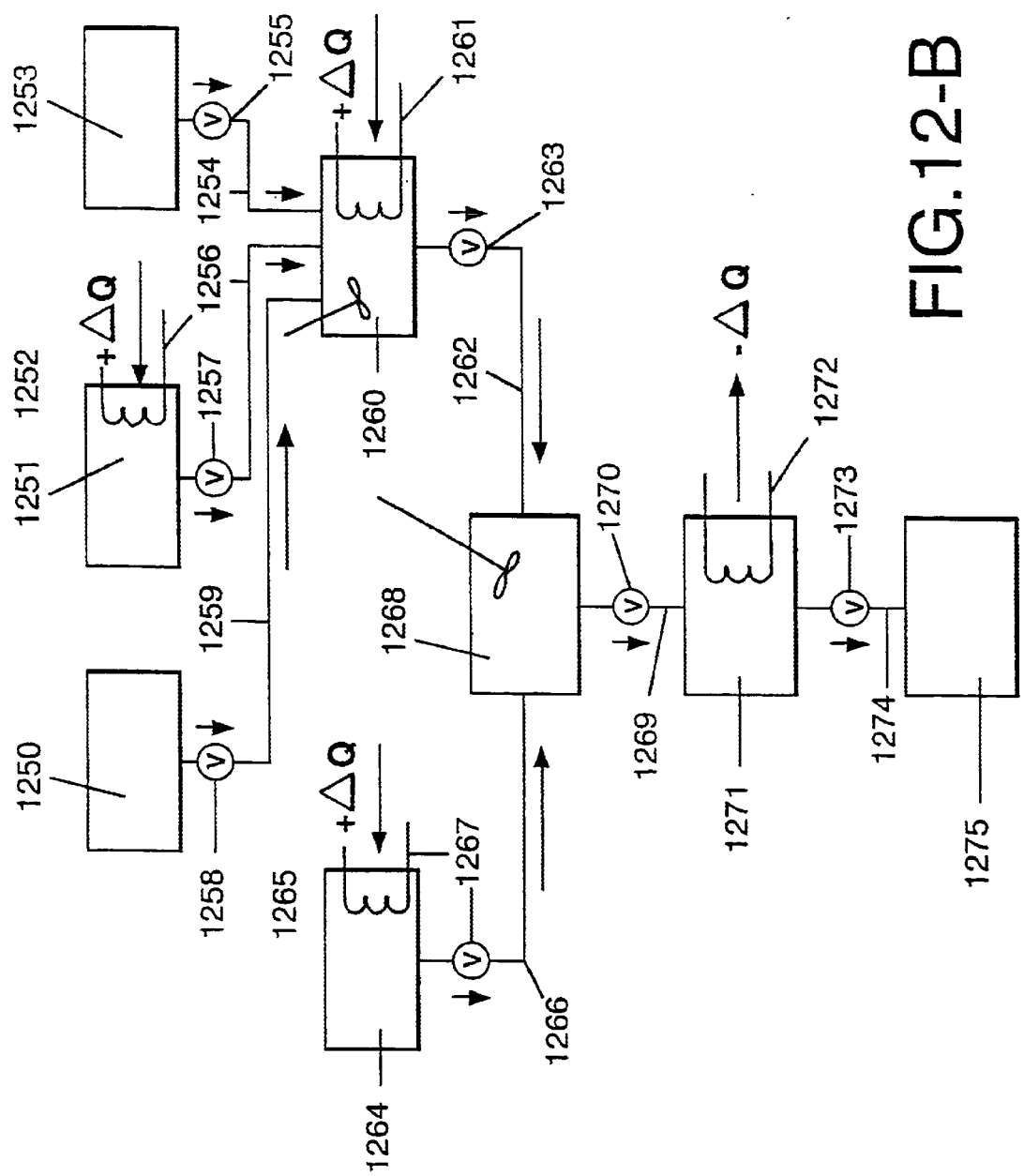
FIG.12-B

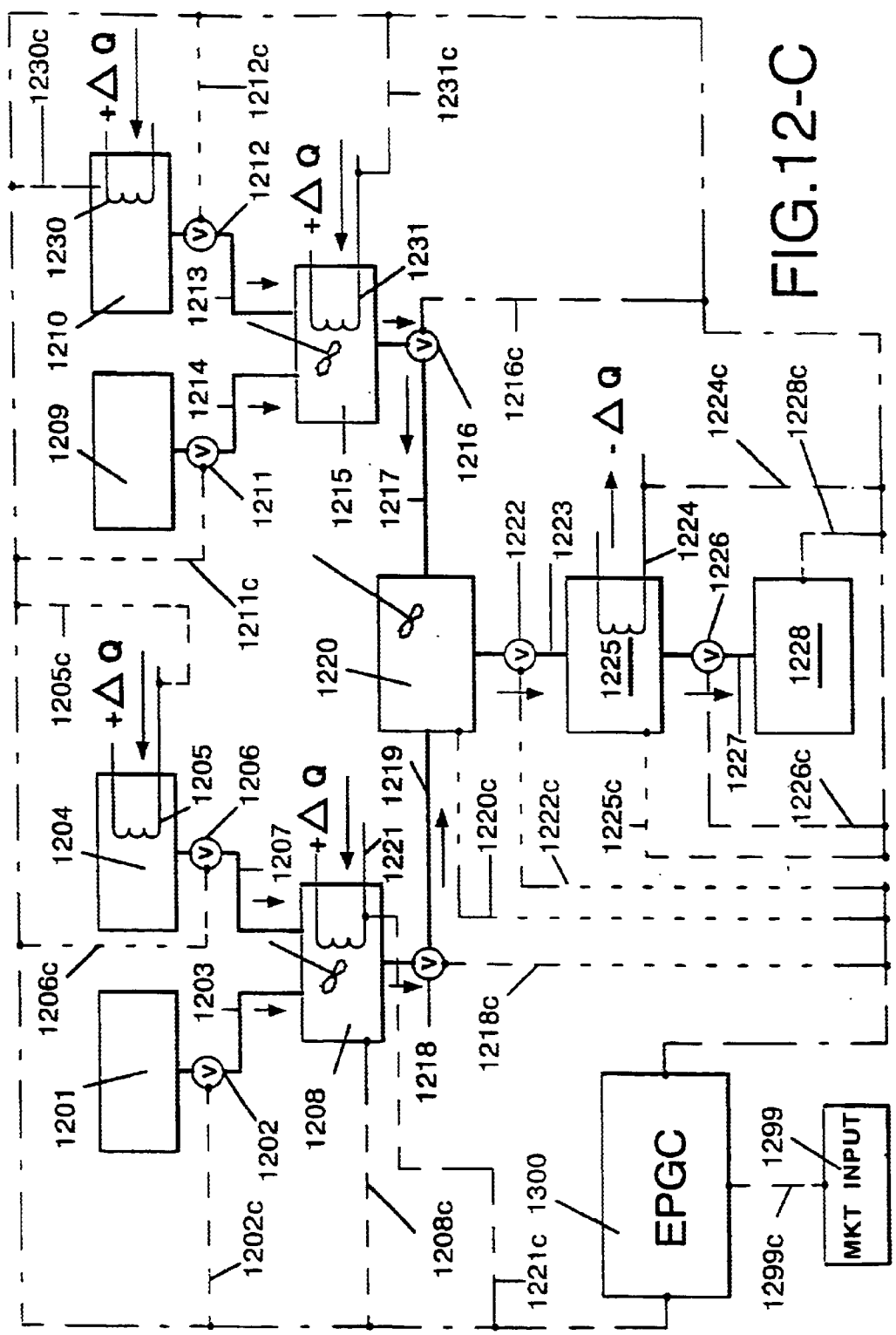

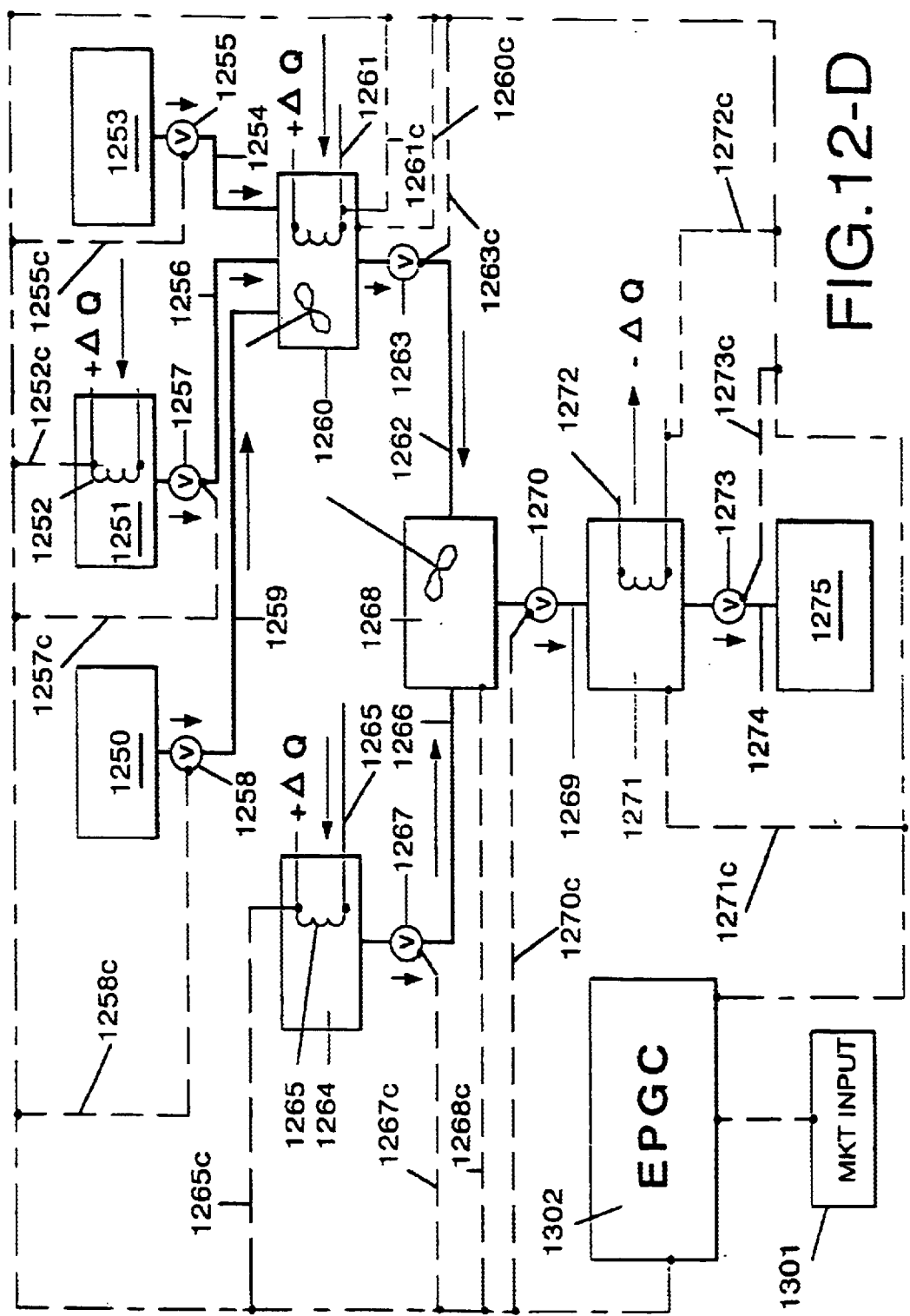

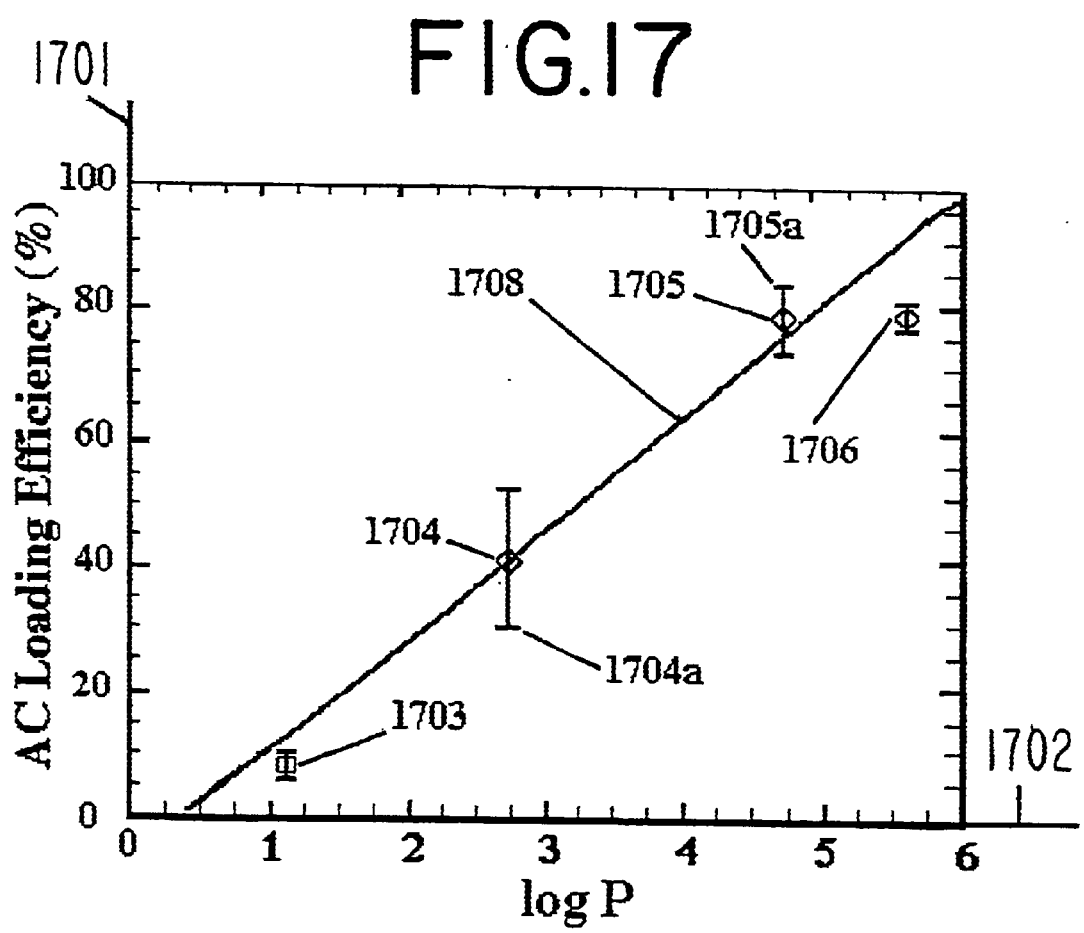

FIG.18-A
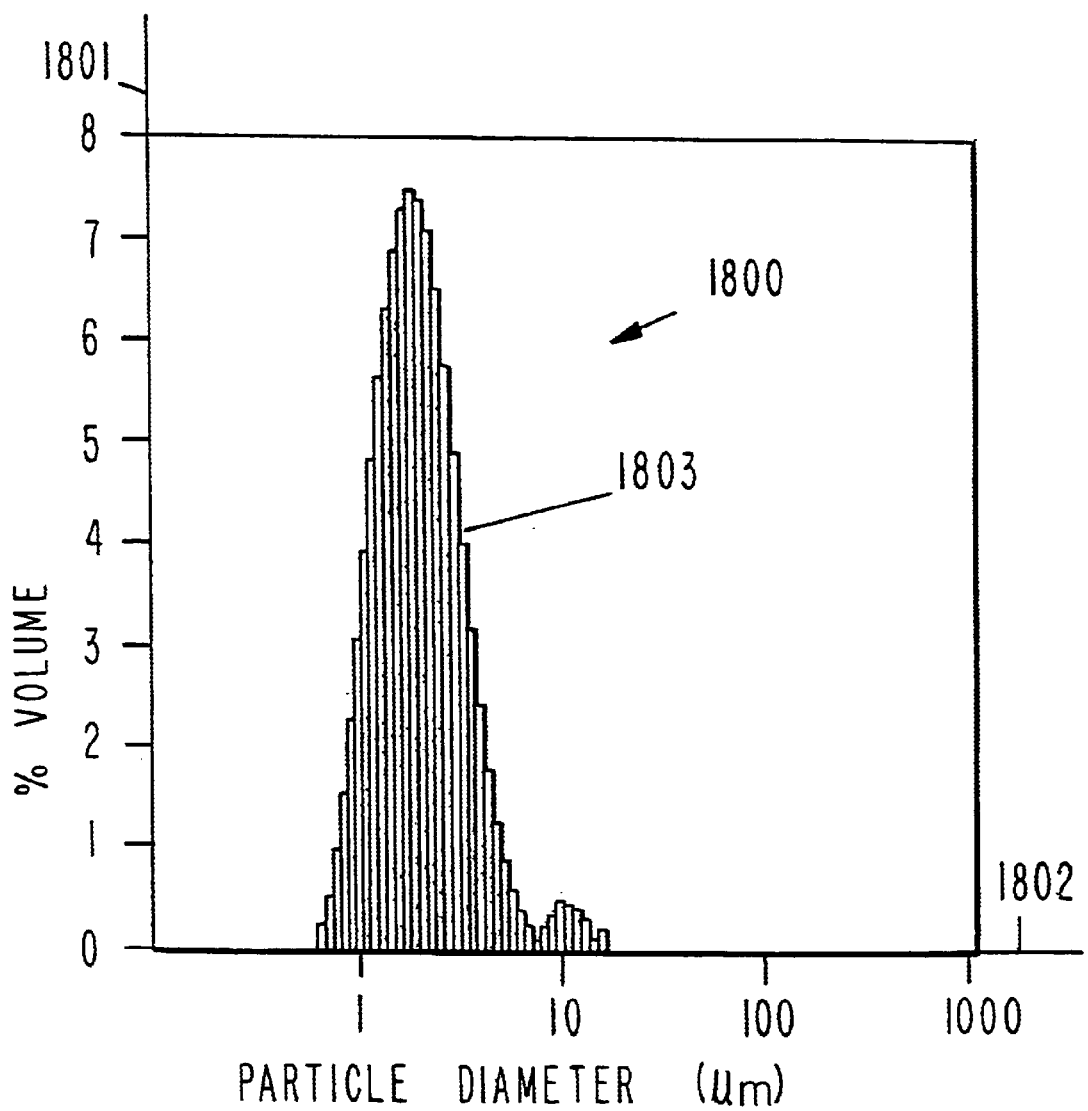

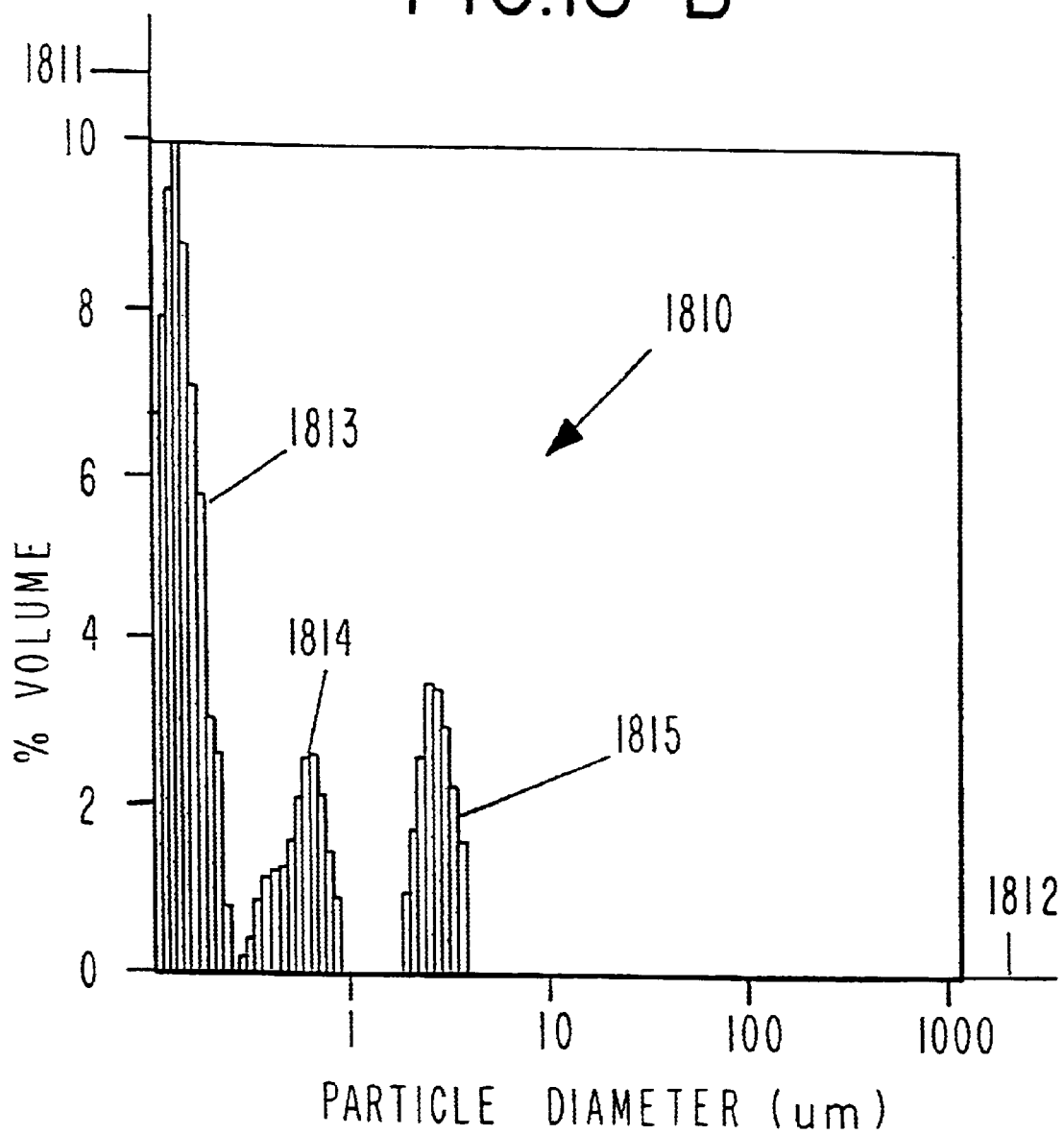

TARGETED DELIVERY OF ACTIVE/BIOACTIVE AND PERFUMING COMPOSITIONS

RELATED PENDING PATENT APPLICATIONS

This application is a Continuation of Application for U.S. patent application Ser. No. 09/208,462 filed on Dec. 10, 1998, now abandoned, which is a continuation-in-part of Application for U.S. patent application Ser. No. 08/933,599 filed on Sep. 18, 1997, now U.S. Pat. No. 6,042,792 issued on Mar. 28, 2000.

A Divisional application of said Ser. No. 08/933,599 filed on Sep. 18, 1997 now U.S. Pat. No. 6,042,792 is also in the United States Patent and Trademark Office, to wit: Ser. No. 09/064,732 filed on Apr. 23, 1998 which is now abandoned.

A second Divisional of said Ser. No. 08/933,599 filed on Sep. 18, 1997 is also in the United States Patent and Trademark Office, to wit: Ser. No. 09/130,145 filed on Aug. 6, 1998 which is now abandoned.

BACKGROUND OF THE INVENTION

Our invention relates to controlled time-release microparticulate active and bioactive compositions (including perfuming compositions) for targeted delivery to surfaces such as skin, hair and fabric and the environment proximate thereto. The active and bioactive materials contained in the microparticulate compositions of our invention have a calculated $\log_{10}P$ of between 1 and 8 (P being the n-octanol-water partition coefficient of the active and bioactive materials). Such compositions include the active or bioactive material in single phase solid solution in a wax or polymer matrix also having coated thereon and/or containing a compatible surfactant. Certain combinations of surfactants useful in the practice of our invention are novel, for the surfactants include partially hydrolyzed polyvinyl acetate. Other materials, to wit: tetra(2-hydroxypropyl) ethylenediamine having the structure:

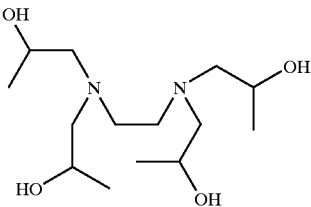

is not only useful as a surfactant, but also increases the substantivity of fragrances.

Many household products, personal products and health care products contain active and bioactive products which need to be delivered to and deposited on a target surface, i.e., fabric, skin, hair and other living tissues. Once deposited on the target surface, there is a need for the active product, i.e., a fragrance, flavor or drug, to be controllably and sustainably released over a long period of time in an efficacious manner.

Publications in the prior art indicate attempts to fulfill the foregoing needs. However, no engineered coordination of the utilization of the variables concerned has been shown in the prior art whereby, depending on the changing (as a function of time) physical and chemical properties of the surface treated and surrounding environment, the chemical and physical nature of the active and bioactive product (including diffusivities taken alone and in combination with one another in various delivery systems), the controlled time release particle composition, the controlled time release particle size range and the required rate of controlled time release of the active and bioactive product to the surface and environment surrounding the active or bioactive product delivery composition, the delivery system is shown to be capable of being optimally designed and easily and commercially manufactured.

Young, U.S. Pat. No. 4,152,272 issued on May 1, 1979 discloses fabric conditioning compositions containing particles of size 0.1 to 200 microns and of melting point 38° C. to 150° C. and comprising a wax-like carrier substance and a perfume. The particles are distributed throughout a composition, especially an aqueous fabric softening composition which contains a fabric-substantive cationic surfactant. An example of the cationic surfactant of Young is cetyl trimethyl ammonium bromide cited at column 6, lines 23 and 24. Young, however, shows formation of wax/perfume particles using, for example, a colloid mill as is shown at column 8, lines 60–65.

Domb, U.S. Pat. No. 5,188,837 issued on Feb. 23, 1993 discloses a microsuspension system and method for its preparation. The microsuspension contains liposheres which are solid, water-insoluble microparticles that have a layer of a phospholipid embedded on their surface. The core of the liposphere is a solid substance to be delivered or a substance to be delivered that is dispersed in an inert solid vehicle such as a wax.

Trinh, et al, U.S. Pat. No. 5,540,853 issued on Jul. 30, 1996 discloses a personal cleansing composition comprising:

(a) from about 0.001% up to about 10% by weight of an enduring perfume composition having at least about 70% components with a calculated $\log_{10}P \geq 3$ and a boiling point of $\geq 250°$ C.;

(b) from about 0.01% up to about 95% by weight of a surfactant system; and (c) the balance comprising carrier wherein the pH is from about 4 up to about 11. Trinh, et al, however, does not disclose a particulate control time release delivery system containing active, bioactive or perfuming materials which have a calculated $\log_{10}P$ in the range of from 1 up to about 8. The disclosure of Trinh, et al, U.S. Pat. No. 5,540,853 is incorporated by reference herein.

Somasundaran, et al, U.S. Pat. No. 5,476,660 issued on Dec. 19, 1995 discloses compositions to deposit an active substance on a target surface. The active substance is left on the surface after the product is rinsed off the surface. The preferred deposition is from compositions containing an anionic or nonionic active in the co-presence of an anionic surfactant. The compositions contain carrier particles having a zwitterionic or cationic surface and a plurality of outwardly protruding filaments containing charged organocarbyl groups. The active substance is contained within the carrier particles. Examples of target surfaces are mammalian skin, hair or nails.

Bacon, et al, U.S. Pat. No. 5,652,206 issued on Jul. 29, 1997 discloses a rinse-added fabric softening composition selected from the group consisting of:

I. a solid particulate composition comprising:

(A) from about 50% to about 95% of biodegradable cationic quaternary ammonium fabric softening compound;

(B) from about 0.01% to about 15% of an enduring perfume comprising at least 70% of enduring perfume ingredients selected from the group consisting of: ingredients having a boiling point of at least about 250°

C. and a ClogP of at least about 3, wherein ClogP is the calculated octanol/water partitioning coefficient as the logarithm to the base 10.logP, said ingredients having a boiling point of at least 250° C. and a ClogP of at least about 3 being less than 70% by weight of said enduring perfume so that a perfume with only ingredients having a boiling point of at least about 250° C. and a ClogP of at least about 3 will not be an enduring perfume; cis-jasmone; dimethyl benzyl carbinyl acetate; ethyl vanillin; geranyl acetate; α-ionone; β-ionone; γ-ionone; KOAVONE®; lauric aldehyde; methyl dihydrojasmonate; methyl nonyl acetaldehyde; γ-nonalactone; phenoxy ethyl iso-butyrate; phenyl ethyl dimethyl carbinol; phenyl ethyl dimethyl carbinyl acetate; α-methyl-4-(2-methylpropyl)-benzenepropanal; 6-acetyl-1,1,3,4,4,6-hexamethyl tetrahydronaphthalene; undecylenic aldehyde; vanillin; 2,5,5-trimethyl-2-pentyl-cyclopentanone; 2-tert-butylcyclohexanol; verdox; para-tert-butylcyclohexyl acetate; and mixtures thereof;

(C) optionally, from about 0% to about 30% of dispersibility modifier; and (D) optionally, from about 0% to about 15% of a pH modifier; and II. a liquid composition comprising:

(A) from about 0.5% to about 80% of biodegradable cationic fabric softening compound;

(B) from about 0.01% to about 10% of an enduring perfume comprising at least 70% of enduring perfume ingredients selected from the group consisting of: ingredients having a boiling point of at least about 250° C. and a ClogP of at least 3, said ingredients having a boiling point of at least about 250° C. and a ClogP of at least about 3 being less than 70% by weight of said enduring perfume so that a perfume with only ingredients having a boiling point of at least about 250° C. and a ClogP of at least about 3 will not be an enduring perfume; cis-jasmone; dimethyl benzyl carbinyl acetate; ethyl vanillin; geranyl acetate; α-ionone; β-ionone; γ-ionone; KOAVONE®; lauric aldehyde; methyl dihydrojasmonate; methyl nonyl acetaldehyde; γ-nonalactone; phenoxy ethyl iso-butyrate; phenyl ethyl dimethyl carbinol; phenyl ethyl dimethyl carbinyl acetate; α-methyl-4-(2-methylpropyl)-benzenepropanal; 6-acetyl-1,1,3,4,4,6-hexamethyl tetrahydronaphthalene; undecylenic aldehyde; vanillin; 2,5,5-trimethyl-2-pentyl-cyclopentanone; 2-tert-butylcyclohexanol; verdox; para-tert-butylcyclohexyl acetate; and mixtures thereof;

(C) optionally, from about 0% to about 30% of dispersibility modifier; and (D) the balance comprising a liquid carrier selected from the group consisting of water, $C_{1-4}$ monohydric alcohol; $C_{2-6}$ polyhydric alcohol; propylene carbonate; liquid polyethylene glycols; and mixtures thereof;

and wherein the dispersibility modifier affects the viscosity, dispersibility or both.

The Bacon, et al reference does not disclose or infer the control time release system of our invention wherein the particles, each consisting of a solid solution of a hydrophobic polymer and/or a hydrophobic wax contain and deliver active, bioactive or fragrance materials to a solid surface and to the environment surrounding same which active, bioactive and perfuming materials have a calculated $\log_{10}P$ in the range of from 1 up to about 8.

Kamel, et al, U.S. Pat. No. 4,919,841 issued on Apr. 24, 1990 discloses a process for preparing encapsulated active particles by the steps of: dispersing active materials in molten wax; emulsifying the active/wax dispersion in an aqueous surfactant solution for no longer than 4 minutes; quenching the capsules by cooling; and retrieving solidified capsules. Examples of active materials are fragrances. Kamel, et al, however, does not show the specific formation of single phase solid solutions of matrix materials containing at least one hydrophobic polymer and/or at least one hydrophobic wax having dissolved therein at least one hydrophobic fragrance material controllably time releasable therefrom and having a calculated $\log_{10}P$ in the range of from about 1 up to about 8.

Henkel (Wahle, et al), PCT Published Application No. 95/11936 published on Oct. 20, 1994 discloses finely dispersed wax dispersions with a long shelf life which can be obtained by heating: (A) 10 to 80 weight percent of a wax with (B) 0.5 to 30 weight percent of a hydrophilic nonionic dispersant with an HLB value of 8 to 18 and (C) 1 to 30 weight percent of a hydrophobic co-dispersant from the group of fatty alcohols with 12–22 carbon atoms or the partial esters of polyols with 3–6 carbon atoms with fatty acids with 12–22 carbon atoms, and then heating the dispersion obtained to a temperature within or above the phase inversion point or producing a dispersion directly at this temperature and subsequently cooling the dispersion to a temperature below the phase inversion range. PCT Application No. 95/11936 does not, however, disclose the particulate composition of our invention containing a single phase solid solution of a hydrophobic polymer and/or a hydrophobic wax having dissolved therein at least one hydrophobic fragrance material, capable of delivering the fragrance material to a surface and to the environment surrounding the particulate composition and wherein the fragrance has a $\log_{10}P$ of between about 1 and about 8.

Donbrow, *Microcapsules and Nanoparticles in Medicine and Pharmacy*, Chapter 6, "NANOPARTICLES—PREPARATION AND APPLICATIONS", Jorg Kreuter (pages 126–148), CRC Press, 1992, discloses the production of nanoparticles containing bioactive materials by means of emulsion polymerization. The Donbrow reference does not explicitly or implicitly disclose the novel process for preparing the novel compositions of matter of our invention.

Adeyeye et al, "Development and Evaluation of Sustained-Release Ibuprofen Wax Microspheres. I. Effect of Formulation Variables on Physical Characteristics", *Pharm. Res.* (1991), Volume 8, No. 11, pages 1377–1383, discloses the use of a congealable disperse phase encapsulation method for preparing sustained-release ibuprofen-wax microspheres. The microspheres are prepared with paraffin wax such as ceresine and mycrocrystalline waxes using polyvinylpyrrolidone as a dispersant and using stearyl alcohol as a wax modifier. Adeyeye, et al does not infer or disclose the microparticulate compositions of matter of our invention containing active or bioactive materials having a calculated $\log_{10}P$ in the range of from 1 up to about 8.

Thus, nothing in the prior art discloses compositions for effecting the targeted delivery of bioactive or active substances to substantially solid surfaces wherein a substance comprises at least one substantially ellipsoidal hydrophobic particle consisting essentially of a single phase solid solution of a hydrophobic polymer or a hydrophobic wax having dissolved therein at least one active or bioactive material and having proximate to substantially the entirety of its outer surface a substantially hydrophilic surfactant wherein the calculated $\log_{10}P$ of the active or bioactive substance is in the range of from about 1 up to about 8.

THE INVENTION

Our invention concerns controlled time-release microparticulate active and bioactive compositions (including perfuming compositions) for targeted delivery to surfaces such as skin, hair and fabric and the environment proximate thereto, where the active and bioactive materials have a calculated $\log_{10}P$ of between 1 and 8 (P being the n-octanol-water partition coefficient). Such compositions include the active or bioactive material in single phase solid solution in a wax or polymer matrix also having coated thereon and/or containing a compatible surfactant. Our invention is also directed to processes and apparatus for preparing such compositions and processes for using same. Furthermore, certain component(s) of the above-mentioned compositions in combination with one another are novel; both combinations containing partially hydrolyzed polyvinyl acetate having a degree of hydrolysis of between about 73% up to about 99% and having a molecular weight in the range of from about 5,000 up to about 67,000. Our invention is also directed to novel compositions having high perfume substantivity including the compound: tetra(2-hydroxypropyl) ethylenediamine having the structure:

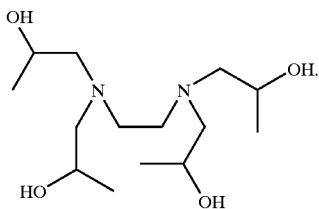

More particularly, our invention is directed to a composition for effecting the targeted delivery of a bioactive or active substance to a substantially solid surface comprising at least one substantially ellipsoidal hydrophilic particle having a continuous outer surface and an internal matrix volume consisting essentially of:

(i) a single phase solid solution of a matrix material which is in the alternative at least one of a hydrophobic polymer and/or at least one hydrophobic wax, each of which polymer and wax has a melting point in the range of from about 35° C. up to about 120° C. at 1 atmosphere pressure, having dissolved therein at least one active or bioactive substance (for example, a fragrance material) which is hydrophobic, said solid solution having an outer surface and an internal matrix volume; and (ii) proximate to substantially the entirety of said outer surface a substantially hydrophilic surfactant.

The active or bioactive material, such as a fragrance material, having a calculated $\log_{10}P$ in the range of from about 1 up to about 8 wherein P is the partition coefficient of the active or bioactive material between n-octanol and water; with the hydrophobic particle having an outside diameter in the range of from about 0.50 up to about 20 microns; the concentration of active or bioactive material in the polymer or the wax being from about 5% up to about 60% by weight of the particle; the weight percent of the surfactant being from about 0.01% up to about 5% by weight of the particle; with the wax, the surfactant and the polymer each being nonreactive with the bioactive or active material and one another.

A preferred composition of our invention is one where the permeation rate of the active or bioactive material, such as the fragrance material, through the wax or the polymer is in the range of from about $$10^{-8} \frac{\text{mg} - \text{mm}}{\text{cm}^2 - \text{min}}$$

up to about $$8 \times 10^{-3} \frac{\text{mg} - \text{mm}}{\text{cm}^2 - \text{min}}$$

as determined by the IFF permeation test as more fully described herein in the "DETAILED DESCRIPTION OF THE DRAWINGS" section, infra.

As stated, supra, proximate to substantially the entirety of the outer surface of the substantially ellipsoidal hydrophobic particle is a substantially hydrophilic surfactant. More specifically, the following three cases exist concerning the location of the surfactant:

(a) the substantially hydrophilic surfactant may be substantially entirely coated on and fixedly bonded to the entirety of the outer surface of the single phase solid solution in the form of a continuous submicron layer of surfactant; or (b) the substantially hydrophilic surfactant may be located proximate to and immediately, substantially beneath the entirety of the outer surface of the solid solution and substantially within the said internal matrix volume; and (c) the substantially hydrophilic surfactant is both (a) substantially, entirely coated on and fixedly bonded to the entirety of the outer surface of the single phase solid solution in the form of a continuous submicron layer of surfactant and (b) located proximate to and immediately, substantially beneath the entirety of the outer surface of the solid solution and substantially within the internal matrix volume.

With respect to the surfactant, the surfactant may be a cationic surfactant, and the particle would therefore be positively charged; the surfactant may be an anionic surfactant, and the particle would be negatively charged; the surfactant could be a nonionic surfactant, and the particle would have a neutral charge; and the surfactant is a zwitterionic surfactant, and the particle has a variable charge.

Examples of surfactants particularly preferred in the practice of our invention are as follows:

(a) the cationic modified starch, RediBOND® 5320 (trademark of the National Starch Company of Bridgewater, N.J.), in admixture with partially hydrolyzed polyvinyl acetate having a degree of hydrolysis of between about 73% up to about 99% and having a molecular weight in the range of from about 5,000 up to about 67,000;

(b) the substance tetra(2-hydroxypropyl)ethylenediamine (marketed, for example, as QUADROL® Polyol, and having the structure:

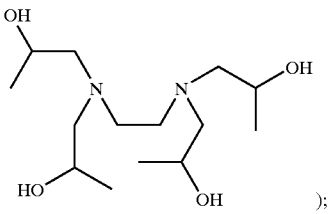

);

(c) cetyl trimethyl ammonium halide, including cetyl trimethyl ammonium chloride having the structure:

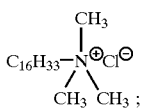

(d) a quaternary ammonium polysilane derivative having the structure:

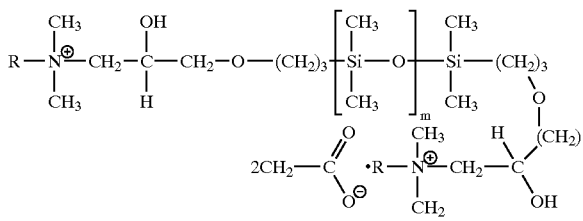

wherein R is the moiety having the structure:

wherein x is an integer of from 10 up to 100 and m is an integer of from 10 up to 100 in admixture with partially hydrolyzed polyvinyl acetate being hydrolyzed to the extent of from about 73% up to about 99% and having a molecular weight in the range of from about 5,000 up to about 67,000; and (e) the cationic polysaccharide derivative defined according to the structure:

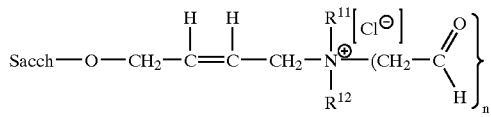

wherein n is an integer of from 1 up to 3; $R^{11}$ and $R^{12}$ are independently an alkyl, aryl, aralkyl or alkaryl group when n is 1; $R^{11}$ or $R^{12}$ is one of the groups when n is 2; or $R^{11}$ and $R^{12}$ are not present when n is 3; and wherein the moiety "SACCH" represents a starch or cellulose moiety.

The weight ratio of cationic modified starch:partially hydrolyzed polyvinyl acetate, is preferably in the range of from about 2:1 up to about 1:2, with a ratio of 1:2 being preferred. The weight ratio of the quaternary ammonium polysilane derivative:partially hydrolyzed polyvinyl acetate, is also preferably in the range of from about 2:1 up to about 1:2, with a weight ratio of 1:2 being preferred.

The mixtures of the cationic modified starch and partially hydrolyzed polyvinyl acetate as well as the quaternary ammonium polysilane derivative and partially hydrolyzed polyvinyl acetate are novel mixtures.

The matrix material which may be at least one hydrophobic polymer and/or at least one hydrophobic wax useful in the practice of our invention is preferably at least one of the following materials:

(a) polyamides having a molecular weight in the range of from about 6,000 up to about 12,000, for example, MACROMELT® 6030 manufactured by the Henkel Ag. of Dusseldorf, Germany (other examples being set forth in Lindauer, et al, U.S. Pat. No. 4,184,099 issued on Jan. 15, 1980, the specification for which is incorporated by reference herein and including the VERSA-LON® line of polyamide polymers manufactured by the Henkel Corporation of Minneapolis, Minn.);

(b) synthetic and natural carnauba wax;

(c) synthetic and natural candelilla wax;

(d) mixtures of cetyl palmitate (marketed, for example, as CUTINA® wax) with carnauba wax;

(e) mixtures of cetyl palmitate and candelilla wax;

(f) ozokerite wax;

(g) ceresin wax; and (h) low density polyethylene wax having a molecular weight in the range of from about 500 up to about 6,000.

Different combinations of waxes and surfactants are preferred for different fragrance compositions having different overall calculated $\log_{10}P$ for different applications, for example, hair care or fabric care.

The maximum vapor pressure for the active or bioactive material in the composition of our invention should be 4.1 mm/Hg at 30° C. In the event that the active material is a fragrance material, it is preferred that when the fragrance material has topnote components, middle note components and bottom note components, the vapor pressure ranges for each of these three groups of components should be as follows:

(a) with respect to the bottom note components, the vapor pressure range should be from 0.0001 mm/Hg up to 0.009 mm/Hg at 25° C.;

(b) with respect to the middle note components, the vapor pressure range of the middle note components should be from 0.01 mm/Hg up to 0.09 mm/Hg at 25° C.; and (c) with respect to the topnote components, the vapor pressure range of the bottom note components should be from 0.1 mm/Hg up to 2.0 mm/Hg at 25° C.

An example of such a fragrance as described, supra, is as follows:

| Type of Note | Component | Vapor Pressure mm/Hg at 25° C. |
|---|---|---|
| bottom note | TONALID ® (trademark of Givaudan SA of Geneva, Switzerland) | 0.0001 |
| bottom note | hexyl cinnamic aldehyde | 0.0003 |
| bottom note | cis-3-hexenyl salicylate | 0.0008 |
| bottom note | ISO E SUPER ® (trademark of International Flavors & Fragrances Inc. of New York, NY) | 0.002 |
| bottom note | peach aldehyde coeur | 0.002 |
| bottom note | LILIAL ® (trademark of Givaudan, Inc. of Clifton, NJ) | 0.003 |
| bottom note | cyclamal | 0.004 |
| bottom note | β-ionone | 0.006 |
| bottom note | γ-methyl ionone | 0.006 |
| bottom note | citronellol | 0.009 |
| bottom note | methyl nonyl acetaldehyde | 0.009 |
| middle note | allyl cyclohexyl propane | 0.01 |
| middle note | α-terpineol | 0.02 |
| middle note | l-borneol | 0.02 |
| middle note | dipropylene glycol | 0.02 |
| middle note | hyacinth extract | 0.02 |
| middle note | β-phenyl ethyl alcohol | 0.02 |
| middle note | VERTENEX ® HC (trademark of International Flavors & Fragrances Inc. of New York, NY) | 0.03 |
| middle note | linalool | 0.05 |
| middle note | allyl amyl glycolate | 0.07 |
| middle note | linalyl acetate | 0.07 |
| middle note | dihydromyrcenol | 0.09 |
| middle note | isobornyl acetate | 0.09 |
| middle note | methyl chavicol | 0.09 |
| topnote | benzyl acetate | 0.1 |
| topnote | camphor | 0.1 |
| topnote | styralyl acetate | 0.1 |
| topnote | ALDEHYDE AA Triplal ™ (trademark of International Flavors & Fragrances Inc. of New York, NY) | 0.3 |
| topnote | eucalyptus oil | 1.7 |
| topnote | cis-3-hexenyl acetate | 2.0 |

The particles of the composition of our invention may contain or have coated thereon (or both) surfactants having (i) a sufficient charge per molecule of surfactant and (ii) a sufficient concentration of surfactant in each particle so that the electrostatic charge density on the surface of each particle will be sufficient to cause adherence of the particle to a given surface, such as hair, mammalian skin or a fabric.

While using the material, tetra(2-hydroxypropyl) ethylenediamine having the structure:

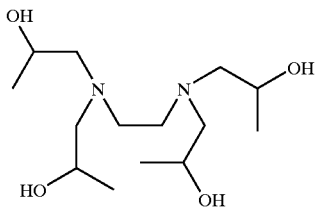

as a surfactant, we have determined that this material is also surprisingly useful in increasing substantivity of fragrances and aroma chemicals when the rate ratio of tetra(2-hydroxypropyl)ethylenediamine:fragrance material is from about 2:15 up to about 4:5. Examples of materials for which the fragrance substantivity will be increased to an extent of greater than about 50% are as follows:

(a) GALAXOLIDE®, a mixture of compounds having the structures:

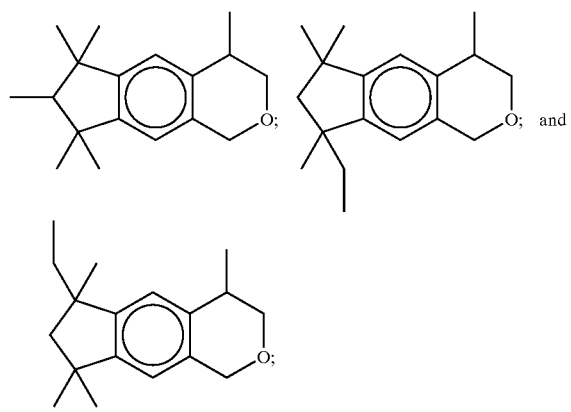

(b) geraniol having the structure:

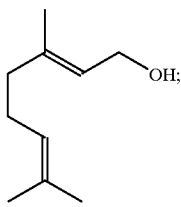

(c) β-pinene having the structure:

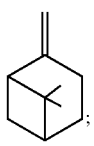

(d) n-octanal having the structure:

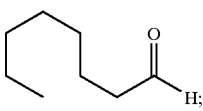

(e) dihydromyrcenol having the structure:

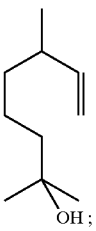

(f) KOAVONE® (trademark of International Flavors & Fragrances Inc. of New York, N.Y.) having the structure:

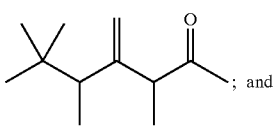

(g) eugenol having the structure:

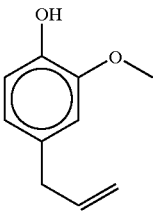

As indicated, supra, the range of permeation rates of the active and bioactive materials through the wax or polymer of the solid solution-containing particles of our invention is in the range of from about $$10^{-8} \frac{mg-mm}{cm^2-min}$$

up to about $$8 \times 10^{-3} \frac{mg-mm}{cm^2-min}.$$

Specifically, the following materials having the following calculated $\log_{10}P$ also have the following permeation rates through various waxes and polymers useful in the practice of our invention:

| Aroma Chemical | Matrix Material | Permeation Rate $\frac{\text{mg} - \text{mm thickness}}{\text{cm}^2 \text{ area} - \text{minute}}$ | Calculated $\log_{10}P$ |
|---|---|---|---|
| β-pinene | carnauba wax | $2.8 \times 10^{-4}$ | 4.6 |
| β-pinene | polyethylene wax having a molecular weight of 500 | $8.2 \times 10^{-4}$ | 4.6 |
| β-pinene | polyamide (MACROMELT ® 6030) | $2.1 \times 10^{-4}$ | 4.6 |
| ethyl tiglate having a structure: 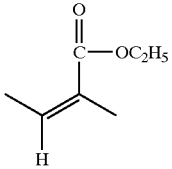 | carnauba wax | $4.4 \times 10^{-4}$ | 2.0 |
| ethyl tiglate | polyethylene wax having a molecular weight of 500 | $2.0 \times 10^{-5}$ | 2.0 |
| ethyl tiglate | polyamide (MACROMELT ® 6030) | $4.2 \times 10^{-4}$ | 2.0 |
| Fragrance mixture S-1 | carnauba wax | $5.3 \times 10^{-4}$ | — |
| Fragrance S-1 | candelilla wax | $2.7 \times 10^{-4}$ | — |
| Fragrance S-1 | polyamide (MACROMELT ® 6030) | $3.8 \times 10^{-3}$ | — |
| Fragrance S-1 | polyethylene wax (molecular weight 500) | $6.3 \times 10^{-4}$ | — |
| Fragrance O-1 | carnauba wax | $1.4 \times 10^{-3}$ | — |
| Fragrance O-1 | candelilla wax | $7 \times 10^{-4}$ | — |

In practicing our invention, the partially hydrolyzed polyvinyl acetate, also termed "polyvinyl alcohol" where the polyvinyl acetate is hydrolyzed to an extent of from about 73% up to about 99%, is prepared by means of any of Examples I–XIV of U.S. Pat. No. 5,051,222 issued on Sep. 24, 1991, the specification for which is incorporated by reference herein. Thus, the polyvinyl alcohol or the partially hydrolyzed polyvinyl acetate is prepared first by polymerizing (via a "free radical" polymerization mechanism) vinyl acetate having the formula:

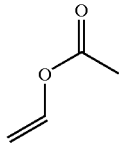

according to the reaction:

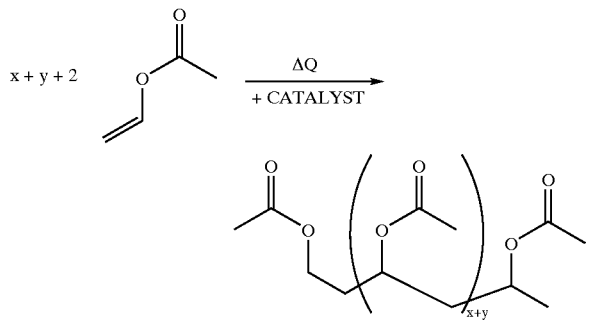

thereby forming a polyvinyl acetate wherein x+y are such that the number average molecular weight of the final product is between 5,000 and 67,000. The resulting polyvinyl acetate having the formula:

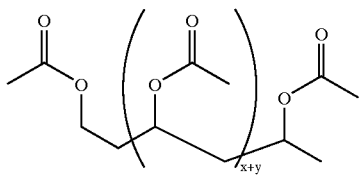

is then hydrolyzed first to form a partially hydrolyzed polyvinyl acetate according to the reaction;

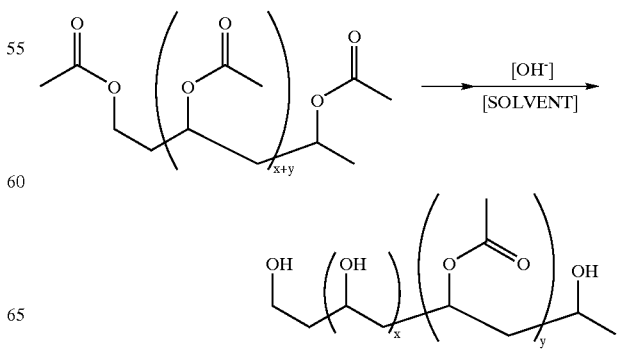

or a mixture of polyvinyl alcohol and partially hydrolyzed polyvinyl acetate according to the reaction:

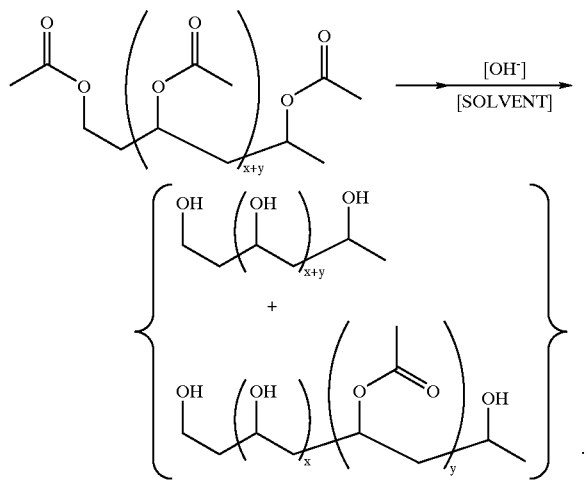

If desired, the partially hydrolyzed polyvinyl acetate may be further hydrolyzed to form polyvinyl alcohol with very few acetyl groups present (thereby forming, for example, 99% hydrolyzed polyvinyl acetate) according to the reaction:

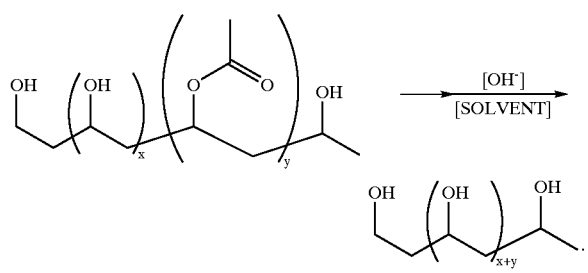

In any event, the ratio of acetyl moieties to hydroxyl moieties is less than about 1:3 in the structure:

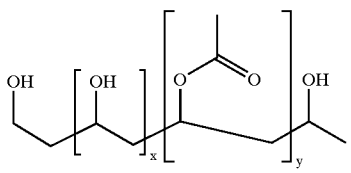

and x and y are defined whereby x+y gives rise to a polymer that has a number average molecular weight of between about 5,000 and 67,000.

When creating particles having 10% candelilla wax and 10% fragrance (making up, for example, a fabric softener containing 0.72% fragrance) using surfactants containing both hydrolyzed polyvinyl acetate (99% hydrolzyed) and either the quaternary ammonium polysilane derivatives defined according to the structure:

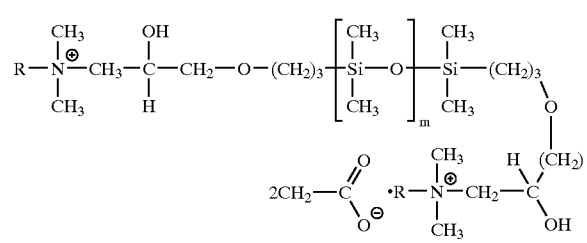

wherein R is the moiety: $CH_3-[CH_2]_x-$ and wherein m is an integer of from 10 up to 100 and wherein x is an integer of from 10 up to 100, or the cationic modified starch, RediBOND® 5320 (trademark of National Starch Inc. of Bridgewater, N.J.), the following table shows the differences in fragrance intensity on a scale of 1–10:

| Surfactant Component in Microparticle | Fragrance Intensity on a Scale of 1 to 10 |
|---|---|
| 1% quaternary ammonium polysilane derivative (SILQUAT ®) and 2% 99% hydrolyzed polyvinyl acetate | 8 |
| 1% quaternary ammonium polysilane derivative having the structure: <br><br> wherein R is the moiety: $CH_3-[CH_2]_x-$ and wherein m is an integer of from 10 up to 100 and wherein x is an integer of from 10 up to 100 and 4% 99% hydrolyzed polyvinyl acetate. | 4 |
| 1% cationic modified starch and 2% 99% hydrolyzed polyvinyl acetate. | 7 |
| 1% cationic modified starch and 4% 99% hydrolyzed polyvinyl acetate. | 6 |

Our invention is also directed to a process for fragrancing a perfumable material having a substantially solid surface, such as hair, fabric and mammalian skin, comprising the step of contacting said solid surface of said perfumable material with at least one particle as defined, supra. When carrying out this process, the intensity of fragrancing, $\Delta A$, is governed by the algorithm:

$$\Delta A = \alpha \sum_{k=1}^{P} \sum_{j=1}^{Q} \sum_{i=1}^{n} B_k M_{oj} \left( 1 - e^{\frac{-3D_j \theta^2}{2R_i^2}} \right)$$

wherein $\alpha$ is a constant, $\beta_k$ is the individual and multiple threshold values of the Q components of the fragrance material within the microparticle being controllably released (the number of threshold values is "P" since not only are individual components measured for their thresholds, but pairs and triplets of fragrance materials are measured for their thresholds also); the symbol $M_{oj}$ is the initial number of gram moles of one of Q fragrance components in the particle; $D_j$ is the diffusivity of each of Q fragrance components in the particle; $\theta$ is the time during which the particle diffusably and controllably releases the fragrance to the solid surface and environment surrounding the particle; and $R_i$ is the radius of n particles. The aroma intensity created from one particle is shown by the equation:

$$\Delta A_p = \alpha \sum_{k=1}^{P} \sum_{j=1}^{Q} B_k M_{oj} \left( 1 - e^{\frac{-3D_j \theta^2}{2R^2}} \right).$$

The aroma intensity created by n particles having an average radius $\overline{R}$ is shown by the equation:

$$\Delta A_{EST.} = \alpha n \sum_{k=1}^{P} \sum_{j=1}^{Q} M_{oj} \left( 1 - e^{\frac{-3D_j \theta^2}{2R^2}} \right).$$

The foregoing equations are derived using the differential equations:

$$\left( \frac{\partial C_j}{\partial \theta} \right) = D_j \left( \frac{\partial^2 C_j}{\partial x^2} + \frac{\partial^2 C_j}{\partial y^2} + \frac{\partial^2 C_j}{\partial z^2} \right) \text{ and } \left( \frac{\partial M_j}{\partial \theta} \right) = -\frac{D_j M_j A_j \theta}{V_i R_i}.$$

The rate of change with respect to time of the aromatization, $\Delta A$ is shown by the equation:

$$\frac{d\Delta A}{d\theta} = \sum_{k=1}^{P} \sum_{j=1}^{Q} \sum_{i=1}^{n} B_k \left\{ \frac{M_{oj} D_j \alpha}{R_i^2} \right\} \cdot \left[ 4 e^{-\frac{3}{2} \frac{D_j \theta^2}{R_i^2}} - 3 e^{\frac{-3D_j \theta^2}{R_i^2}} \right].$$

In the foregoing compositions, various grades of partially hydrolyzed and substantially fully hydrolyzed forms of hydrolyzed polyvinyl acetate can be used, to wit:

| Brand of Hydrolyzed Polyvinyl Acetate (Manufactured by Hoechst A.g., D6230 Frankfurt am Main, Germany) | Number Average Molecular Weight | % Hydrolyzed |
| --- | --- | --- |
| MOWIOL ® 10-74 (trademark of Hoechst A.g.) | 20,000 | 74 |

-continued

| Brand of Hydrolyzed Polyvinyl Acetate (Manufactured by Hoechst A.g., D6230 Frankfurt am Main, Germany) | Number Average Molecular Weight | % Hydrolyzed |
| --- | --- | --- |
| MOWIOL ® 4-80 | 24,000 | 80 |
| MOWIOL ® 3-83 | 14,000 | 83 |
| MOWIOL ® 5-88 | 37,000 | 88 |
| MOWIOL ® 8-88 | 67,000 | 88 |
| MOWIOL ® 3-98 | 16,000 | 98 |
| MOWIOL ® 4-98 | 27,000 | 98 |
| MOWIOL ® 6-98 | 47,000 | 98 |
| MOWIOL ® 10-98 | 61,000 | 98 |
| MOWIOL ® GE 4-86 | 62,000 | 86 |

Additional equations concerning the diffusion of the active or bioactive product from the particulate compositions of our invention are derived using the teachings of Peppas, et al, *Journal of Controlled Release*, Volume 40 (1996), pages 245–250 and entitled "Controlled release of fragrances from polymers I. Thermodynamic analysis" and from the text entitled *DIFFUSION IN POLYMERS* edited by P. Neogi, published 1996 by Marcel Dekker, Inc. at pages 165–169 (chapter by Duda and Zielinski entitled "FREE-VOLUME THEORY" and the subchapter entitled "Multicomponent Diffusion". Each of the foregoing references is incorporated by reference herein.

Our invention is also directed to a process for preparing hydrophobic active ingredient- or bioactive ingredient-containing compositions as defined, supra, comprising the steps of:

(i) intimately admixing at least one hydrophobic active ingredient or bioactive ingredient material with at least one hydrophobic polymer and/or at least one hydrophobic wax to form a first mixture at a temperature greater than or equal to the melting point of said polymer or said wax or, in the case of mixtures, the melting point of the highest melting polymer or wax in the mixture;

(ii) intimately admixing a surfactant (as defined, supra) with an aqueous composition comprising water (for example, a mixture of sodium chloride and water or a mixture of propylene glycol and water or water itself) to form a second mixture which is an aqueous solution (for example, a solution of sodium chloride in water or a solution of propylene glycol in water);

(iii) blending said first mixture and said second mixture at a temperature in the range of from about 60° C. up to the boiling point at atmospheric pressure of the aqueous composition (for example, water boiling at 100° C. or a mixture of water and propylene glycol boiling at 120° C.) whereby a microemulsion is formed; and (iv) causing the hydrophobic active ingredient- or bioactive ingredient (e.g., perfume)-containing composition in the solid phase to form as an aqueous suspension of solid phase particles (as by cooling to 25° C.)

wherein the weight percent of active ingredient or bioactive ingredient (e.g., fragrance composition or aroma chemical) for forming said first mixture is in the range of from about 5% up to about 60% by weight of said first mixture; wherein the weight percent of surfactant in the second mixture is from about 0.01% up to about 5% by weight of said second mixture. In fact, the cooling step, cooling the aqueous suspension, can be carried out at a temperature of from about 10° C. up to about 30° C.

The foregoing process is carried out preferably using a homogenizer and/or a rotor/stator high shear mixer.

Examples of a homogenizer useful in the practice of this aspect of our invention are laboratory homogenizer models 15MR and 31MR manufactured by APV Gaulin, Inc. of 44 Garden Street, Everett, Mass. 02149. Examples of rotor/stator high shear mixers are the high shear in-line mixers manufactured by Silverson Machines, Inc., P.O. Box 589, 355 Chestnut Street, East Long Meadow, Mass. 01028 and by the Scott Process Equipment Corporation, P.O. Box 619, Sparta, N.J. 07871. The aforementioned homogenizers and rotor/stator high shear mixers can be used in conjunction with one another, with the rotor/stator high shear mixers being used first and then in order to bring the particle size down further, the resulting emulsion is then further homogenized using the homogenizers such as laboratory homogenizers, models 15MR and 31MR.

The details of the aforementioned homogenizers and rotor/stator high shear mixers are set forth in the "DETAILED DESCRIPTION OF THE DRAWINGS" section, infra.

Our invention is also intended to cover a process for preparing the hydrophobic active or bioactive ingredient-containing compositions discussed, supra (e.g., perfume compositions), comprising the steps of:

(i) intimately admixing at least one hydrophobic active or bioactive material (e.g., perfume composition) with (a) at least one hydrophobic polymer and/or at least one hydrophobic wax and (b) at least one surfactant to form a first single liquid phase mixture at a temperature greater than or equal to the melting point of said polymer or said wax or, in the case of mixtures, the melting point of the highest melting polymer or wax in the mixture;

(ii) blending said first single liquid phase mixture with an aqueous composition comprising water (for example, water itself or a mixture of propylene glycol and water or a mixture of sodium chloride and water, for example, a 5% sodium chloride solution or a 20% aqueous propylene glycol solution) whereby a microemulsion is formed; and (iii) causing the hydrophobic active or bioactive ingredient-containing composition (e.g., a perfume-containing composition or an aroma chemical-containing composition) in the solid phase to form as an aqueous suspension of solid phase particles (for example, cooling the resulting suspension to a temperature in the range of from about 10° C. up to about 30° C.)

wherein the weight percent of active ingredient or bioactive ingredient for forming the first mixture is in the range of from about 5% up to about 60% by weight of said first mixture; and wherein the weight percent of surfactant in the first mixture is from about 0.01% up to about 5% by weight of the first mixture.

Again, as stated, supra, with respect to the first-described process for preparing hydrophobic active ingredient- or bioactive ingredient-containing compositions of our invention, the blending step is carried out using a homogenizer and/or a rotor/stator high shear mixture as described in detail, supra, and as exemplified in detail, supra, and as described in detail in the DETAILED DESCRIPTION OF THE DRAWINGS section, infra.

Our invention is also directed to apparatus for carrying out the aforementioned processes for preparing the hydrophobic active ingredient- or bioactive ingredient-containing compositions. This apparatus comprises:

(i) means for intimately admixing at least one hydrophobic active ingredient- or bioactive ingredient-containing material with at least one hydrophobic polymer or at least one hydrophobic wax to form a first single liquid phase mixture at a temperature greater than or equal to the melting point of said polymer or said wax or, in the case of mixtures, the highest melting component of the mixture;

(ii) means for intimately admixing a surfactant with an aqueous composition comprising water to form a second mixture which is an aqueous solution (for example, using a homogenizer or rotor/stator high shear mixer);

(iii) means for blending said first mixture and said second mixture at a temperature of between 60° C. and the boiling point of the aqueous composition at atmospheric pressure whereby a microemulsion is formed (for example, using the homogenizer and/or the rotor/stator high shear mixer as described, supra); and (iv) means for causing the hydrophobic active ingredient- or bioactive ingredient-containing composition in the solid phase to form as an aqueous suspension of solid phase particles (for example, using cooling means to cool the mixture to 10–30° C., for example, using apparatus equipped with cooling coils).

Additional apparatus for preparing the hydrophobic active or bioactive ingredient-containing compositions of our invention comprise:

(i) means for intimately admixing at least one hydrophobic active ingredient- or bioactive ingredient-containing composition with (a) at least one hydrophobic polymer and/or at least one hydrophobic wax and (b) at least one surfactant to form a first single liquid phase mixture at a temperature greater than or equal to the melting point of said polymer or said wax or, in the case of mixtures, the melting point of the highest melting of the materials in the mixture;

(ii) means for blending said first single liquid phase mixture with an aqueous composition comprising water whereby a microemulsion is formed (for example, using the homogenizer and/or the rotor/stator high shear mixer as described, supra); and (iii) means for causing the hydrophobic active ingredient- or bioactive ingredient-containing composition in the solid phase to form as an aqueous suspension of solid phase particles (for example, cooling coils to cool the suspension to a temperature of between 10° C. and 30° C.).

BRIEF DESCRIPTION OF THE DRAWINGS

FIG. 1A is a diagram of magnified (2,000×) cloth treated by fabric softener without the use of the microparticulate compositions of our invention.

FIG. 1A-I is a photograph (magnified 2,000×) of cloth treated by fabric softener without the use of the microparticulate composition of our invention.

FIG. 1B is a diagram of magnified fabric (2,000×) washed with wax microparticles containing fragrance of our invention.

FIG. 1B-I is a magnified photograph (2,000×) of fabric (towels) washed with encapsulated fragrance in wax microparticles of our invention.

FIG. 2A is a diagram of a magnified (2,000×) strand of hair washed with shampoo without the use of the microparticulate composition of our invention.

FIG. 2A(I) is a magnified (2,000×) photograph of a strand of hair washed with shampoo without the use of the microparticulate composition of our invention.

FIG. 2B is a diagram of a magnified (2,000×) strand of hair washed with shampoo containing encapsulated fragrance in wax microparticles of our invention.

FIG. 2B(I) is a magnified (2,000×) photograph of a strand of hair treated with shampoo and the encapsulated fragrance in wax microparticles of our invention.

FIG. 2C is a diagram of a magnified strand of hair (1,500×) washed with conditioner without the use of the microparticulate composition of our invention.

FIG. 2C(I) is a photograph (magnified 1,500×) of a strand of hair washed with conditioner but without the use of the microparticulate composition of our invention.

FIG. 2D is a diagram of a magnified (1,500×) strand of hair washed with conditioner containing the wax microparticles of our invention.

FIG. 2D(I) is a photograph of a magnified (1,500×) strand of hair washed with conditioner containing wax microparticles of our invention.

FIG. 3A is a schematic representation of a typical fabric consisting of interwoven bundles which are made up of intertwined fibers. Illustrated is a microparticle entrapped in the pores between the bundles.

FIG. 3B is a schematic representation of a typical fabric consisting of interwoven bundles which are made up of intertwined fibers showing microparticle entrapment in the pores between the bundles as well as direct adhesion through physical forces between a microparticle and a bundle. The microparticles are depicted as black dots.

FIG. 4A is a cutaway side elevation view of apparatus used to carry out the IFF permeation test in order to determine the permeability of fragrances through a given polymer in the presence or in the absence of surfactant.

FIG. 4B is a perspective view of the permeation test (diffusion cell) of FIG. 4A.

FIG. 5A is a graph indicating the permeability of candelilla wax to the aroma chemicals, ethyl tiglate having the structure:

Figure 13:
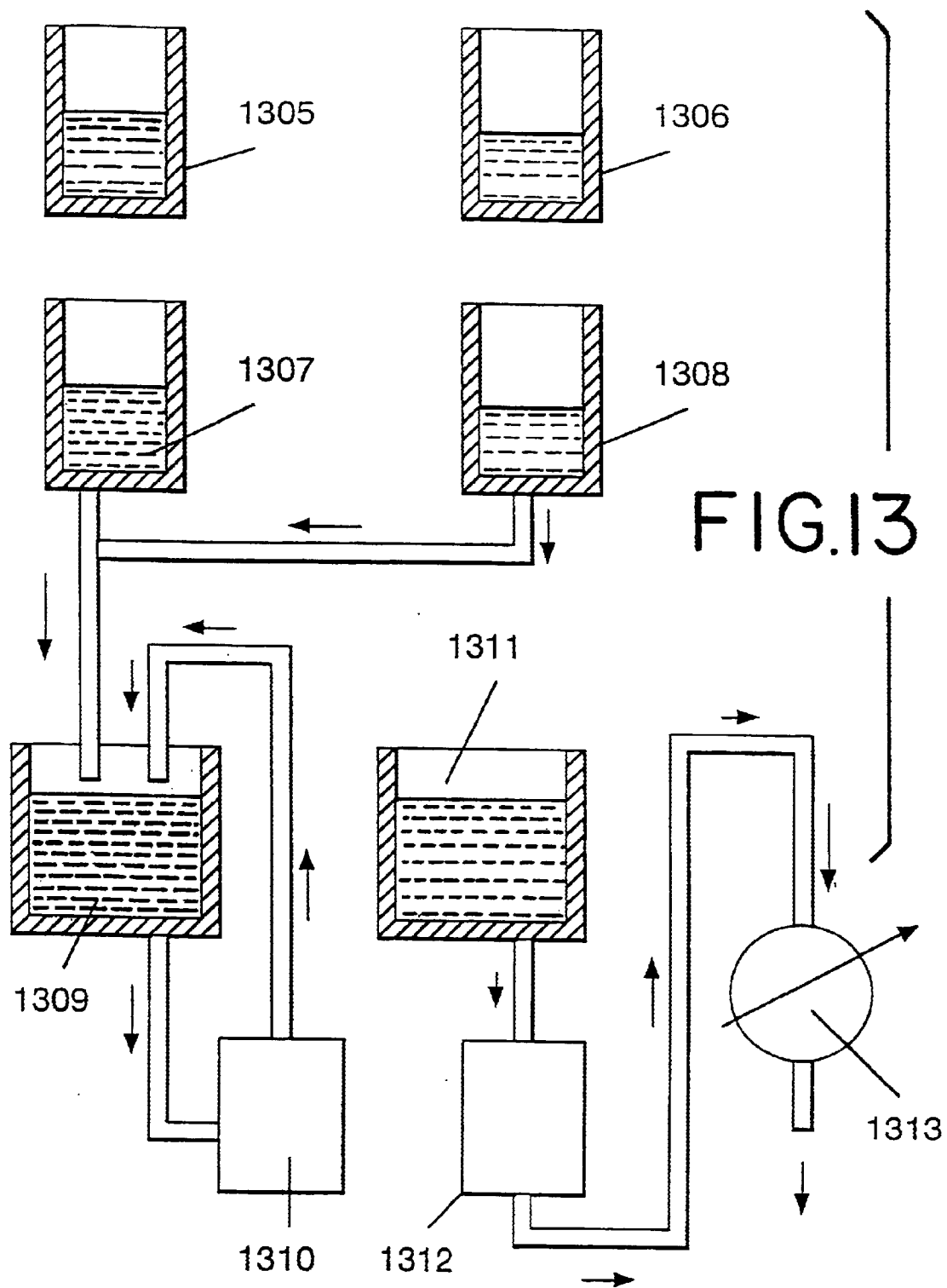

$$\begin{array}{c} CH_3 \\ | \\ CH{=}C{-}COO{-}C_2H_5, \\ | \\ CH_3 \end{array}$$

aldehyde C-8 having the structure:

and β-pinene having the structure:

FIG. 5B is another graph showing the permeability of carnauba wax to the aroma chemicals: ethyl tiglate, aldehyde C-8 and β-pinene.

FIG. 5C is another graph showing the permeability of carnauba wax to the aroma chemicals: ethyl tiglate and β-pinene, using non-entrapped ethyl tiglate and β-pinene as controls.

FIG. 5D is a graph showing the permeability of polyethylene wax (molecular weight 500) to the aroma chemicals: ethyl tiglate, aldehyde C-8 and β-pinene determined by the apparatus of FIGS. 4A and 4B.

FIG. 5E is a graph showing the permeability of β-pinene through the waxes: cetyl palmitate (CUTINA® wax), carnauba wax, polyethylene wax (molecular weight 500), candelilla wax and a control.

FIG. 5E(A) is an enlargement of that part of FIG. 5E wherein the weight loss of product tested is between about zero and about $$\frac{mg-mm}{cm^2}.$$

FIG. 5F is a graph showing the permeability of ethyl tiglate through the waxes: cetyl palmitate (CUTINA® wax), carnauba wax, polyethylene wax, candelilla wax and a control.

FIG. 5G is a graph showing the permeability of hydroxypropyl cellulose to the aroma chemicals: β-pinene and ethyl tiglate and showing the use of a control (without the use of the control release polymer or wax of our invention).

FIG. 5H is a graph showing the permeability of polyvinyl alcohol to the aroma chemicals: ethyl tiglate and β-pinene and also showing the use of a control without the use of the polyvinyl alcohol.

FIG. 6A sets forth a bar graph showing percent geraniol substantivity on cotton fabric swatches for neat geraniol and for geraniol encapsulated in candelilla wax microparticles. The substantivity is plotted on a logarithmic scale.

FIG. 6B sets forth geraniol substantivity on polyester fabric swatches for neat geraniol and for geraniol encapsulated in candelilla wax microparticles. The substantivity is plotted on a logarithmic scale.

FIG. 6C sets forth the substantivity of GALAXOLIDE® (trademark of International Flavors & Fragrances Inc. of New York, N.Y.), a mixture of compounds having the structures:

on cotton swatches for the neat GALAXOLIDE® and for GALAXOLIDE® encapsulated in candelilla wax particles.

FIG. 6D sets forth the substantivity of GALAXOLIDE® on polyester fabric swatches for the neat GALAXOLIDE® and for GALAXOLIDE® encapsulated in candelilla wax microparticles.

FIG. 7A is a graph showing the sustained release of GALAXOLIDE® over two days as the neat aroma chemical and when encapsulated in candelilla wax microparticles.

FIG. 7B sets forth a graph showing the release of geraniol having the structure:

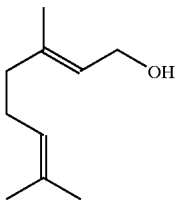

from the microparticle slurry which was applied to brown hair by washing in water. The release from the slurry includes contributions from both the neat and encapsulated aroma chemical, geraniol.

FIG. 8A is a graph showing odor intensity versus time for fragrance S in combination with encapsulated fragrance 361 and fragrance S in combination with unencapsulated fragrance 361.

FIG. 8B is a graph showing odor diffusivity versus time for mixtures of fragrance S with encapsulated fragrance 361 and fragrance S with unencapsulated fragrance 361.

FIG. 8C is a graph showing odor intensity versus time for fragrance S in combination with encapsulated fragrance 885 and fragrance S with unencapsulated fragrance 885.

FIG. 8D is a graph showing odor diffusivity versus time for fragrance S with encapsulated fragrance 885 and fragrance S with unencapsulated fragrance 885.

FIG. 8E is a graph showing odor intensity versus time for fragrance S with encapsulated fragrance 075 and fragrance S with unencapsulated fragrance 075, the encapsulation being in carnauba wax.

FIG. 8F is a graph showing odor diffusivity versus time for fragrance S with encapsulated fragrance 075 and fragrance S with unencapsulated fragrance 075, the encapsulation being in carnauba wax.

FIG. 8G is a graph showing odor intensity versus time for fragrance S and for fragrance S with encapsulated fragrance 361 in carnauba wax.

FIG. 8H is a graph showing odor diffusivity versus time for fragrance S alone and for fragrance S in combination with encapsulated fragrance 361 in carnauba wax.

FIG. 8I is a graph showing odor intensity versus time for fragrance S and for fragrance S in combination with encapsulated fragrance 885 in carnauba wax.

FIG. 8J is a graph showing odor diffusivity versus time for fragrance S alone and for fragrance S in combination with encapsulated fragrance 885 in carnauba wax.

FIG. 8K is a graph showing odor intensity versus time for fragrance S taken alone and for fragrance S in combination with encapsulated fragrance 075.

FIG. 8L is a graph showing odor diffusivity versus time for fragrance S taken alone and for fragrance S in combination with encapsulated fragrance 075 in carnauba wax.

FIG. 9A is a schematic diagram of a cutaway side elevation view of a microparticle of our invention showing substantially hydrophilic surfactant substantially entirely coated and fixedly bonded to the entirety of the outer surface of a single phase solid solution in the form of a continuous submicron layer of surfactant.

FIG. 9B shows a solid solution-microparticle of our invention wherein the substantially hydrophilic surfactant is located proximate to and immediately, substantially beneath the entirety of the outer surface of the solid solution and substantially within the internal matrix volume.

FIG. 9C shows a particle of our invention wherein the substantially hydrophilic surfactant is both (a) substantially entirely coated on and fixedly bonded to the entirety of said outer surface of said single phase solid solution in the form of a continuous submicron layer of surfactant and (b) located proximate to and immediately, substantially beneath the entirety of said outer surface of said solid solution and substantially within said internal matrix volume.

FIG. 10A is a schematic diagram showing the side view of a diffusivity testing apparatus for testing the diffusivity of entrapped and nonentrapped fragrance materials including aroma chemicals and fragrance compositions.

FIG. 10B is the top view of the apparatus of FIG. 10A.

FIG. 11A is a schematic perspective view of the first stage of the operation of a rotor/stator high shear mixer, wherein the high speed rotation of the rotor blades within the precision machined mixing workhead exerts a powerful suction drawing liquid and solid materials into the rotor/stator assembly.

FIG. 11B is a schematic perspective diagram of stage two of the operation of a rotor/stator high shear mixer used in the processes and apparatus of our invention where centrifugal force drives materials towards the periphery of the workhead where they are subjected to a milling action in the precision machined clearance between the ends of the rotor blades and the inner wall of the stator.

FIG. 11C is a schematic perspective diagram of the operation of the third stage of a rotor/stator high shear mixer useful in the apparatus of our invention and in carrying out the processes of our invention, wherein the second stage is followed by intense hydraulic shear as the materials are forced, at high velocity, out through the perforations in the stator, then through the machine outlet and along the pipework; while at the same time, fresh materials are continually drawn into the workhead, maintaining the mixing and pumping cycle.

FIG. 11D is a schematic side view of the homogenizing equipment assembly for carrying out the blending step of the processes of our invention and as part of the apparatus of our invention.

FIG. 11E is a schematic cutaway, side elevation view of a single-stage homogenizing valve assembly for the homogenizing part of the apparatus of our invention.

FIG. 11F is a cutaway side elevation view of a two-stage homogenizing valve assembly for the homogenizing apparatus for the blending step of the processes of our invention and for the apparatus of our invention.

FIG. 11G is a schematic side elevation view of a rotor/stator mixing assembly useful in the apparatus of our invention and in carrying out the blending step of the processes of our invention.

FIG. 12A sets forth a block flow diagram showing the process steps of our invention in preparing particulate compositions of our invention. FIG. 12A also shows in schematic form the apparatus of our invention.

FIG. 12B is a schematic block flow diagram setting forth the process steps of our invention for the process useful in preparing the compositions of our invention. FIG. 12B also sets forth in schematic form the apparatus of our invention.

FIG. 12C shows a schematic diagram of the apparatus and process steps of FIG. 12A with an additional schematic representation of the utilization of an electronic program controller (e.g., computer system) whereby market demand information and the like can be utilized to cause automatic alterations in the process variables of the process of our invention where ingredients are admixed, blended, heated and cooled.

FIG. 12D shows a schematic diagram of the apparatus of FIG. 12B with an additional schematic representation of the utilization of an electronic program controller (e.g., computer system) whereby market demand information and the like can be utilized to cause automatic alterations and adjustments in the process variables (e.g. blending, heating, ratio of ingredients and cooling as well as flow rates) in the process of our invention and in the apparatus of our invention.

FIG. 13 is a schematic flow diagram showing the processing in schematic form of wax microparticles containing active or bioactive ingredients of our invention.

Figure 14:
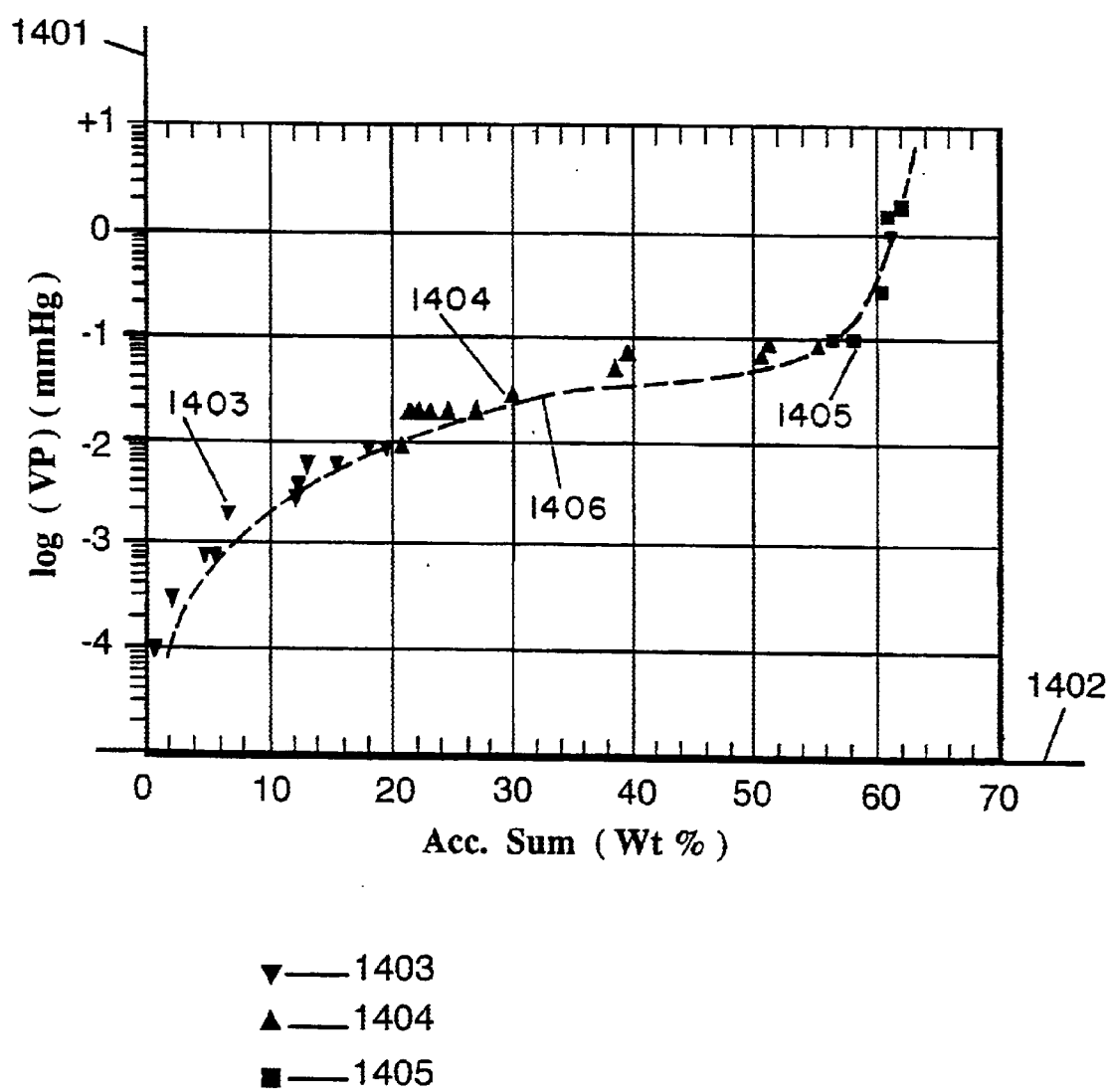

FIG. 14 is a graph showing log vapor pressure versus accumulated sum of fragrance ingredients for three different fragrances: fragrance A-1, fragrance A-2 and fragrance A-3. Each of the fragrances falls within the same graph.

Figure 15:
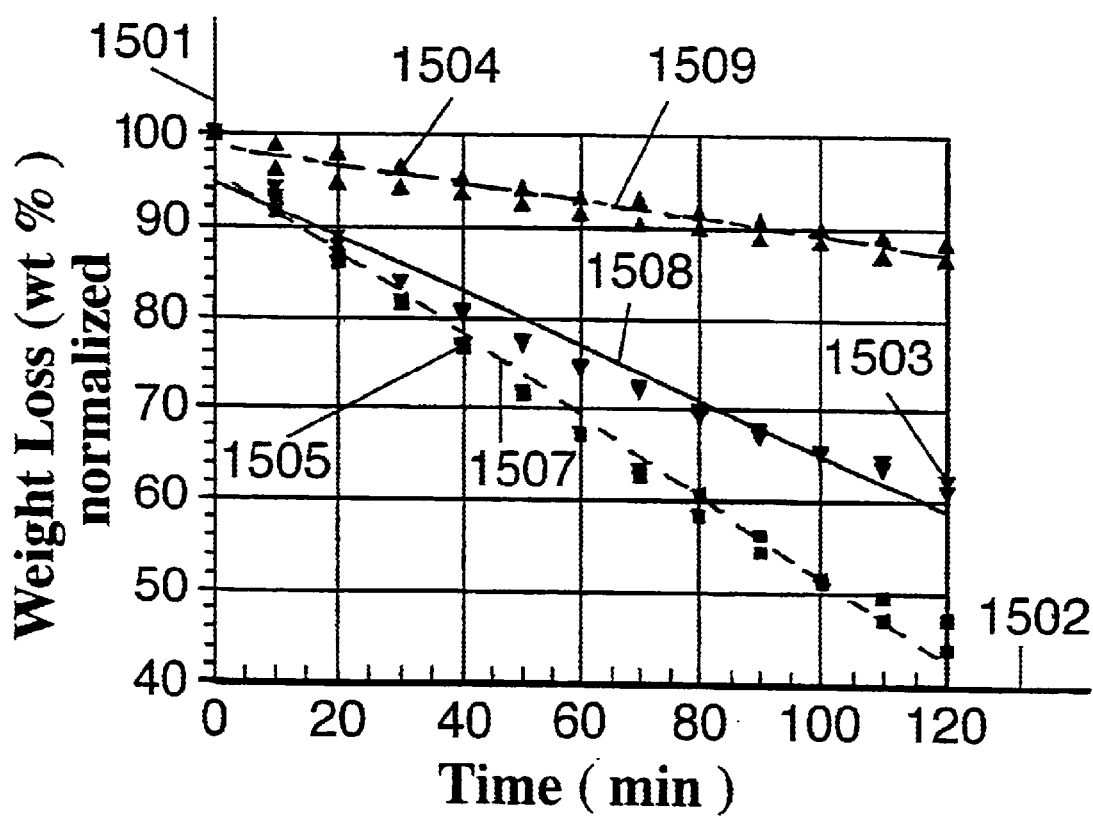

FIG. 15 is a graph showing weight loss (weight percent) normalized versus time for three different groups of ingredients: low vapor pressure materials, high vapor materials and mixtures of low and high vapor pressure materials.

Figure 16:
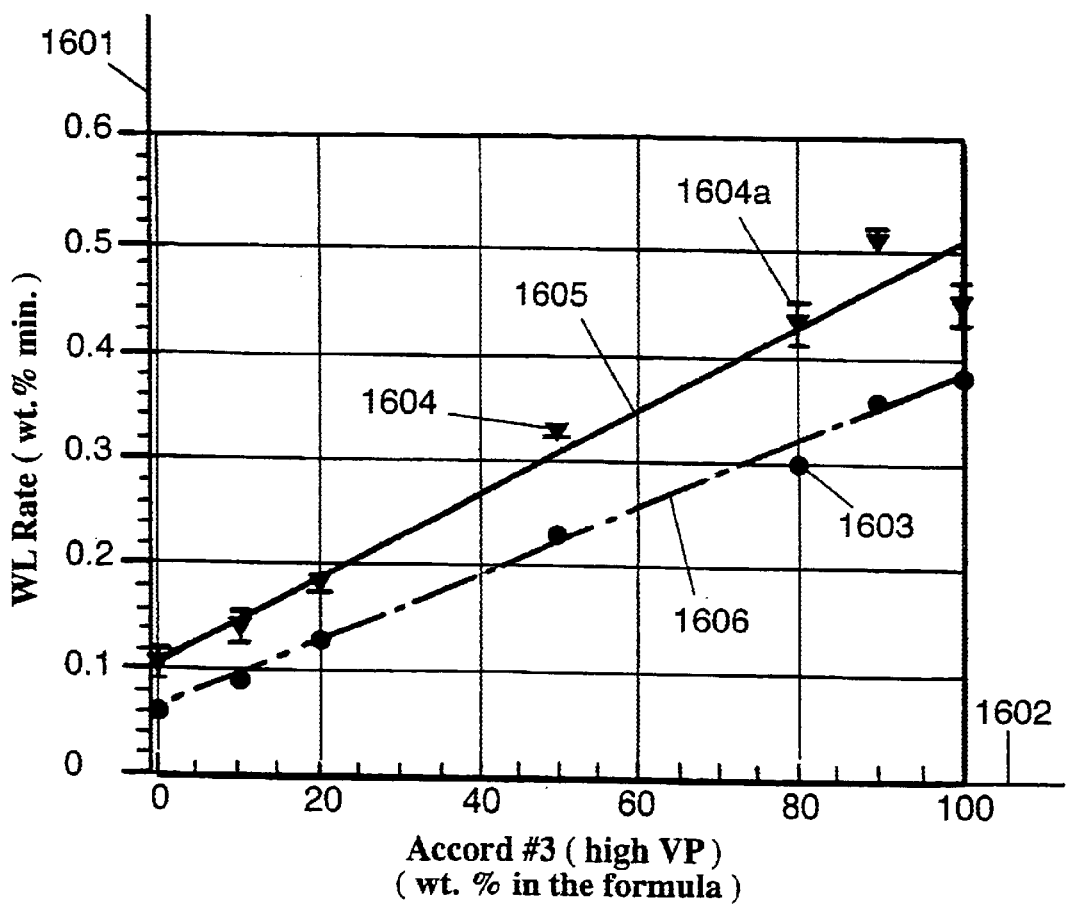

FIG. 16 is a graph showing weight loss rate (weight percent per minute) versus weight percent in the formula of fragrance A-3, a high vapor pressure fragrance, for both the fragrance diffusion evaluation system (as set forth in FIGS. 10A and 10B) and for the prior art thermal gravimetric analysis system.

FIG. 17 is a graph showing aroma chemical loading efficiencies for the chemicals: benzyl alcohol, geraniol, farnesol having the structure:

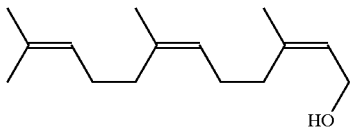

and GALAXOLIDE® (registered trademark of International Flavors & Fragrances Inc.) versus $\log_{10}P$ wherein P is the octanol-water partition coefficient for the aroma chemicals. The microparticles which are the subject of this graph are candelilla wax microparticles.

FIG. 18A sets forth a particle-size distribution for particles evolving out of the rotor/stator mixer using a composition containing 1.2% cetyl trimethyl ammonium chloride having the structure:

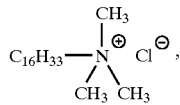

10% candelilla wax and 10% fragrance P-50448. The graph shows volume percent versus particle diameter.

FIG. 18B is a graph of volume percent versus particle diameter for particles evolving out of the homogenizer blending apparatus, which particles contain 5% cetyl trimethyl ammonium chloride, 10% candelilla wax and 10% fragrance IB-X-016.

DETAILED DESCRIPTION OF THE DRAWINGS

Referring to FIG. 1A and FIG. 1A-I, reference numeral 10 indicates the fiber itself and reference numeral 11 indicates the space between the fibers.

Referring to FIG. 1B and FIG. 1B(I), reference numeral 12 refers to the wax microparticles located on the surface of the fabric.

Referring to FIG. 2A and FIG. 2A(I), reference numeral 20 refers to the hair strand itself.

Referring to FIGS. 2B and 2B(I), reference numeral 21 refers to the wax microparticles located on the surface of the hair strands.

Referring to FIGS. 2C and 2C(I), reference numeral 23 refers to the strand of hair washed with a conditioner.

Referring to FIGS. 2D and 2D(I), reference numeral 24 refers to the wax microparticles located on the surface of the hair strands.

Referring to FIG. 3A, the bundles of fibers are referred to by reference numerals 30a and 30b. The microparticle entrapped in the pores between the bundles is referred to by reference numeral 32. The space between the bundles is referred to by reference numeral 31. FIG. 3A is an enlargement of section 3A of FIG. 3B.

Referring to FIG. 3B, the fiber bundles are shown by reference numeral 33. The microparticle entrapped between the bundles is shown by reference numeral 36, being entrapped in space 37. The fiber bundles are shown by reference numerals 33a and 33b and, in addition, reference numerals 34 and 34b. The microparticle directly adhered through physical forces onto a bundle is shown by reference numeral 35.

Referring to FIGS. 4A and 4B, fluid 46 is located in jar 44. Jar 44 has sidearm 45. The fluid 46 reaches fluid level 47. Directly in line with fluid level 47 is membrane 41. The diffusion membrane 41 is held in place with flanges 43 and jar lip 42, using bolts 401a and 401b which secures the flange in place. The sidearm 45 is closed using closure 49. The permeability apparatus is shown using reference numeral 40. The IFF permeability test is based on the use of the apparatus of FIGS. 4A and 4B. The weight of membrane 41 is taken, initially, before being placed within the flange 43 and the jar lip 42. Substance 46 for which the permeability is to be measured is placed into jar 44 to fluid level 47. The apparatus containing fluid 46 remains in place for a fixed period of time. At the end of that period of time, bolts 401a and 401b as well as 401c are loosened, the flange 43 removed and membrane 41 is removed and weighed, thereby gathering sufficient data to determine the permeability of the particular substance 46. Referring to FIG. 5A, reference numeral 52 are data points for aldehyde C-8. Reference numeral 53 shows data points for ethyl tiglate. The Y axis measures weight loss and is indicated by reference numeral 54. The X axis shows time in minutes and is indicated by reference numeral 55. The weight loss is measured in $$\frac{mg - mm}{cm^2}.$$

Reference numeral 51 shows the standard deviation for the data.

In FIG. 5B, reference numeral 503 represents data points for aldehyde C-8. Reference numeral 502 represents data points for β-pinene. Reference numeral 58 represents data points for ethyl tiglate. Reference numeral 501 shows the graph for weight loss versus time for ethyl tiglate, thus showing the permeability of carnauba wax to ethyl tiglate. The Y axis for weight loss is indicated by reference numeral 56, and the X axis for time is indicated by reference numeral 57. Reference numeral 59 sets forth the standard deviation for the data for ethyl tiglate.

Referring to FIG. 5C, reference numeral 507 is for ethyl tiglate, encapsulated. Reference numeral 508 is for the graph of ethyl tiglate for weight loss versus time, showing the permeability of carnauba wax to ethyl tiglate. Reference numeral 506 shows the data points for β-pinene in carnauba wax. Reference numeral 510 shows data points for ethyl tiglate without being entrapped in any control release system such as carnauba wax. Reference numeral 509 shows data points for the β-pinene control in the absence of carnauba wax. Reference numeral 511 sets forth the graph of unentrapped ethyl tiglate. Reference numeral 512 sets forth the graph of unentrapped β-pinene. The Y axis showing weight loss is indicated by reference numeral 505. The X axis showing time in minutes is indicated by reference numeral 504.

Referring to FIG. 5D, reference numeral 515 sets forth the data points for ethyl tiglate in the polyethylene (molecular weight 500) wax. Reference numeral 520 is for the graph of time versus weight loss. Reference numeral 516 shows data points for aldehyde C-8 in polyethylene wax. Reference numeral 517 shows data points for β-pinene in polyethylene wax. Reference numeral 519 indicates the graph for aldehyde C-8 in polyethylene wax, showing the permeability of aldehyde C-8 through polyethylene wax. Reference numeral 520 shows the graph for ethyl tiglate in polyethylene wax showing the permeability of ethyl tiglate through polyethylene wax. The X axis is indicated by reference numeral 513, and the Y axis is indicated by reference numeral 514.

Referring to FIG. 5E, reference numeral 528 refers to cetyl palmitate (CUTINA® wax). Reference numeral 527 refers to data points for carnauba wax. Reference numeral 526 refers to data points for polyethylene wax. Reference numeral 525 refers to data points for candelilla wax. Reference numeral 523 refers to the control for β-pinene without wax. All data points set forth on FIG. 5E, except for the control, show the permeability of β-pinene through waxes. The X axis is indicated by reference numeral 521, showing time and minutes, and the Y axis is indicated by reference numeral 522, showing weight lossin $$\frac{mg-mm}{cm^2}.$$

FIG. 5E(A) shows that portion of FIG. 5E where the weight loss is between zero and b 1.4for the β-pinene contained in the waxes. In FIG. 5E(A), reference numeral 533 shows the standard deviation line. The X axis is indicated by reference numeral 521, and the Y axis is indicated by reference numeral 522 for weight loss. Reference numeral 528 shows data points for cetyl palmitate. Reference numeral 526 shows data points for polyethylene wax (molecular weight 500). Reference numeral 530 sets forth the graph for time versus weight loss for polyethylene wax containing β-pinene. Reference numeral 533a is the standard deviation line for the data points for polyethylene wax containing β-pinene. Reference numeral 529 shows the graph for carnauba wax containing β-pinene and sets forth the permeability of β-pinene through carnauba wax.

Referring to FIG. 5F, reference numeral 538 shows the data points for cetyl palmitate (CUTINA® wax). Reference numeral 540 shows data points for carnauba wax. Reference numeral 541 shows data points for polyethylene (molecular weight 500) wax. Reference numeral 542 shows data points for candelilla wax. Reference numeral 537 shows data points for the control, ethyl tiglate without wax. Reference numeral 536 is the graph showing the evaporation rate for the control, ethyl tiglate without wax. Reference numeral 539 is the graph showing permeability of ethyl tiglate through cetyl palmitate (CUTINA® wax). Reference numeral 543 sets forth the graph showing permeability of ethyl tiglate through carnauba wax. The X axis is indicated by reference numeral 534 for time (minutes). The Y axis is indicated by reference numeral 535 for weight loss $$\left(\frac{mg-mm}{cm^2}\right).$$

Referring to FIG. 5G, reference numeral 562 indicates data points for β-pinene contained in hydroxypropyl cellulose. Reference numeral 564 indicates data points for β-pinene not contained in any polymer, but merely showing the evaporation rate of the β-pinene. Reference numeral 569 shows the standard deviation for the data points for β-pinene without being contained in hydroxypropyl cellulose. Reference numeral 563 shows the data points for ethyl tiglate contained in hydroxypropyl cellulose. Reference numeral 565 sets forth the data points for ethyl tiglate not being contained in any polymer and showing the evaporation rate of ethyl tiglate. Reference numeral 567 sets forth the graph showing the permeability of ethyl tiglate through hydroxypropyl cellulose. Reference numeral 568 sets forth the graph showing the evaporation of ethyl tiglate (without being contained in any polymer). Reference numeral 566 sets forth the graph showing the evaporation of β-pinene without being present in any polymer. The X axis is indicated by reference numeral 561 showing time in minutes, and the Y axis is indicated by reference numeral 560 showing weight loss in $$\frac{mg-mm}{cm^2}.$$

Referring to FIG. 5H, reference numeral 552 shows the data points for ethyl tiglate contained in polyvinyl alcohol. Reference numeral 553 sets forth the data points for β-pinene contained in polyvinyl alcohol (99% hydrolyzed polyvinyl acetate). Reference numeral 554 sets forth the data points for ethyl tiglate not contained in polyvinyl alcohol and merely shows the evaporation rate of the ethyl tiglate. Reference numeral 555 sets forth the data points for β-pinene not being contained in any polyvinyl alcohol, but merely showing the evaporation rate of the β-pinene. Reference numeral 557 sets forth the graph showing the evaporation rate of β-pinene not being contained in any polyvinyl alcohol. Reference numeral 559 sets forth the standard deviation for the data points for ethyl tiglate and β-pinene not being contained in any polyvinyl alcohol. The X axis for time (minutes) is shown by reference numeral 551. The Y axis for weight loss $$\left(\frac{mg-mm}{cm^2}\right)$$

is shown by reference numeral 560.

Referring to FIG. 6A, percent substantivity is shown on the Y axis by reference numeral 60. The bar graph for neat geraniol using a plain water wash is shown by reference numeral 61a. The bar graph for geraniol contained in candelilla wax microparticles is shown by reference numeral 61b for a plain water wash. The bar graph for neat geraniol using a detergent is shown by reference numeral 62a. The bar graph for neat geraniol in candelilla wax microparticles is shown by reference numeral 62b for detergents. The bar graph for fabric softeners for neat geraniol is shown by reference numeral 63a. The bar graph for geraniol contained in candelilla wax microparticles in fabric softeners is shown by reference numeral 63b.

Referring to FIG. 6B, substantivity (percent) is shown on the Y axis indicated by reference numeral 64. Reference numeral 65a sets forth the substantivity of neat geraniol in a plain water wash on polyester fabric. Reference numeral 65a' sets forth the standard deviation line for the neat geraniol in a plain water wash. Reference numeral 65b sets forth the use of neat geraniol encapsulated in candelilla wax microparticles for a plain water wash. Reference numeral 65b' sets forth the standard deviation line for the encapsulated geraniol in candelilla wax using a plain water wash. Reference numeral 66a sets forth the use of neat geraniol in a detergent on polyester fabrics. Reference numeral 66b sets forth the use of geraniol encapsulated in candelilla wax microparticles used in a detergent. Reference numeral 67a sets forth the use of neat geraniol in a fabric softener on polyester fabrics. Reference numeral 67b sets forth the use of geraniol encapsulated in candelilla wax microparticles used in a fabric softener on polyester fabrics.

Referring to FIG. 6C, the Y axis shows substantivity in terms of percentages and is shown by reference numeral 601. Reference numeral 602a sets forth the use of neat GALAXOLIDE® in a detergent on cotton fabric. Reference numeral 602b sets forth the use of GALAXOLIDE® encapsulated in candelilla wax microparticles on cotton fabrics in a detergent. Reference numeral 603a sets forth the use of neat GALAXOLIDE® in a fabric softener on cotton fabrics. Reference numeral 603b sets forth the use of GALAXOLIDE® encapsulated in candelilla wax microparticles in fabric softener on cotton fabrics.

Referring to FIG. 6D, substantivity (percent) is set forth on the Y axis using reference numeral 604. In FIG. 6D, reference numeral 605a refers to the use of neat GALAXOLIDE® in a detergent on polyester fabrics. Reference numeral 605b refers to the use of GALAXOLIDE® encapsulated in candelilla wax microparticles in a detergent for use on polyester fabrics. Reference numeral 605b' refers to the standard deviation for the use of GALAXOLIDE® encapsulated in candelilla wax microparticles with a detergent on polyester fabrics. Reference numeral 606a refers to the use of neat GALAXOLIDE® in a fabric softener on polyester fabrics. Reference numeral 606a' refers to the standard deviation of the data of neat GALAXOLIDE® in a fabric softener for use on polyester fabrics. Reference numeral 606b refers to the use of GALAXOLIDE® encapsulated in candelilla wax microparticles in a fabric softener for use on polyester fabrics. Reference numeral 606b' refers to the standard deviation of the data for GALAXOLIDE® encapsulated in candelilla wax microparticles for use with a fabric softener on polyester fabrics.

Referring to FIG. 7A, showing the sustained release of GALAXOLIDE® over a period of two days as the neat aroma chemical and when encapsulated in candelilla wax microparticles. Reference numeral 70 indicates the Y axis. Reference numeral 71 indicates the X axis in time in days. Reference numeral 72 sets forth the graph for the use of the neat GALAXOLIDE®. Reference numeral 72' sets forth the data points for the neat GALAXOLIDE®. Reference numeral 73 sets forth the graph for the GALAXOLIDE® contained in the candelilla wax microparticles. Reference numeral 703 sets forth the data points for the GALAXOLIDE® encapsulated in candelilla wax microparticles. Reference numeral 704 sets forth the standard deviation for the data points for GALAXOLIDE® encapsulated in candelilla wax microparticles.

Referring to FIG. 7B, reference numeral 74 refers to the Y axis which refers to the percent of aroma chemical (geraniol) remaining on brown hair, and reference numeral 75 refers to the X axis indicating time of release in days. Reference numeral 76 sets forth the graph showing the rate of release of neat geraniol. Reference numeral 701 sets forth the data points for the neat geraniol. Reference numeral 702 sets forth the standard deviation for the data points for the neat geraniol. Reference numeral 77 sets forth the graph for the rate of release of geraniol encapsulated in candelilla wax microparticles. Reference numeral 79 sets forth the data points for geraniol encapsulated in candelilla wax microparticles. Reference numeral 78 sets forth the standard deviation for the data points for geraniol encapsulated in candelilla wax microparticles.

Referring to FIG. 8A, the Y axis indicating odor intensity on a scale of 1–10 is indicated by reference numeral 80. The X axis indicating time in hours is indicated by reference numeral 81. Reference numeral 82 refers to the graph of odor intensity versus time for fragrance S in combination with encapsulated fragrance 361. Reference numeral 83 refers to the graph of odor intensity versus time for the combination of fragrance S and encapsulated fragrance 361.

Referring to FIG. 8B, the Y axis is indicated by reference numeral 84 for odor diffusivity on a scale of 1–10. The X axis is indicated by reference numeral 85 for time in hours. Reference numeral 86 indicates the graph of odor diffusivity versus time for fragrance S in combination with encapsulated fragrance 361. Reference numeral 87 indicates the graph of odor diffusivity versus time for fragrance S in combination with unencapsulated fragrance 361.

Referring to FIG. 8C, reference numeral 801 indicates the graph of odor intensity versus time for fragrance S and encapsulated fragrance 885. Reference numeral 802 indicates the graph of odor intensity versus time for fragrance S and unencapsulated fragrance 885.

Referring to FIG. 8D, reference numeral 803 shows the graph of odor diffusivity versus time for fragrance S and encapsulated fragrance 885. Reference numeral 804 indicates the graph for odor diffusivity versus time for fragrance S in combination with unencapsulated fragrance 885.

Referring to FIG. 8E, reference numeral 805 indicates the graph of odor intensity versus time for fragrance S and encapsulated fragrance 075. Reference numeral 806 sets forth the graph of odor intensity versus time for fragrance S and unencapsulated fragrance 075.

Referring to FIG. 8F, reference numeral 807 shows the graph of odor diffusivity versus time for fragrance S and encapsulated fragrance 075. Reference numeral 808 sets forth the graph of odor diffusivity versus time for fragrance S and unencapsulated fragrance 075. These graphs suggest that the carrier retains the topnotes during storage and adheres to the hair.

Referring to FIG. 8G, reference numeral 809 sets forth the graph for odor intensity versus time for fragrance S taken alone. Reference numeral 810 sets forth the graph of odor intensity versus time for fragrance S taken together with encapsulated fragrance 361.

Referring to FIG. 8H, reference numeral 811 sets forth the graph of odor diffusivity versus time for fragrance S taken alone. Reference numeral 812 sets forth the graph of odor diffusivity versus time for fragrance S taken in combination with encapsulated fragrance 361. The system containing the encapsulated fragrance clearly provides an advantage over the neat oil. The observed difference in intensity between these systems is large enough to provide a perceived difference.

Referring to FIG. 8I, the graph indicated by reference numeral 813 is for the odor intensity versus time for fragrance S taken alone. The graph indicated by reference numeral 814 is for odor intensity versus time for fragrance S taken together with encapsulated fragrance 885.

Referring to FIG. 8J, the graph indicated by reference numeral 815 is for odor diffusivity versus time for fragrance S taken alone. The graph indicated by reference numeral 816 is for odor diffusivity versus time for fragrance S taken together with encapsulated fragrance 885.

Referring to FIG. 8K, the graph indicated by reference numeral 817 is for odor intensity versus time for fragrance S taken alone. The graph indicated by reference numeral 818 is for odor intensity versus time for fragrance S taken together with encapsulated fragrance 075.

Referring to FIG. 8L, the graph indicated by reference numeral 819 is for odor diffusivity versus time for fragrance S taken alone. The graph indicated by reference numeral 820 is for odor diffusivity versus time for fragrance S taken together with encapsulated fragrance 075. These graphs show that the volume and the tenacity of encapsulated fragrance 075 is higher than that of fragrance S taken alone up to 5 hours. The encapsulation system may be used to increase substantivity.

Referring to FIG. 9A, the substantially hydrophilic surfactant 93 is substantially, entirely coated on and fixedly bonded to the entirety of the outer surface 95 of the single phase solid solution 91 in the form of a continuous submicron layer of surfactant 92. The particle having surfactant coated thereon in a submicron layer is indicated by reference numeral 90.

Referring to FIG. 9B, the substantially hydrophilic surfactant 903 is located proximate to and immediately substantially beneath the entirety of the outer surface 905 of the solid solution 901 and substantially within the internal matrix volume. The charge on the particle is shown using reference numeral 904, and the particle itself is shown by reference numeral by reference numeral 900.

Referring to FIG. 9C, the substantially hydrophilic surfactant 917/913 is both (a) substantially, entirely coated on and fixedly bonded to the entirety of the outer surface 915 of the single phase solid solution 911 in the form of a continuous submicron layer of surfactant 912 and (b) located proximate to and immediately, substantially beneath the entirety of the outer surface of said solid solution 915 and substantially within the internal matrix volume. The surfactant within the matrix volume is indicated by reference numeral 917. The surfactant within the submicron layer is indicated by reference numeral 913. The particle is indicated by reference numeral 910. The charge on the outer surface 916, the particle, is indicated by reference numeral 914.

FIGS. 10A and 10B set forth the fragrance diffusion evaluation system for determining the diffusivity and permeability of fragrance materials and other active and bioactive ingredients used in the practice of our invention. The test sample on blotters indicated by reference numeral 1001 are supported by support 1002 in container 1003 having opening 1004 to the atmosphere. Air flow through line 1010 is supplied from air supply 1005 through tube 1006, having pressure gauge 1007 measuring the air flow. Container 1003 has side wall 1012 through which temperature probe 1009 is located. Temperature probe 1009 is attached to temperature monitor 1008. Container 1003 has base 1001. The overall apparatus is indicated by reference numeral 1000. FIG. 10B sets forth a top view of the apparatus of FIG. 10A showing the use of two tandem chambers 1003a and 1003b. Container 1003a is supplied with air flow through tube 1010a having pressure gauge 1007b in the air flow line. Container 1003b is supplied with air flow through tube 1010b with pressure gauge 1007a in its line. Air supply from location 1005 supplies air through line 1006a having pressure gauge 1007 in the line to measure air flow. The air flow is then split between line 1006b (for air flowing into container 1003a) and line 1006c (for air flowing to container 1003b). Temperature probe 1009a is used for container 1003a, and temperature probe 1009b is used for container 1003b. Temperature probe 1009b is attached to temperature monitor 1008b. Temperature probe 1009a is attached to temperature monitor 1008a. Container 1003a has opening 1004a at the top of same. Container 1003b has opening 1004b at the opening thereof. The overall apparatus having tandem containers for testing purposes is indicated by reference numeral 1000'.

The system shown in FIGS. 10A and 10B has as its primary purpose the simultaneous evaluation of an air freshener's performance for its hedonics, intensity, volatile content and weight loss as a function of time in a controlled environment of temperature and air mixing. The fragrance diffusion evaluation system is a midway station between a laboratory system that allows only analytical measurements and a full scale test of odor performance in a specially designed room that allows only sensory testing. The fragrance diffusion evaluation system provides a controlled environment that allows for both sensory and analytical measurements of a fragrance's performance at low cost.

The fragrance diffusion evaluation system, shown in FIGS. 10A and 10B, comprises a cylinder having a height of between about 50 and about 75 cm, a radius of between about 15 and 30 cm and a volume of between about 0.1 and 0.2 $m^3$. The interior is coated with aluminum foil to ensure that no fragrance absorbs into the walls. The air flow is provided by a tube through the side between about 3 and about 10 cm from the bottom extending to the center of the chamber. The temperature is continuously monitored by a gauge located between about 10 and about 30 cm from the bottom. An opening with a diameter of between 15 and 30 cm is at the top of the cylinder to allow air flow and odor intensity testing. The air flow is, on average, between about 900 and 1,000 ml per minute. This air flow replaces the whole volume of the fragrance diffusion evaluation system with fresh air every 2 hours. The air flow through the chamber is constant at a pressure of between about 0.5 and 2 psig.

Referring to FIG. 11A, the high speed rotation of the rotor blades 1106 within the precision machine mixing workhead exerts a powerful suction at location 1101 drawing liquid and solid materials 1104a into the rotor stator assembly 1100. The rotation is effected at access 1102. The output from the assembly is at location 1103. The workhead is indicated by reference numeral 1105. The overall device is indicated by reference numeral 1100. Referring to FIG. 11B, centrifugal force then drives materials 1104a towards the periphery of the workhead where they are subjected to a milling action in the precision machined clearance between the ends of the rotor blades and the inner wall of the stator.

Referring to FIG. 11C, stage 2 is followed by intense hydraulic shear as the materials 1104b are forced at high velocity out through the perforations in the stator 1106, then through the machine outlet and along the pipework 1103. At the same time, fresh materials are continually drawn into the workhead at 1101, maintaining the mixing and pumping cycle.

Referring to FIG. 11E, the single-stage homogenizing valve assembly, valve handle 1112a is used to adjust the flow inwardly at location 1113a and outwardly at location 1114a.

Referring to FIG. 11F, FIG. 11F sets forth a two-stage valve assembly for the homogenizer. Valve handle 1111 is used to adjust the first stage, and valve handle 1112 is used to adjust the second stage. The two-stage valve assembly contains seals 1117 and gaps 1115 and 1116. Reference numeral 1113 refers to the inlet to the two-stage valve assembly, and reference numeral 1114 refers to the outlet of the two-stage valve assembly. Reference numeral 1118 refers to the passageway between the inlet 1113 and the outlet 1114. The overall two-stage valve assembly is indicated by reference numeral 1110. Referring to FIG. 11D, FIG. 11D is the homogenizing equipment assembly. Mixer 1120 containing mixing shaft 1112 is a steam-heated feeder tank. The homogenizing equipment assembly is shown with the two-stage pressure adjustment system wherein the first-stage hand wheel is shown by reference numeral 1111, and the second-stage hand wheel is shown by reference numeral 1112. Pressure gauge 1122 is used to monitor the flow of fluid containing emulsion through a three-way bypass valve to cooling coils 1130 and recycle line 1114. Temperature gauge 1124 monitors the temperature of fluid flowing through line 1113 into the two-stage valve assembly which is attached to gear box 1123. The overall homogenizing equipment assembly is indicated by reference numeral 1110.

Referring to FIG. 11G, the rotor/stator mixing assembly, the initial blending operation is carried out in steam-heated feeder tank 1140 equipped with stirrer 1146. Fluid flows through line 1144 into rotor/stator mixing head 1142 controlled through control box 1141. The fluid then flows through line 1144 into three-way valve 1150. The fluid flows through cooling coils 1143 and 1143*a*. The fluid also flows past the three-way valve through recycle lines 1147 and 1147*a* back into feeder tank 1140. The rotor/stator mixing assembly is indicated by reference numeral 1190.

Referring to FIG. 12A, fragrance material from container 1201 flows through line 1203 controlled by valve 1202. Simultaneously, polymer and/or wax from container 1204 heated using heater 1205 flows through line 1207 controlled by valve 1206. Both fragrance material, polymer and/or wax flowing through lines 1203 and 1207 are blended in mixing tank 1208 which is also equipped with heater 1212. The thus-formed blend passes through line 1219 controlled by valve 1218 into blender 1220 simultaneously with product evolving from mixer 1215. Thus, surfactant from container 1209 flows through line 1214 past control valve 1211, and simultaneously, water or aqueous mixture from container 1210, preheated using heater 1230, flows through line 1213 past control valve 1212 into mixing vessel 1215, also equipped with heater 1231. The surfactant/aqueous mixture is then passed through line 1217 past control valve 1216 into blender 1220 along with product from line 1219. Blender 1220 is a homogenizer and/or rotor/stator high shear mixer. Subsequent to the blending using the homogenizer and/or rotor/stator high shear mixer, product is passed through line 1223 past control valve 1222 into solid phase particle formation vessel 1225 equipped with cooling coils 1224, or apparatus components 1220 and 1225 can be combined into assembly 1190 as shown in FIG. 11G or assembly 1110 as shown in FIG. 11D. The resulting particulate slurry is then passed through line 1227 past control valve 1226 into a vessel for further utilization.

Referring to FIG. 12B, fragrance material from container 1250 is passed through line 1259 past control valve 1258 into mixer 1260 equipped with heater 1261. Simultaneously, polymer and/or wax from container 1251 equipped with heater 1252 is passed through control line 1256 past valve 1257 into mixer 1260. Simultaneously, surfactant from container 1253 is passed through line 1254 past valve 1255 into mixing vessel 1260. While mixing vessel 1260 is engaged in mixing fragrance material, polymer or wax and surfactant, aqueous composition heated through heater 1265 in container 1264 is then passed through line 1266 past control valve 1267 into blender 1268. Product mixed in container 1260 is passed through line 1262 past control valve 1263 into blender 1268. Blender 1268 can be a homogenizer and/or a rotor/stator high shear mixer. The resulting product is then passed through line 1269 past valve 1270 into solid phase particle formation vessel 1271 equipped with cooling coils 1272. In the alternative, apparatus components 1271 and 1268 can be combined into assemblies 1190, as shown in FIG. 11G, or 1110, as shown in FIG. 11D. The resulting product containing solid particulate particles having continuous surfaces is then passed through line 1273 past valve 1274 into container 1275 for utilization of the slurry.

The apparatus of FIG. 12A can be used in conjunction with electronic program controller 1300 as shown in FIG. 12C. Electronic program controller 1300 uses marketing input information from source 1299 via control line 1299*c* feeding into the electronic program controller 1300 and controlling the apparatus as illustrated in FIGS. 12A and 12C via control lines. Thus, the apparatus shown in schematic diagram in FIG. 12A is also shown in schematic form in FIG. 12C as associated with the electronic program controller (computer mechanism) via control lines.

More specifically, the control of fragrance material from container 1201 through line 1203 past control valve 1202 is controlled via control line 1202*c*. By the same token, flow of polymer and/or wax from container 1204 through line 1207 past valve 1206 is controlled through control line 1206*c*. The rate of heating and amount of heat energy into container 1204 using heater 1205 is controlled through control line 1205*c*. The mixing vessel 1208 mixing fragrance material, polymer and/or wax is heated through heater 1221 which is controlled through control line 1221*c*. The energy of mixing in mixing vessel 1208 is controlled through control line 1208*c*. Surfactant contained in container 1209 is fed through line 1214 past valve 1211 into mixing vessel 1215, and water or aqueous solution from container 1210 is heated using heater 1230 and flows past valve 1212 into mixing vessel 1215. The flow of the aqueous solution from container 1210 past valve 1212 is controlled through control line 1212*c*. The amount of heat energy into the aqueous solution in container 1210 is controlled through control line 1230*c*. The rate of flow of surfactant from container 1209 into mixing vessel 1215 is controlled through control line 1211*c*. The heat input into mixing vessel 1215 through heater 1231 is controlled through control line 1231*c*. The surfactant/aqueous solution mixture created in container 1215 is passed through line 1217 into blender 1220. The mixing energy in blender 1220 is controlled through control line 1220*c*. The flow of product from container 1208 into blending vessel 1220 (e.g., homogenizer) through line 1219 past valve 1218 is controlled through control line 1218*c*. The control of surfactant/aqueous composition from mixing vessel 1215 through line 1217 past valve 1216 into blender 1220 is controlled through control line 1216*c*. The flow of microemulsion from blender 1220 through line 1223 past control valve 1222 is controlled through control line 1222*c*, and the cooling energy using cooler 1224 for solid phase particle formation vessel 1225 is controlled through control line 1224*c*. The mixing energy in the solid phase particle formation vessel 1225 is controlled through control line 1225*c*. The flow from the solid phase particle formation vessel 1225 to utilization/storage/ inventory vessel 1228 is controlled through control line 1226c, and marketing input information and output information are gathered through control line 1228c.

By the same token, the apparatus of FIG. 12B can be used in conjunction with electronic program controller 1302 which uses marketing input information from source 1301 via a control line feeding into the electronic program controller 1302 and controlling the apparatus as illustrated in FIG. 12B and FIG. 12D via control lines. Thus, the apparatus shown in schematic diagram in FIG. 12B is also shown in schematic form in FIG. 12D as associated with the electronic program controller (computer mechanism) via control lines.

More specifically, fragrance material from container 1250 passing through line 1259 past valve 1258 has its flow controlled through control line 1258c. The polymer and/or wax from container 1251 passing through line 1256 past control valve 1257 has its flow controlled through control line 1257c. Simultaneously, the heat input into container 1251 for heating the polymer and/or wax material using heater 1252 is controlled through control line 1252c. Simultaneously, surfactant from container 1253 flowing through line 1254 past valve 1255 has its flow controlled through control line 1255c. The surfactant, the polymer and/or wax and the fragrance material are mixed in mixing vessel 1260, and the mixing energy is controlled through control line 1260c and the heat input to the mixing vessel is controlled through control line 1261c. Aqueous composition is heated in container 1264 through heating element 1265 which is controlled through control line 1265c. The aqueous composition flow through line 1266 past valve 1267 is controlled through control line 1267c. The mixture of fragrance material, polymer and/or wax and surfactant in mixing vessel 1260 then flows through line 1262 past control valve 1263, and the flow of this mixture into blender (e.g., homogenizer) 1268 is controlled through control line 1263c. The flow of aqueous composition into the blender (e.g., homogenizer) from container 1264 through line 1266 past valve 1267 is controlled through control line 1267c. The homogenizing energy for blender 1268 is controlled through control line 1268c. The product emanating from blender 1268 through line 1269 past valve 1270 has its flow controlled through control line 1270c. The solid phase particle formation component of the apparatus of our invention 1271 is equipped with cooling coils 1272, controlled through control line 1272c. Operation of the solid phase particle formation component of the apparatus of our invention is controlled through control line 1271c. Flow from the solid phase particle formation vessel into the utilization of slurry, storage, inventory and marketing vessel 1275 past valve 1273 through line 1274 is controlled through control line 1273c. Marketing input and output to location 1275 is controlled through control line 1275c.

Referring to FIG. 13, the wax phase from location 1306 is admixed with fragrance oil and optional additives at location 1308 and fed into vessel 1309, simultaneously with water with emulsifier heated to 90° C. from location 1305 mixed with surfactant from location 1307 also flowing into vessel 1309. Fluid from vessel 1309 is passed through mixer or homogenizer 1310 and recycled back into vessel 1309 for a given period of time, e.g., one minute. The resulting fluid shown at location 1311 is then again passed through homogenizer 1312 and then quenched to solidify microparticles using a heat exchanger at location 1313.

Referring to FIG. 14, reference numeral 1403 refers to the data points for fragrance A-1. Reference numeral 1404 refers to the data points for fragrance A-2. Reference numeral 1405 refers to the data points for fragrance A-3. Reference numeral 1406 refers to the graph for data points 1403, 1404 and 1405. The Y axis is referred to using reference numeral 1401 for the $\{\log_{10}[VP]\}$ (of vapor pressure). The X axis is indicated by reference numeral 1402 and is for the accumulated sum (in weight percent) of the fragrance ingredients, fragrances A-1, A-2 and A-3. The graph 1406 is also described using the equation:

$$\{\log_{10}[VP]\} = (0.046)S^3 + (1.673)S^2 - (16.41)S - 4$$

wherein S represents the accumulated sum (weight percent) of the fragrance ingredients and $\{\log_{10}[VP]\}$ represents the log of the vapor pressure of each of the fragrance ingredients.

Referring to FIG. 15, the Y axis is indicated by reference numeral 1501 and represents weight loss (weight percent), normalized and shown by the symbol W. The X axis represents time and is indicated by reference numeral 1502 with time being shown by the symbol $\theta$. Reference numeral 1503 indicates data points for the 50:50 mixture of high and low vapor pressure substances. Reference numeral 1504 represents data points for low vapor pressure substances (that is, <0.01 mm/Hg); and reference numeral 1505 represents data points for high vapor pressure substances (>0.1 mm/Hg). Reference numeral 1508 is the graph for weight loss versus time for the mixture of high and low vapor pressure substances (50:50) and is represented by the equation:

$$W = 94.583 - 0.29497\theta.$$

Reference numeral 1509 is the equation for weight loss versus time for low vapor pressure materials and is represented by the equation: $W = 98.679 - 0.09478\,\theta$; and reference numeral 1507 is the graph for weight loss versus time for high vapor pressure materials and is represented by the equation: $W = 95.679 - 0.43843\,\theta$.

With respect to FIG. 16 concerning the fragrance diffusion evaluation system, the Y axis concerning weight loss rate (weight percent per minute) is indicated by reference numeral 1601 and is shown by the term $$\left(\frac{dW}{d\theta}\right).$$

The X axis representing weight percent in the formula of fragrance A-3 is indicated by reference numeral 1602 and is also represented by the term W. Reference numeral 1603 represents the data points for the weight loss rate versus weight percent in the formula as measured by thermal gravimetric analysis (TGA). Reference numeral 1604 represents the data points for the weight loss rate versus weight percent in the formula as measured by the fragrance diffusion evaluation system (FES) of FIGS. 10A and 10B. Reference numeral 1604a shows the standard deviation for the data points 1604. Reference numeral 1605 is the graph for weight loss rate versus weight percent in the formula as measured by the fragrance diffusion evaluation system and is represented by the equations:

$$\left(\frac{dW}{d\theta}\right) = 0.10675 + 0.003965W$$

and $$Ln_e(0.10675 + 0.00395W) = \theta.$$

$$Ln_e(0.110675 + 0.00395W) = \theta.$$

The reference numeral 1606 is for the graph of weight loss rate versus weight percent in the formula as measured by thermal gravimetric analysis and is represented by the equations:

$$\left(\frac{dW}{d\theta}\right) = 0.061929 + 0.00319W$$

and $$Ln_e(0.061929 + 0.00319W) = \theta.$$

The thermogravimetric analysis (TGA) of the prior art is described in detail in Kroschwitz, "Polymers: Polymer Characterization and Analysis" published by John Wiley and Sons, 1990 at pages 837–848 (Chapter entitled: "Thermal Analysis") incorporated by reference herein.

With reference to FIG. 17, the Y axis is indicated by reference numeral 1701 and is for aroma chemical loading efficiency indicated by the symbol: $\epsilon$. The X axis is indicated by reference numeral 1702 and is for the $\log_{10}P$ wherein P is the n-octanol-water partition coefficient for the materials benzyl alcohol, geraniol, farnesol and GALAXOLIDE®. Reference numeral 1703 is the data point for benzyl alcohol. Reference numeral 1704 is the data point for geraniol. Reference numeral 1704a shows the standard deviation for the data point for geraniol. Reference numeral 1705 is the data point for farnesol having the structure:

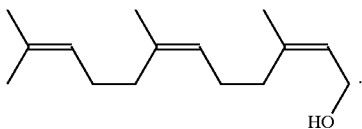

Reference numeral 1705a represents the standard deviation for the data point for farnesol. Reference numeral 1706 is the data point for GALAXOLIDE®. Reference numeral 1708 is the graph of aroma chemical loading efficiency versus $\log_{10}P$ wherein P is the n-octanol-water partition coefficient for the aroma chemicals The graph is also represented by the equation: $\epsilon=16\cdot1433\{\log_{10}P\}-5\cdot922$.

Aroma chemical loading efficiency is shown by the equation:

$$\varepsilon = \left(\frac{m_c}{m_T}\right) \times 100,$$

wherein the term: $m_c$ represents the mass of aroma chemicals encapsulated in the microparticles and the term: $m_T$ represents the total mass of the aroma chemical in the microparticle slurry.

The n-octanol/water partitioning coefficient of a perfume material indicated by the term "P" is the ratio between its equilibrium concentrations in n-octanol and in water. The perfume materials of our invention have an n-octanol/water partitioning coefficient P of between about 10 and about $10^8$. Since the partitioning coefficients of the perfume compositions of this invention have values between 10 and $10^8$, they are more conveniently given in the form of their logarithm to the base 10, $\log_{10}P$. Thus, the perfume materials useful in the practice of our invention have a $\log_{10}P$ of between about 1 and about 8 as indicated, supra.

The $\log_{10}P$ of many perfume ingredients have been reported; for example, the Pomona 92 database, available from Daylight Chemical Information Systems, Inc. (Daylight CIS), Irvine, Calif., contains many, along with citations to the original literature. However, the $\log_{10}P$ values are most conveniently calculated by the "CLOGP" program, also available from Daylight CIS. This program also lists experimental $\log_{10}P$ values when they are available in the Pomona 92 database. The "calculated $\log_{10}P$" is determined by the fragment approach of Hansch and Leo (*Comprehensive Medicinal Chemistry*, Volume 4, C. Hansch, P. G. Sammens, J. B. Taylor and C. A. Ramsden, Editors, page 295, Pergamon Press, 1990, incorporated by reference herein). The fragment approach is based on the chemical structure of each component of the perfume material and takes into account the numbers and types of atoms, the atom connectivity and chemical bonding. The calculated $\log_{10}P$ values, which are the most reliable and widely used estimates for this physiochemical property, are preferably used instead of the experimental $\log_{10}P$ values in the selection of perfume materials useful in the practice of our invention.

FIG. 18A shows the rotor/stator mixer particle size distribution using 1.2% cetyl trimethyl ammonium chloride having the structure:

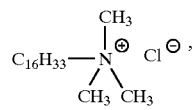

10% candelilla wax and 10% fragrance P-50448. The particle size distribution is set forth using reference numeral 1803. The X axis is represented by reference numeral 1802 which sets forth the particle diameter in microns. The Y axis sets forth the volume percent for each particular particle diameter and is represented by reference numeral 1801. The mean particle size of the particles is 2.4 microns and the distribution is as follows:

90% of particles are finer than: 3.8 microns;
75% of particles are finer than: 2.8 microns;
50% of particles are finer than: 2.0 microns;
25% of particles are finer than: 1.4 microns; and
10% of particles are finer than: 1.1 microns.

Referring to FIG. 18B, FIG. 18B shows a homogenized particle size distribution using a mixture containing 0.5% cetyl trimethyl ammonium chloride having the structure:

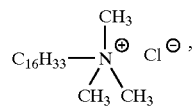

10% candelilla wax and 10% fragrance IB-X-016. The particle size distribution is as follows:

mean particle size: 0.74 microns;
90% of particles are finer than: 2.60 microns;
75% of particles are finer than: 0.70 microns;
70% of particles are finer than: 0.19 microns;
25% of particles are finer than: 0.14 microns; and
10% of particles are finer than: 0.12 microns.

The X axis is represented by reference numeral 1812 and indicates particle diameter in microns. The Y axis is indicated by reference numeral 1811 and indicates volume percent of particles of particular particle diameter. Reference numeral 1813 shows those particles having a particle diameter of from zero up to about 0.4 microns. Reference numeral 1814 shows those particles having a particle diameter of from about 0.4 up to about 1 micron. Reference numeral 1815 shows those particles having a particle diameter of from about 1.3 up to about 1.6 microns.

The following examples illustrate embodiments of this invention. All parts, percentages and proportions referred to herein and in the appended claims are by weight, unless otherwise indicated.

EXAMPLE A

Fragrance Composition

The following fragrance composition is prepared for use in Examples I–IV, infra.

| Ingredients | Parts by Weight |
|---|---|
| hexyl cinnamic aldehyde | 15 |
| cis-3-hexenyl salicylate | 9 |
| ISO E SUPER ® (Trademark of International Flavors & Fragrances Inc. of New York, NY) having the structure: | 9 |

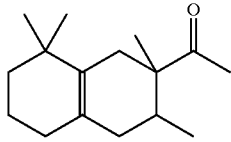

| LILIAL ® (Trademark of Givaudan, Inc. of Clifton, NJ) | 30 |
|---|---|
| β-ionone | 8 |
| γ-methyl ionone | 6 |
| citronellol | 25 |
| methyl nonyl acetaldehyde | 15 |
| allyl cyclohexyl propane | 5 |
| α-terpineol | 6 |
| borneol | 5 |
| β-phenyl ethyl alcohol | 25 |
| linalool | 9 |
| allyl amyl glycolate | 7 |
| linalyl acetate | 12 |
| dihydromyrcenol | 5 |
| isobornyl acetate | 20 |
| methyl chavicol | 5 |
| benzyl acetate | 9 |
| camphor | 15 |
| styralyl acetate | 5 |
| eucalyptus oil | 13 |
| cis-3-hexenyl acetate | 4 |

EXAMPLE I

Preparation of Microparticles Using Silverson L4R Laboratory Mixer of FIG. 11G

The following procedure is used for the preparation of microparticles with the fragrance of Example A and candelilla wax using a Silverson L4R laboratory mixer as set forth in FIG. 11G and described, supra. The resulting formulation is:

74.0% water;
15% candelilla wax;
10% fragrance of Example A; and
1.0% cetyl trimethyl ammonium chloride having the structure:

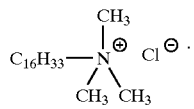

(1) 37.5 Grams of candelilla wax is placed in an oven at 125° C. and allowed to melt.

(2) 314.87 Grams of deionized water is placed into a steam jacket in a one gallon tank.

(3) The bottom of the tank is piped into the suction side of a Silverson in-line model L4R laboratory rotor/stator mixer. The discharge of the mixer was piped back into the tank to allow for recirculation.

(4) The mixer is turned on slowly and the water is drawn into the mixer and pumped back into the tank.

(5) 3.88 Grams of 29% cetyl trimethyl ammonium chloride solution in water is added to the water.

(6) Steam is turned on the jacket and the water/surfactant solution is heated to 90° C. A counter-rotating propeller mixer mounted in the tank ensures that the temperature of the water is homogeneous.

(7) Candelilla wax is removed from the oven and 18.75 grams of the fragrance of Example A is mixed into the wax by hand with a glass rod.

(8) The fragrance/wax mixture is poured into the tank. The counter-rotating propeller mixer speed is increased to disperse the wax/oil into the water and keep the emulsion homogeneous.

(9) The mixer is turned on maximum speed and is allowed to emulsify for one minute. The steam rate is adjusted to maintain a product temperature of 90° C.

(10) The mixer speed is reduced to a minimum and the three-way valve located on the mixer discharge is turned to divert the emulsion through a Parker dual heat transfer coil to solidify the emulsified wax and reduce the slurry temperature to ambient.

The product produced in Example I, supra, gives rise to aesthetically pleasing, long lasting fragrance effects when used in hair care preparation in accordance with the use of Examples:

U.S. Pat. No. 5,653,968 issued on Aug. 5, 1997, entitled "RINSE-OFF HAIR CARE COMPOSITIONS"; and
U.S. Pat. No. 5,653,969 issued on Aug. 5, 1997, entitled "LOW RESIDUE HAIR CARE COMPOSITIONS".

Furthermore, the product produced in Example I, on use with the aforementioned products, yields a consumer perceivable, statistically significant burst of fragrance upon blow-drying with heat.

EXAMPLE II

Use of Shampoo/conditioner 0.98 Grams of the slurry of Example I containing:
15% candelilla wax;
10% fragrance of Example A; and
1.0% cetyl trimethyl ammonium chloride
is admixed in a Vortex mixer with 14 grams of a non-fragranced shampoo composition, as described in U.S. Pat. No. 5,658,868 issued on Aug. 19, 1997, incorporated by reference herein and containing:
5% (weight) 2-decenyl sulfonate;

15% (weight) sodium sulfosuccinate ester of n-decanolamide;
25% (weight) lauroamphocarboxyglycinate;
4% (weight) coconut amide;
3% (weight) glycol distearate;
4% (weight) aloe vera;
1% (weight) wheat germ oil; and
43% (weight) water.

The resultant mixture is applied to hair in a washing procedure and has an effective fragrance level of 0.6%. The hair is left to dry. After 36 hours, the dried hair thus washed has an aesthetically pleasing aroma having:

(1) a substantivity of 9 on a scale of 1–10;
(2) a quality of 10 on a scale of 1–10; and
(3) an intensity of 6 on a scale of 1–10.

Furthermore, the product produced in Example I, on use with the above product of this Example II, yields a consumer perceivable, statistically significant burst of fragrance upon blow-drying with heat.

What is claimed is:

1. A fragranced hair care composition comprising an unfragranced hair care base and intimately admixed therewith a perfuming quantity and concentration of a microparticulate encapsulated fragrance composition comprising substantially ellipsoidal hydrophobic particles, each of which has a continuous outer surface and an internal matrix volume consisting essentially of:
   i. a single phase solid solution of a matrix material selected from the group consisting of at least one hydrophobic polymer selected from the group consisting of a polyamide having a molecular weight in the range of from about 6,000 up to about 12,000 and at least one hydrophobic wax selected from the group consisting of carnauba wax, candelilla wax, mixtures of cetyl palmitate with carnauba wax, mixtures of cetyl palmitate with candelilla wax, ozokerite wax, ceresin wax low density polyethylene wax having a molecular weight in the range of from about 500 up to about 6,000, each of which polymer and wax has a melting point in the range of from about 35° C. up to about 120° C. at 1 atmosphere pressure, having dissolved therein at least one hydrophobic fragrance material, each of said substantially ellipsoidal hydrophobic particles having an outer surface and an internal matrix volume; and
   ii. a substantially hydrophilic surfactant which is either a cationic surfactant, an anionic surfactant, a nonionic surfactant or a zwitterionic surfactant and which is selected from the group consisting of a cationic modified starch in admixture with a partially-hydrolyzed polyvinyl acetate having a degree of hydrolysis of between about 73% up to about 99% and having a molecular weight in the range of from about 5,000 up to about 67,000, tetra(2-hydroxypropyl) ethylenediamine, a cetyl trimethylammonium halide, a quaternary ammonium polysilane derivative in admixture with a partially-hydrolyzed polyvinyl acetate having a degree of hydrolysis of between about 73% up to about 99% and having a molecular weight in the range of from about 5,000 up to about 67,000, and a cationic polysaccharide derivative, said hydrophilic surfactant:
      (a) being substantially entirely coated on and fixedly bonded to the entirety of the outer surface of the single phase solid solution in the form of a submicron layer of surfactant, or
      (b) being located proximate to and immediately, substantially beneath the entirety of the outer surface of the solid solution and substantially within the said internal matrix volume, or
      (c) being both substantially entirely coated on and fixedly bonded to the entirety of the outer surface of the single phase solid solution in the form of a submicron layer of surfactant, and being located proximate to and immediately, substantially beneath the entirety of the outer surface of the solid solution and substantially within the said internal matrix volume,
   whereby when the surfactant is a cationic surfactant, the particle is positively charged, when the surfactant is an anionic surfactant, the particle is negatively charged, when the surfactant is a nonionic surfactant, the particle has a neutral charge and when the surfactant is a zwitterionic surfactant, the particle has a variable charge,
   each of the components of said fragrance material having a vapor pressure in the range of from 0.0001 mm/Hg up to 2.0 mm/Hg at 25° C. and a calculated $\log_{10}P$ in the range of from about 1 up to about 8 wherein P is the partition coefficient of the fragrance material between n-octanol and water, said hydrophobic particle having an outside diameter in the range of from about 0.50 up to about 20 microns, the concentration of fragrance material in said polymer or said wax being from about 5% up to about 60% by weight of said particle, the weight percent of said surfactant being from about 0.01% up to about 5% by weight of said particle, with said wax, said surfactant and said polymer each being non-reactive with said fragrance material and one another, prepared by means of a process comprising the steps of:
   (1) intimately admixing at least one hydrophobic fragrance material with at least one hydrophobic polymer and/or at least one hydrophobic wax to form a first liquid single phase mixture at a temperature greater than or equal to the melting point of said polymer, said wax, or in the case of mixtures, the melting point of the highest melting point component of the materials in the mixture;
   (2) intimately admixing a surfactant with an aqueous composition comprising water to form a second mixture which is an aqueous solution;
   (3) blending said first mixture and said second mixture at a temperature of between 60° C. and the boiling point of said aqueous composition whereby a micro emulsion is formed; and
   (4) causing the hydrophobic perfume-containing composition in the solid phase to form as an aqueous suspension of solid-phase particles
   wherein the weight percent for forming said first mixture is in the range of from about 5% up to about 60% by weight of said first mixture; and wherein the weight percent of surfactant in the second mixture is from about 0.01% up to about 5% by weight of said second mixture.

2. The composition of claim 1 wherein in the process for producing a microparticulate encapsulated fragrance composition in step (4), the solid phase particles are formed by means of cooling the aqueous suspension to a temperature in the range of from about 10° C. up to about 30° C.

3. A fragranced hair care composition comprising an unfragranced hair care base and intimately admixed therewith a perfuming quantity and concentration of a microparticulate encapsulated fragrance composition comprising substantially ellipsoidal hydrophobic particles, each of which has a continuous outer surface and an internal matrix volume consisting essentially of:
  i. a single phase solid solution of a matrix material selected from the group consisting of at least one hydrophobic polymer selected from the group consisting of a polyamide having a molecular weight in the range of from about 6,000 up to about 12,000 and at least one hydrophobic wax selected from the group consisting of carnauba wax, candelilla wax, mixtures of cetyl palmitate with carnauba wax, mixtures of cetyl palmitate with candelilla wax, ozokerite wax, ceresin wax low density polyethylene wax having a molecular weight in the range of from about 500 up to about 6,000, each of which polymer and wax has a melting point in the range of from about 35° C. up to about 120° C. at 1 atmosphere pressure, having dissolved therein at least one hydrophobic fragrance material, each of said substantially ellipsoidal hydrophobic particles having an outer surface and an internal matrix volume; and
  ii. a substantially hydrophilic surfactant which is either a cationic surfactant, an anionic surfactant, a nonionic surfactant or a zwitterionic surfactant and which is selected from the group consisting of a cationic modified starch in admixture with a partially-hydrolyzed polyvinyl acetate having a degree of hydrolysis of between about 73% up to about 99% and having a molecular weight in the range of from about 5,000 up to about 67,000, tetra(2-hydroxy-propyl) ethylenediamine, a cetyl trimethylammonium halide, a quaternary ammonium polysilane derivative in admixture with a partially-hydrolyzed polyvinyl acetate having a degree of hydrolysis of between about 73% up to about 99% and having a molecular weight in the range of from about 5,000 up to about 67,000, and a cationic polysaccharide derivative, said hydrophilic surfactant:
    (a) being substantially entirely coated on and fixedly bonded to the entirety of the outer surface of the single phase solid solution in the form of a submicron layer of surfactant, or
    (b) being located proximate to and immediately, substantially beneath the entirety of the outer surface of the solid solution and substantially within the said internal matrix volume, or
    (c) being both substantially entirely coated on and fixedly bonded to the entirety of the outer surface of the single phase solid solution in the form of a submicron layer of surfactant, and being located proximate to and immediately, substantially beneath the entirety of the outer surface of the solid solution and substantially within the said internal matrix volume,
  whereby when the surfactant is a cationic surfactant, the particle is positively charged, when the surfactant is an anionic surfactant, the particle is negatively charged, when the surfactant is a nonionic surfactant, the particle has a neutral charge and when the surfactant is a zwitterionic surfactant, the particle has a variable charge,
  each of the components of said fragrance material having a vapor pressure in the range of from 0.0001 up to 2.0 mm/Hg at 25° C. and a calculated $\log_{10} P$ in the range of from about 1 up to about 8 wherein P is the partition coefficient of the fragrance material between n-octanol and water, said hydrophobic particle having an outside diameter in the range of from about 0.50 up to about 20 microns, the concentration of fragrance material in said polymer or said wax being from about 5% up to about 60% by weight of said particle, the weight percent of said surfactant being from about 0.01% up to about 5% by weight of said particle, with said wax, said surfactant and said polymer each being non reactive with said fragrance material and one another, prepared by means of a process comprising the steps of:
    (1) intimately admixing at least one hydrophobic fragrance material with at least one hydrophobic polymer and/or at least one hydrophobic wax and at least one surfactant to form a first liquid single phase mixture at a temperature greater than or equal to the melting point of said polymer, said wax, or in the case of mixtures, the melting point of the highest melting point component of the materials in the mixture;
    (2) blending said first single liquid with an aqueous composition comprising water whereby a micro emulsion is formed; and
    (3) causing the hydrophobic perfume-containing composition in the solid phase to form as an aqueous suspension of solid-phase particles
  wherein the weight percent for forming said first mixture is in the range of from about 5% up to about 60% by weight of said first mixture; and wherein the weight percent of surfactant in the second mixture is from about 0.01% up to about 5% by weight of said second mixture.

4. The composition of claim 1 wherein the permeation rate of the fragrance material through the wax or the polymer is in the range of from about $$10^{-8} \frac{\text{mg} - \text{mm}}{\text{cm}^2 - \text{min}}$$

to about $$8 \times 10^{-3} \frac{\text{mg} - \text{mm}}{\text{cm}^2 - \text{min}}$$

as determined by the IFF permeation test.

5. The composition of claim 3 wherein the permeation rate of the fragrance material through the wax or the polymer is in the range of from about $10^{-8}$ $$\frac{\text{mg} - \text{mm}}{\text{cm}^2 - \text{min}}$$

up to about $$8 \times 10^{-3} \frac{\text{mg} - \text{mm}}{\text{cm}^2 - \text{min}}$$

as determined by the IFF permeation test.

6. The composition of claim 4 wherein, said hydrophilic surfactant is substantially entirely coated on and fixedly bonded to the entirety of the outer surface of the single phase solid solution in the form of a submicron layer of surfactant.

7. The composition of claim 4 wherein said hydrophilic surfactant is located proximate to and immediately, substantially beneath the entirety of the outer surface of the solid solution and substantially within the said internal matrix volume.

8. The composition of claim 4 wherein said hydrophilic surfactant is both substantially entirely coated on and fixedly bonded to the entirety of the outer surface of the single phase solid solution in the form of a submicron layer of surfactant, and is located proximate to and immediately substantially beneath the entirety of the outer surface of the solid solution and substantially within the said internal matrix volume.

9. The composition of claim 5 wherein, said hydrophilic surfactant is substantially entirely coated on and fixedly bonded to the entirety of the outer surface of the single phase solid solution in the form of a submicron layer of surfactant.

10. The composition of claim 5 wherein said hydrophilic surfactant is located proximate to and immediately, substantially beneath the entirety of the outer surface of the solid solution and substantially within the said internal matrix volume.

11. The composition of claim 5 wherein said hydrophilic surfactant is both substantially entirely coated on and fixedly bonded to the entirety of the outer surface of the single phase solid solution in the form of a submicron layer of surfactant, and is located proximate to and immediately substantially beneath the entirety of the outer surface of the solid solution and substantially within the said internal matrix volume.

* * * * *